United States Patent
Armstrong et al.

(10) Patent No.: US 9,974,918 B2
(45) Date of Patent: *May 22, 2018

(54) PORTABLE OXYGEN DELIVERY DEVICE

(75) Inventors: Peter Armstrong, Poway, CA (US);
Ronald Richard, Escondido, CA (US);
Paul Edwards, Encinitas, CA (US);
Ningda Andy Dai, Carlsbad, CA (US)

(73) Assignee: Caire Inc., Ball Ground, GA (US)

( * ) Notice: Subject to any disclaimer, the term of this patent is extended or adjusted under 35 U.S.C. 154(b) by 590 days.

This patent is subject to a terminal disclaimer.

(21) Appl. No.: 13/082,345

(22) Filed: Apr. 7, 2011

(65) Prior Publication Data
US 2011/0247620 A1    Oct. 13, 2011

Related U.S. Application Data

(60) Provisional application No. 61/321,824, filed on Apr. 7, 2010.

(51) Int. Cl.
*A61M 16/10* (2006.01)
*B01D 53/047* (2006.01)
(Continued)

(52) U.S. Cl.
CPC ........ *A61M 16/10* (2013.01); *A61M 16/0677* (2014.02); *A61M 16/101* (2014.02); *A61M 16/107* (2014.02); *A61M 16/204* (2014.02); *B01D 53/047* (2013.01); *C01B 13/0251* (2013.01); *C01B 13/0259* (2013.01); *A61M 11/06* (2013.01); *A61M 2016/1025* (2013.01); *A61M 2205/18* (2013.01); *A61M 2205/3584* (2013.01); *A61M 2205/3653* (2013.01); *A61M 2205/42* (2013.01); *A61M 2205/505* (2013.01); *A61M 2205/8206* (2013.01); *A61M 2205/8262* (2013.01); *A61M 2205/8268* (2013.01); *A61M 2209/084* (2013.01); *A61M 2230/202* (2013.01);
(Continued)

(58) Field of Classification Search
CPC ............ A61M 16/20; A61M 2016/101; B01D 2256/12; F04B 39/066; F04C 29/04; F04C 28/00; F04C 28/06; F04C 28/28
USPC ............ 128/204.18, 204.23, 204.26, 205.11, 128/205.22, 205.24
See application file for complete search history.

(56) References Cited

U.S. PATENT DOCUMENTS 3,052,098 A * 9/1962 Ebert .............................. 60/492
3,181,510 A    5/1965 Hovey
(Continued)

*Primary Examiner* — LaToya M Louis
(74) *Attorney, Agent, or Firm* — Cook Alex Ltd.; R. Blake Johnston

(57) ABSTRACT

Devices, systems, and methods, include an oxygen delivery device that includes an oxygen delivery module, at least one sensor to detect patient breathing, and a controller configured to control the oxygen delivery module to cause the oxygen delivery module to deliver oxygen to the patient based on data from the at least one sensor such that in response to a determination, based on data from the at least one sensor, that no breathing is detected for a first predetermined period of time, the controller causes the oxygen delivery module to deliver oxygen to the patient in continuous flow mode, and in response to a determination, based on additional data from the at least one sensor, that breathing is detected for a second period of time, the controller causes the oxygen delivery module to deliver oxygen to the patient in a pulse flow mode.

7 Claims, 35 Drawing Sheets

(51) Int. Cl.
  *C01B 13/02* (2006.01)
  *A61M 16/06* (2006.01)
  *A61M 16/20* (2006.01)
  *A61M 11/06* (2006.01)

(52) U.S. Cl.
  CPC ... *A61M 2230/205* (2013.01); *A61M 2230/63* (2013.01); *B01D 2253/108* (2013.01); *B01D 2253/25* (2013.01); *B01D 2256/12* (2013.01); *B01D 2257/102* (2013.01); *B01D 2259/40005* (2013.01); *B01D 2259/40009* (2013.01); *B01D 2259/4061* (2013.01); *B01D 2259/4145* (2013.01); *B01D 2259/4533* (2013.01); *B01D 2259/4541* (2013.01)

(56) References Cited

U.S. PATENT DOCUMENTS

| | | | | |
|---|---|---|---|---|
| 3,521,981 | A | 7/1970 | Krzyszczuk | |
| 3,716,033 | A | 2/1973 | Lepine | |
| 4,491,459 | A | 1/1985 | Pinkerton | |
| 4,576,616 | A | 3/1986 | Mottram et al. | |
| 4,657,495 | A * | 4/1987 | Sakamaki | F04C 27/008 384/478 |
| 4,709,682 | A * | 12/1987 | Kato | F02B 33/38 123/559.1 |
| 4,836,759 | A | 6/1989 | Lloyd | |
| 5,165,397 | A * | 11/1992 | Arp | 128/204.21 |
| 5,268,021 | A * | 12/1993 | Hill et al. | 95/98 |
| 5,366,541 | A | 11/1994 | Hill et al. | |
| 5,380,164 | A | 1/1995 | Fry et al. | |
| 5,383,774 | A * | 1/1995 | Toyama et al. | 418/66 |
| 5,413,625 | A | 5/1995 | Chao et al. | |
| 5,443,062 | A | 8/1995 | Hayes | |
| RE35,099 | E | 11/1995 | Hill | |
| 5,551,854 | A | 9/1996 | Edwards | |
| 5,593,478 | A | 1/1997 | Hill et al. | |
| 5,603,315 | A * | 2/1997 | Sasso, Jr. | 128/204.18 |
| 5,627,323 | A | 5/1997 | Stern | |
| 5,674,051 | A | 10/1997 | Maruyama | |
| 5,730,778 | A | 3/1998 | Hill et al. | |
| 5,858,062 | A | 1/1999 | McCulloh et al. | |
| 5,893,275 | A | 4/1999 | Henry | |
| 5,928,189 | A | 7/1999 | Phillips et al. | |
| 6,056,804 | A * | 5/2000 | Keefer et al. | 95/96 |
| 6,106,255 | A | 8/2000 | Viegas et al. | |
| 6,120,273 | A | 9/2000 | Mallen | |
| 6,401,686 | B1 | 6/2002 | Prueitt et al. | |
| 6,551,384 | B1 | 4/2003 | Ackley et al. | |
| 6,605,136 | B1 | 8/2003 | Graham et al. | |
| 6,612,117 | B2 | 9/2003 | Kasmer | |
| 6,691,702 | B2 | 2/2004 | Appel et al. | |
| 6,729,327 | B2 * | 5/2004 | McFarland, Jr. | 128/203.12 |
| 6,749,405 | B2 | 6/2004 | Bassine | |
| 6,824,590 | B2 | 11/2004 | Dee et al. | |
| 7,094,275 | B2 * | 8/2006 | Keefer et al. | 96/125 |
| 7,114,932 | B1 * | 10/2006 | Bassine | 418/268 |
| 7,273,051 | B2 | 9/2007 | Whitley et al. | |
| 7,279,029 | B2 | 10/2007 | Occhialini et al. | |
| 7,331,343 | B2 * | 2/2008 | Schmidt et al. | 128/204.18 |
| 7,350,521 | B2 | 4/2008 | Whitley et al. | |
| 7,402,193 | B2 | 7/2008 | Bliss et al. | |
| 7,473,299 | B2 | 1/2009 | Occhialini et al. | |
| 7,510,601 | B2 | 3/2009 | Whitley et al. | |
| 7,686,870 | B1 | 3/2010 | Deane et al. | |
| 7,837,761 | B2 * | 11/2010 | Bliss et al. | 95/12 |
| 8,113,805 | B2 | 2/2012 | Kemp | |
| 2002/0096174 | A1 * | 7/2002 | Hill et al. | 128/205.11 |
| 2002/0197177 | A1 * | 12/2002 | Fujiwara | F04C 18/086 418/220 |
| 2007/0227360 | A1 | 10/2007 | Atlas et al. | |
| 2008/0053310 | A1 | 3/2008 | Bliss et al. | |
| 2008/0110459 | A1 * | 5/2008 | Farbarik | 128/204.18 |
| 2008/0156328 | A1 | 7/2008 | Taube | |
| 2008/0159896 | A1 * | 7/2008 | Kishi | F04C 18/3442 418/88 |
| 2008/0193314 | A1 | 8/2008 | Cho et al. | |
| 2008/0236584 | A1 * | 10/2008 | Holder | 128/204.23 |
| 2008/0279709 | A1 | 11/2008 | Knight | |
| 2008/0282880 | A1 * | 11/2008 | Bliss et al. | 95/11 |
| 2009/0126731 | A1 * | 5/2009 | Dunsmore et al. | 128/203.12 |
| 2009/0145428 | A1 | 6/2009 | Sward et al. | |
| 2009/0167698 | A1 | 7/2009 | Altas et al. | |
| 2009/0180912 | A1 | 7/2009 | Morozumi et al. | |
| 2009/0199855 | A1 | 8/2009 | Davenport | |
| 2009/0211448 | A1 | 8/2009 | McClain | |
| 2009/0241958 | A1 * | 10/2009 | Baker, Jr. | 128/204.23 |
| 2009/0266359 | A1 * | 10/2009 | Flint | 128/204.18 |
| 2010/0006097 | A1 * | 1/2010 | Frater et al. | 128/204.18 |
| 2010/0045096 | A1 | 2/2010 | Schonlau et al. | |
| 2010/0051030 | A1 | 3/2010 | Richard et al. | |
| 2010/0065054 | A1 | 3/2010 | Bowman et al. | |
| 2010/0183467 | A1 * | 7/2010 | Sundheim | F04C 13/007 418/88 |
| 2011/0058970 | A1 | 3/2011 | Hugenroth | |
| 2011/0073107 | A1 | 3/2011 | Rodman et al. | |
| 2011/0114094 | A1 | 5/2011 | Stone et al. | |
| 2011/0247621 | A1 | 10/2011 | Richard et al. | |
| 2011/0247622 | A1 | 10/2011 | Schneider et al. | |
| 2012/0000462 | A1 | 1/2012 | Edwards et al. | |

\* cited by examiner

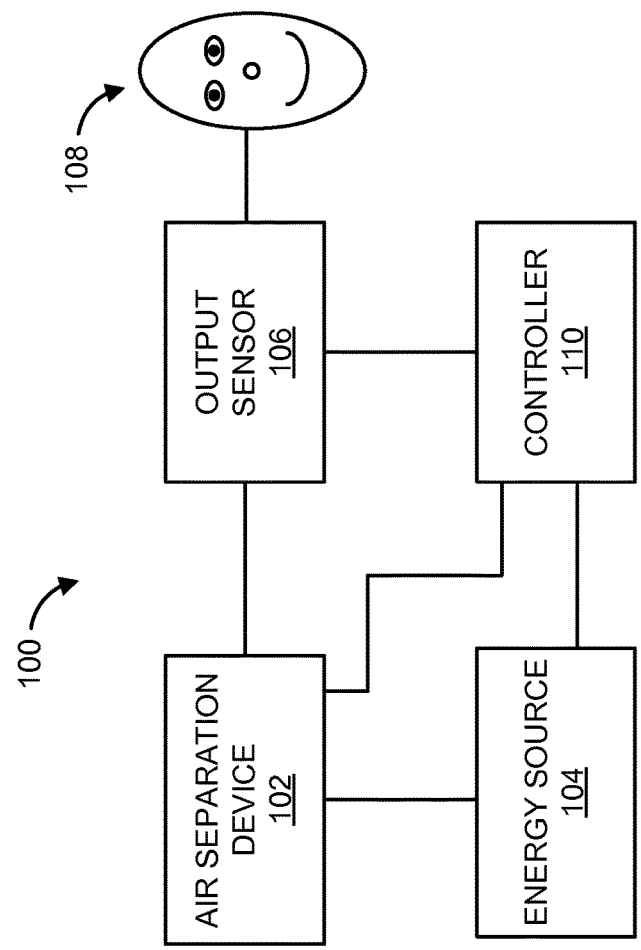

FIG. 21

```
                    BEGIN                                 1300

│
                      ▼
┌─────────────────────────────────────────────┐
│ Produce concentrated oxygen using an oxygen │
│ delivery device that includes an oxygen     │
│ delivery module to produce at least the     │   1310
│ concentrated oxygen, and a gas moving       │
│ device to deliver air to the oxygen         │
│ delivery module.                            │
└─────────────────────────────────────────────┘
                      │
                      ▼
┌─────────────────────────────────────────────┐
│ Convert at least some of liquid medication  │
│ contained in a medication chamber of a      │   1320
│ nebulizer into aerosol medication by        │
│ directing the concentrated oxygen produced  │
│ by the oxygen delivery module into the      │
│ nebulizer.                                  │
└─────────────────────────────────────────────┘
                      │
                      ▼
┌─────────────────────────────────────────────┐
│ Deliver at least some of the concentrated   │
│ oxygen directed into the nebulizer and at   │
│ least some of the converted aerosol         │   1330
│ medication for inhalation by a patient      │
│ through a nebulizer outlet port.            │
└─────────────────────────────────────────────┘
                      │
                      ▼
                     END
```

FIG. 23

PORTABLE OXYGEN DELIVERY DEVICE

CROSS-REFERENCE TO RELATED APPLICATION

The present application claims benefit and priority to U.S. Provisional Patent Application No. 61/321,824, filed Apr. 7, 2010, and entitled "Portable Oxygen Concentration System and Method of Using the Same," the content of which is hereby incorporated by reference in its entirety.

FIELD

This disclosure relates generally to a device, mechanism and method for an oxygen delivery device, and in particular, to a portable oxygen concentration system for an ambulatory respiratory subject that allows the subject to lead a more normal and productive life.

BACKGROUND

Supplemental oxygen is necessary for patients suffering from lung disorders; for example, pulmonary fibrosis, sarcoidosis, or occupational lung disease. For such patients, oxygen therapy is an increasingly beneficial, life-giving development. While not a cure for lung disease, supplemental oxygen increases blood oxygenation, which reverses hypoxemia. This therapy prevents long-term effects of oxygen deficiency on organ systems—in particular, the heart, brain and kidneys.

Oxygen treatment is also prescribed for Chronic Obstructive Pulmonary Disease (COPD), which afflicts about twenty-four million people in the U.S., and for other ailments that weaken the respiratory system, such as heart disease and AIDS. Supplemental oxygen therapy is also prescribed for asthma and emphysema.

The normal prescription for COPD patients requires supplemental oxygen flow via nasal cannula or mask twenty four hours per day. The average patient prescription is two liters per minute of high concentration oxygen to increase the oxygen level of the total air inspired by the patient from the normal 21% to about 40%. While the average oxygen flow requirement is two liters per minute, the average oxygen concentrator has a capacity of four to six liters of oxygen per minute. This extra capacity is occasionally necessary for certain patients who have developed more severe problems, are not generally able to leave the home (as ambulatory patients) and do not require a portable oxygen supply.

There are currently three modalities for supplemental medical oxygen: high pressure gas cylinders, cryogenic liquid in vacuum insulated containers or thermos bottles commonly called "dewars," and oxygen concentrators. Some patients require in-home oxygen only while others require in-home as well as ambulatory oxygen depending on their prescription. All three modalities are used for in-home use, although oxygen concentrators are preferred because they do not require dewar refilling or exchange of empty cylinders with full ones. Some of the conventional home oxygen concentrators, however, do have their drawbacks. They consume relatively large amounts of electricity (250-500 Watts), are relatively large (about the size of a night stand), are relatively heavy (weight about 30-50 lbs.), emit quite a bit of heat, and are relatively noisy.

Only small high pressure gas bottles and small liquid dewars are truly portable enough to be used for ambulatory needs (outside the home). Either modality may be used for both in-home and ambulatory use or may be combined with an oxygen concentrator which would provide in-home use.

As described below, the current oxygen-supplying methods and devices have proven cumbersome and unwieldy and there has been a long-felt need for an improved portable device for supplying oxygen to the user.

For people who need to have oxygen and operate away from an oxygen-generating or oxygen-storage source such as a stationary oxygen system (or even a portable system which cannot be readily transported), the two most prescribed options generally available to patients are: (a) to carry with them small cylinders typically in a wheeled stroller; and (b) to carry portable containers typically on a shoulder sling. Both gaseous oxygen and liquid oxygen options have substantial drawbacks, but from a medical view, both have the ability to increase the productive life of a patient.

A drawback of the gaseous oxygen option is that the small cylinders of gaseous oxygen can only provide gas for a short duration. Another drawback is that a patient's high-pressure gaseous oxygen cylinders are not allowed in some locations such as airplanes because of safety considerations. A further drawback of the gaseous oxygen option is the refill requirement for oxygen once the oxygen has been depleted from the cylinder. These small gas cylinders must be picked up and refilled by the home care provider at a specialized facility. This requires regular visits to a patient's home by a provider and a substantial investment in small cylinders by the provider because so many are left at the patient's home and refilling facility. Although it is technically possible to refill these cylinders in the patient's home using a commercial oxygen concentrator that extracts oxygen from the air, this task would typically require an on-site oxygen compressor to boost the output pressure of the concentrator to a high level in order to fill the cylinders. Some disadvantages of common on-site oxygen compressors are that they are expensive, loud and emit a lot of heat.

Additionally, attempting to compress the oxygen in pressurized canisters in the home is potentially dangerous, especially for untrained people.

This approach presents several safety concerns for in-home use. For example, in order to put enough of this gas in a portable container, it must typically be compressed to high pressure (2000 psi). Compressing oxygen from 5 psi (the typical output of an oxygen concentrator) to 2000 psi will produce a large amount of heat (enough to raise the temperature 165 degrees C. per stage based on three adiabatic compression stages with intercooling.) This heat, combined with the oxygen which becomes more reactive at higher pressures, sets up a potential combustion hazard in the compressor in the patient's home. Thus, operation of a high-pressure gas system in the patient's home is dangerous and not a practical solution.

The convenience and safety issues are not the only drawbacks of this compressed oxygen approach. Another drawback is that the compressors or pressure boosters needed are costly because they require special care and materials needed for high pressure oxygen compatibility.

Turning now to the liquid oxygen storage option, its main drawback is that it requires a base reservoir—a stationary reservoir base unit within the patient's home about the size of a standard beer keg—which may be refilled about once a week from an outside source. Liquid oxygen can then be transferred from the patient's base unit to a portable dewar, which can be used by the ambulatory patient. Also, with the liquid oxygen option, there is substantial waste, as a certain amount of oxygen is lost during the transfer to the portable containers and from evaporation. It is estimated that 20% of the entire contents of the base cylinder will be lost in the course of two weeks because of losses in transfer and due to normal evaporation. These units will typically boil dry over a period of 30 to 60 days even if no oxygen is withdrawn.

Home refilling systems that produce liquid oxygen and have the capability of refilling portable liquid oxygen dewars have been proposed. However, these devices require the user to perform the task of refilling bottles and add tens of dollars per month to the user's electric bill, which may not be reimbursable.

There are other complications with these portable high-pressure cylinders and liquid dewars. Typically, supplemental oxygen is supplied to the patient by a home care provider, in exchange for which the provider receives a fixed monetary payment from insurance companies or Medicare regardless of the modality. Oxygen concentrators are preferred by the provider as the least expensive option for supplying the patient's at-home needs. For outside the home use, however, only small high-pressure gas bottles and small liquid dewars are portable enough to be used for ambulatory needs. Either one of these two modalities may be used for both in-home and ambulatory use or may be combined with an oxygen concentrator, which would provide in-home use. In either case, the home care provider must make costly weekly or biweekly trips to the patient's home to replenish the oxygen. One of the objectives of the systems, devices, and methods disclosed herein is to eliminate these costly "milk runs."

So-called "portable" oxygen concentrators are commercially available for providing patients with gaseous oxygen by converting ambient air into concentrated gaseous oxygen. However, such devices are still relatively bulky (e.g., they are packaged in a suitcase) and are portable only in the sense that they are capable of being transported to another point of use via an automobile or an airplane. An example of such a transportable device is a 3 LPM concentrator mounted on its own cart. This example device weighs 18 lbs., with the battery, and also requires about 145 Watts of power. A further example device is one that weighs about 21 lbs. with battery and has a similar flow rate and power requirements to the above devices.

Even without a battery, these devices are too heavy for the average ambulatory respiratory patient. With the weight of a battery, these conventional devices are not "portable" in the true sense of the word because transportation from one point to another is still cumbersome. Because these devices have relatively large power consumption requirements, they also require a sizable battery.

Further, in addition to the weight and power consumption problems with the above oxygen concentrators, none of these conventional concentrators are particularly quiet. They produce noise levels similar to those produced by a home concentrator. For example, some of these devices can produce noise at 55 dBA (decibels), which is about the sound level of a normal conversation. Consequently, none of these conventional oxygen concentrators are suitable for use in environments where low noise is especially important, e.g., restaurants, libraries, churches and theatres.

SUMMARY

Thus, a long-felt need exists for a truly portable oxygen concentration system that eliminates the need for high-pressure gas cylinders and liquid dewars, the constant refilling/replacing requirements associated with high-pressure gas cylinders and liquid dewars, and the need for a separate home oxygen concentration system for ambulatory respiratory patients. The portable oxygen concentration systems and devices described herein are light enough so that, even with a battery, an average ambulatory respiratory patient can carry the device. Inherently, the oxygen concentrator devices described herein are implemented to have relatively low power consumption requirements so that a light-weight battery pack or other energy source could be used. Further, the devices described herein are small enough so that they can be conveniently carried by a user, emit a relatively low amount of noise and emit a relatively small amount of heat.

An aspect of the present disclosure involves a portable oxygen concentrator system, also referred to herein as an oxygen delivery device, adapted to be readily transported by a user. The portable oxygen concentrator system includes a rechargeable energy source and a concentrator (also referred to herein as an oxygen delivery module) powered by the energy source. The concentrator converts ambient air into concentrated oxygen gas for the user and includes a plurality of adsorption beds and a rotary valve assembly. The rotary valve assembly is relatively rotatable is with respect to the plurality of adsorption beds to provide valving action for selectively transferring fluids through the plurality of adsorption beds to convert ambient air into concentrated oxygen gas for the user. In some embodiment, the ratio of adiabatic power to oxygen flow for the concentrator is in the range of 6.2 W/LPM to 23.0 W/LPM.

Another aspect of the present disclosure involves a rotary valve assembly for a pressure swing adsorption system having a plurality of adsorption beds. The rotary valve assembly includes a valve port plate and a rotary valve shoe with respective engaged surfaces and are rotatable about a common center of rotation to provide valving action for selectively transferring fluids therethrough. The valve port plate includes at least two ports interconnected with at least two adsorption beds. The rotary valve shoe includes a second valve surface opposite the engaged surface with at least one equalization passage to register with the at least two ports of the port plate to equalize pressure between the at least two adsorption beds.

In one aspect, an oxygen delivery device is disclosed. The oxygen delivery device includes an oxygen delivery module to produce at least concentrated oxygen at a controllable purity level from air, a gas moving device to deliver the air to the oxygen delivery module, at least one controllable motor to controllably drive the gas moving device, an energy source to power at least the at least one controllable motor, a pressure sensor to determine a pressure level produced in the oxygen delivery device, and a purity sensor to determine oxygen purity value produced by the oxygen delivery module. The device also includes a controller to control, based on the determined oxygen purity value and the pressure level, at least the gas moving device's operations and the oxygen delivery module's operations so as to cause the pressure resulting from the operation of the gas moving device to be substantially at a pre-determined pressure value and to cause the purity level of the oxygen produced by the oxygen delivery module to be substantially at a pre-determined purity value.

Embodiments of the device may include any of the features described in the present disclosure, as well as any one or more of the following features.

The oxygen delivery module may include one or more of, for example, a pressure swing adsorption system, a vacuum-pressure swing adsorption system, a liquid oxygen storage system, and/or a high pressure gaseous oxygen system.

The pre-determined pressure value may correspond to a minimum acceptable pressure level, and the pre-determined purity value may correspond to a minimum acceptable oxygen purity level such that energy consumption of the system is reduced. The minimum acceptable pressure level may be between approximately 3-7 psig pressure, and the minimum acceptable oxygen may be between approximately 82-93% oxygen.

The controller may be configured to cause the pressure resulting from the operation of the gas moving device to be substantially at the pre-determined pressure value and to cause the purity level of the oxygen produced by the oxygen delivery module to be substantially at the pre-determined purity value in response to a determination that an energy source to power the oxygen delivery device is a battery. The battery may be a rechargeable battery. The oxygen delivery module may include a plurality of adsorption beds, and a valve assembly configured to direct gas to the plurality of adsorption beds to provide valving action for selectively transferring fluids through the plurality of adsorption beds to separate concentrated oxygen gas from ambient air.

The gas delivery device may be configured to convert a flow of gas from a first pressure to a second pressure. The gas delivery device may include one or more of, for example, a compressor, and/or a vacuum pump.

The oxygen delivery device may further include a rechargeable backup battery to deliver power to a user interface of the oxygen delivery device to indicate change of power supply level (e.g., when power from a primary power source used to power the oxygen delivery device is changed, such as when there is a power loss). The rechargeable backup battery may be configured to power the user interface to indicate power loss when the primary power source used to power the oxygen delivery device cannot deliver power to the oxygen delivery device. The user interface may include a power loss alarm, and the rechargeable backup battery may be configured to deliver power to activate the power loss alarm in response to determination that the primary power source cannot deliver power.

The oxygen delivery device may further include a user interface including an indicator to indicate that maintenance of the oxygen delivery device is required in response to a determination of deviations from a maintenance schedule required for the oxygen delivery device.

The oxygen delivery device may further include a user interface including an indicator to indicate time remaining for a battery-based power, source included with the oxygen delivery device.

The oxygen delivery device may further include a cart to transport the oxygen delivery device and to elevate the oxygen delivery device to provide enhanced access by the patient to the oxygen delivery device.

The oxygen delivery device may further include a device interface module configured to interface with one or more additional devices to enable interoperability functionality of the oxygen delivery device with the one or more additional devices, the interoperability functionality includes one or more of, for example, directing power from a power source of the oxygen delivery device to the one or more additional devices, and/or communicating data between the oxygen delivery device and the one or more additional devices. The device interface module may include at least one dedicated port to interface with at least one of the one or more additional devices. The one or more additional devices may include one or more of, for example, pulse oximeter, pedometer, mathemoglobin monitor, carboxyhemoglobin monitor, totalhemoglobin sensor, a wireless telephone, a wireless modem, and/or a respiration monitor.

The oxygen delivery device may further include a sound system to generate acoustic signals to cancel out at least some of the noise produced from operation of the oxygen delivery device. The sound system may be configured to generate acoustic signals with a phase that is shifted or inverted relative to at least some of the noise produced by operation of the oxygen delivery device. The sound system may include a microphone to measure the noise produced from operation of the oxygen delivery device, a controller to determine characteristics of the noise measured by the microphone and to control the acoustic signals to be generated by a speaker, and the speaker to generate the acoustic signals based on control data provided by the controller.

The oxygen delivery device may further include one or more of, for example, a clock, a radio, an ashtray, and/or a cup holder.

The oxygen delivery device may further include a controller to control at least some operations of the oxygen delivery device, including controlling operations affecting the oxygen delivery module. The controller may include at least one processor based device, and at least one non-transitory memory storage device to store computer instructions, the computer instructions including instructions that when executed on the at least one processor-based device cause the at least one processor-based device to receive data indicative that default operational settings of the oxygen delivery device are to be activated, and in response to the received data, activate the default operational settings of the oxygen delivery device.

The oxygen delivery device may further include a check valve and gas filter included within a housing of the oxygen delivery device and positioned downstream of the oxygen delivery module, the check valve and gas filter configured to prevent moisture present in components of the oxygen delivery device located downstream of the oxygen delivery module from entering the oxygen delivery module.

The oxygen delivery device may further include a purity sensor to determine oxygen purity value, a coupler coupled to the purity sensor, the coupler including an inlet port to receive gas from an external source, and a controller configured to receive data from the purity sensor measuring the purity of oxygen delivered from an external oxygen source, the oxygen from the external oxygen source having a known oxygen purity level, and calibrate the purity sensor based on the purity value measured by the purity sensor for the oxygen having the known oxygen purity level delivered from the external oxygen source. The coupler may include a tee fitting.

The oxygen delivery device may further include an internal battery to power, at least partly, the oxygen delivery device, the internal battery located within a housing of the oxygen delivery device. The oxygen delivery device may also include an external battery pack secured to the housing of the oxygen delivery device to supplement power requirements of the oxygen delivery device.

The oxygen delivery device may further include an internal DC/DC power converter placed within a housing of the oxygen delivery device.

The oxygen delivery device may further include a cart to hold the oxygen delivery device, an AC adapter external to a housing of the oxygen delivery device, the AC adapter being mounted on the cart, and a battery pack external to the housing of the oxygen delivery device, the battery pack being mounted on the cart.

The oxygen delivery device may further include an oxygen container containing oxygen, the container configured to deliver oxygen when oxygen produced by the oxygen delivery device is not sufficient to meet a patient's oxygen needs.

The oxygen delivery device may further include an internal AC adapter placed within a housing of the oxygen delivery device.

The oxygen delivery device may further include one or more of, for example, an internal battery to power, at least partly, the oxygen delivery device, the internal battery located within a housing of the oxygen delivery device, and an external battery pack secured to the housing of the oxygen delivery device to supplement power requirements of the oxygen delivery device. Each of the internal battery and the external battery pack may include batteries having maximum dimensions allowed by regulating agencies.

The oxygen delivery device may further include a device interface module including one or more universal serial bus (USB) ports to enable the oxygen delivery device to function as one of a slave and a host when connected to at least one external device. The one or more USB ports of the device interface module may enable the oxygen delivery device to perform one or more of, for example, communicating data to and from the at least one connected external device, upgrading software-based implemented functionality of at least one operation of the oxygen delivery device, and/or connecting to one or more additional sensors configured to measure one or more of: environmental conditions, operating conditions of the oxygen delivery device, and/or a patient's therapeutic conditions.

The oxygen delivery device may further including a cart to transport the oxygen delivery device, the cart including a retractable/foldable handle. The cart may further include a base to receive a housing of the oxygen delivery device, the housing including integrated wheels such that when the housing with the integrated wheels is received on the base of the cart, the wheels of the housing are used to enable mobility of the cart.

The oxygen delivery device may further include a universal power adapter configured to connect to a plurality of power outlet types and to adapt power delivered from the plurality of power outlet types to produce an output power with power characteristics required for operation of the oxygen delivery device. The universal power adapter may disposed within a housing of the oxygen delivery device.

The oxygen delivery device may further include a fan to cool the oxygen delivery device, at least one temperature sensor, and a controller to control operation of the fan based on data representative of temperature measured by the at least one temperature sensor. The controller is configured to cause one of terminating the operation of the fan and reducing speed of the fan upon a determination, based on the data representative of the temperature, that the measured temperature is below a pre-determined temperature threshold.

In another aspect, a method is disclosed. The method includes receiving from a purity sensor data representative of oxygen purity value in an oxygen delivery module, receiving from a pressure sensor a pressure level value produced by a gas moving device configured to draw air into the oxygen delivery module, and controlling one or more of, for example, the gas moving device's operations and the oxygen delivery module's operations based on the received oxygen purity value and the received pressure level value to cause the pressure resulting from the operation of the gas moving device to be substantially at a pre-determined pressure value and to cause the purity level of the oxygen produced by the oxygen delivery module to be substantially at a pre-determined purity value.

Embodiments of the method may include any of the features described in the present disclosure, including any of the features described above in relation to the device, as well as any of the following features.

Controlling the at least the gas moving device's operations and the oxygen delivery module's operations may include controlling a motor configured to drive the gas moving device.

Controlling the at least the gas moving device's operations and the oxygen delivery module's operations may include determining energy source used to power the oxygen delivery module and the gas moving device, and causing the pressure resulting from the operation of the gas moving device to be substantially at the pre-determined pressure value and causing the purity level of the oxygen produced by the oxygen delivery module to be substantially at the pre-determined purity value in response to a determination that the energy source is a battery.

In a further aspect, an oxygen delivery device is disclosed. The oxygen delivery device includes an oxygen delivery module to produce at least concentrated oxygen, a controller configured to control the oxygen delivery module to cause the oxygen delivery module to deliver oxygen to a patient based on a patient's tidal volume data representative of the normal volume of air displaced between inspiration and expiration by the patient, and further based on a fraction of inspired oxygen (FiO2) value required for the patient.

Embodiments of the device may include any of the features described in the present disclosure, including any of the features described above in relation to the devices and methods, as well as any of the following features.

The controller may further be configured to determine operating conditions for the oxygen delivery device based on the patient's tidal volume and the required FiO2, and further based on one or more of, for example, respiratory rate for the patient, oxygen purity value of the oxygen delivered to the patient, and/or Inspiration:Expiration (I:E) ratio.

The operating conditions include one or more of, for example, speed of the gas moving device providing an air flow to the oxygen delivery module, oxygen delivery module cycle speed, and/or desired oxygen purity level to be produced by the oxygen delivery device.

The controller configured to determine operating conditions may be configured to determine optimal operating conditions that would result in reduced energy consumption for the system.

The device may further include one or more of, for example, a pressure sensor to determine a pressure level produced by oxygen delivery device, a gas moving device providing an air flow to the oxygen delivery module, and/or a purity sensor to determine oxygen purity value produced by the oxygen delivery device.

In yet another aspect, a method is disclosed. The method includes receiving data representative of at least a patient's tidal volume data indicative of normal volume of air displaced between inspiration and expiration by the patient, and data representative of a fraction of inspired oxygen (FiO2) value required for the patient, and controlling an oxygen delivery module producing at least concentrated oxygen to cause the oxygen delivery module to deliver oxygen to the patient based at least on the patient's tidal volume data and the FiO2 value.

Embodiments of the method may include any of the features described in the present disclosure, including any of the features described above in relation to the devices and methods.

In another aspect, an oxygen delivery device is disclosed. The oxygen delivery device includes an oxygen delivery module, at least one sensor to detect patient breathing, and a controller configured to control the oxygen delivery module to cause the oxygen delivery module to deliver oxygen to the patient based on data from the at least one sensor such that in response to a determination, based on data from the at least one sensor, that no breathing is detected for a first pre-determined period of time, the controller causes the oxygen delivery module to deliver oxygen to the patient in continuous flow mode, and in response to a determination, based on additional data from the at least one sensor, that breathing is detected for a second period of time, the controller causes the oxygen delivery module to deliver oxygen to the patient in a pulse flow mode.

Embodiments of the device may include any of the features described in the present disclosure, including any of the features described above in relation to the devices and methods, as well as any one of the following features.

The at least one sensor may be configured to detect patient breathing by performing one of, for example, continuous detection of patient breathing, and/or periodic detection of patient breathing.

The controller may further be configured, subsequent to the determination that no breathing is detected and to causing the oxygen delivery module to deliver oxygen to the patient in continuous flow mode, to terminate the continuous flow delivery of oxygen to the patient, and cause the oxygen delivery module to deliver oxygen to the patient in pulse dose mode in response to one or more of, for example, a determination that a second pre-determined period of time has elapsed since the determination that no breathing is detected, and the determination, based on the additional data from the at least one sensor, that the patient is breathing.

The at least one sensor may include a pressure sensor fluidly connected to a cannula coupled to the oxygen delivery module, the cannula structured to deliver the oxygen from the oxygen delivery module through the patient's nasal passages.

The pressure sensor fluidly connected to the cannula may be configured to detect pressure changes within the patient's nasal passages, and to generate data representative of the pressure changes.

The controller may further be configured to receive a feed of the data generated by the pressure sensor, and perform filtering operation on the feed of the data generated by the pressure sensor to determine onset of an inspiratory cycle for the patient.

In an additional aspect, a method is disclosed. The method includes receiving information regarding patient breathing, and controlling oxygen delivery to a patient by causing an oxygen delivery module to deliver oxygen to the patient in continuous mode flow in response to a determination, based on the received information, that no patient breathing is detected for a first pre-determined period of time and in response to a determination, based on data from the at least one sensor, that breathing is detected for a second period of time, the controller causes the oxygen delivery module to deliver oxygen to the patient in a pulse flow mode.

Embodiments of the method may include any of the features described in the present disclosure, including any of the features described above in relation to the devices and methods, as well as any of the following features.

Controlling the oxygen delivery may include, subsequent to causing the oxygen delivery module to deliver oxygen to the patient in continuous flow mode in response to the determination that no breathing is detected, terminating the continuous flow delivery of oxygen to the patient, and causing the oxygen delivery module to deliver oxygen to the patient in pulse dose mode in response to one or more of, for example, determining that a second pre-determined period of time has elapsed since the determination that no breathing is detected, and/or determining, based on additionally received information, that the patient is breathing.

In another aspect, an oxygen delivery device is disclosed. The oxygen delivery device includes an oxygen delivery module, and one or more sensors to determine data representative of one or more of environmental conditions, operating conditions of the oxygen delivery device, and patient's characteristics. The oxygen delivery device also includes a controller to control, based at least in part on the determined data, at least the oxygen delivery module's operations, and a display module to present information based, at least in part, on the data representative of the characteristics of the patient.

Embodiments of the device may include any of the features described in the present disclosure, including any of the features described above in relation to the devices and methods, as well as any one of the following features.

The one or more sensors may include one or more of, for example, an electroencephalogram, an electrooculogram, an electrocardiogram, an actigraph, a pedometer, a pulse oximeter, an accelerometer, a pressure sensor, a flow sensor, a purity sensor, a clock, and/or a timer.

The display module may include a touch screen.

The display module may include discrete buttons adjacent to a display area.

The information presented may include one or more of, for example, patient's sleep state, patient's respiratory rate, inspiratory:expiratory time ratio, ambulation time, activity level, oxygen saturation, total oxygen delivered, heart rate, oxygen delivered per period of time, hours of usage, and/or usage time. The information displayed may further include trends of the available information.

The oxygen delivery device may further include a communication module to communicate data to a remote location using one or more of, for example, a wireless communication link, and/or a wired-based communication link.

In a further aspect, an oxygen delivery device is disclosed. The device includes an oxygen delivery module, one or more sensors to determine data representative of one or more of, for example, environmental conditions, operating conditions of the oxygen delivery device, and/or patient's characteristics, a controller to control, based at least in part on the determined data, at least the oxygen delivery module's operations, and an identification module to receive information representative of an identity of a user and to compare the received information to stored data uniquely identifying a patient associated with the oxygen delivery device.

Embodiments of the device may include any of the features described in the present disclosure, including any of the features described above in relation to the devices and methods, as well as any one of the following features.

The identification module may include one or more of, for example, an alpha-numeric keypad, an iris scanner, a magnetic stripe card, a barcode scanner, a fingerprint scanner, a facial feature recognition device, and/or a palm scanner.

The controller may associate patient identification with data collected by the one or more sensors.

Data collected by the one or more sensors may be used to compute one or more of, for example, sleep state, respiratory rate, inspiratory:expiratory time ratio, ambulation time, activity level, oxygen saturation, total oxygen delivered, heart rate, oxygen delivered per period of time, hours of usage, and/or usage time.

In another aspect, an oxygen delivery device is disclosed. The device includes an oxygen delivery module, one or more sensors to determine data representative of one or more of, for example, environmental conditions, operating conditions of the oxygen delivery device, and/or patient's characteristics, a controller to control, based at least in part on the determined data, at least the oxygen delivery module's operations, and an identification module to receive information representative of an identity of a user and to compare the received information to stored data uniquely identifying a patient associated with the portable oxygen delivery device. The device also includes a display module to present information based, at least in part, on data determined by the one or more sensors.

Embodiments of the device may include any of the features described in the present disclosure, including any of the features described above in relation to the devices and methods, as well as any of the following features.

The information displayed may further include trends of the available information.

The controller may associate patient identification with data collected by the one or more sensors.

The controller may further be configured to compare the determined data representative of the one or more of, for example, the environmental conditions, the operating conditions of the oxygen delivery device, and/or the patient's characteristics, to respective pre-determined threshold values representative of one or more of normal environmental conditions, normal operating conditions of the oxygen delivery device, and normal patient's characteristics, and communicate an alert in response to a determination that at least one of the determined data representative of the one or more of the environmental conditions, the operating conditions of the oxygen delivery device, and the patient's characteristics, deviates from a respective at least one of the pre-determined threshold values representative of one or more of normal environmental conditions, normal operating conditions of the oxygen delivery device, and normal patient's characteristics.

The display device may be configured to present information based, at least in part, on the data determined by the one or more sensors in response to a determination by the identification module that the data determined by the one or more sensor corresponds to the patient identified by the identification module.

In yet another aspect, an oxygen delivery device is disclosed. The oxygen delivery device includes an oxygen delivery module configured to deliver a pulse including greater than 100 mL of concentrated oxygen, and a controller configured to control the oxygen delivery module to cause the oxygen delivery module to deliver the pulse including greater than the 100 mL of the concentrated oxygen within approximately first 60% of a patient's inspiratory period.

Embodiments of the device may include any of the features described in the present disclosure, including any of the features described above in relation to the devices and methods, as well as any of the following features.

The oxygen delivery device may further includes at least one sensor to detect patient breathing. The controller is configured to control the oxygen delivery module to cause the oxygen delivery module to deliver the pulse of the at least 100 mL of concentrated oxygen upon a determination, based on data received from the at least one sensor, that the patient's inspiratory cycle has commenced. The at least one sensor may include a pressure sensor fluidly connected to a cannula coupled to the oxygen delivery module, the cannula structured to deliver the oxygen from the oxygen delivery module through the patient's nasal passages. The pressure sensor fluidly connected to the cannula may be configured to detect pressure changes within the patient's nasal passages, and to generate data representative of the detected pressure changes.

The controller may further be configured to receive a feed of the data generated by the at least one sensor, and to perform filtering operation on the feed of the data generated by the at least one sensor to determine onset of an inspiratory cycle for the patient.

The oxygen delivery module configured to deliver the pulse greater than 100 mL may be configured to deliver a pulse of between 100 mL and 270 mL of concentrated oxygen.

In an additional aspect, a method is disclosed. The method includes controlling an oxygen delivery module to cause the oxygen delivery module to deliver a pulse greater than 100 mL of concentrated oxygen, and delivering by the oxygen delivery module the pulse including greater than 100 mL of concentrated oxygen within approximately first 60% of a patient's inspiratory period.

Embodiments of the method may include any of the features described in the present disclosure, including any of the features described above in relation to the devices and methods.

In a further aspect, an oxygen delivery device is disclosed. The oxygen delivery device includes an oxygen delivery module to provide at least concentrated oxygen, a piezoelectric valve coupled to an output of the oxygen delivery module to receive the produced concentrated oxygen, a driver to electrically actuate the piezoelectric valve, and a controller to control the driver to cause controllable actuation of the piezoelectric valve by the driver so as to cause controllable opening of the valve to enable flow of oxygen delivered by the oxygen delivery module to be directed for inhalation by a patient via the piezoelectric valve.

Embodiments of the device may include any of the features described in the present disclosure, including any of the features described above in relation to the devices and methods, as well as any of the following features.

The oxygen delivery device may further include one or more sensors to determine data representative of one or more of, for example, environmental conditions, operating conditions of the oxygen delivery device, and/or the patient's therapeutic conditions. The controller configured to control the driver to cause controllable actuation of the piezoelectric valve may be configured to control the driver to cause controllable actuation of the piezoelectric valve based, at least in part, on the determined data from the one or more sensors representative of the one or more of environmental conditions, operating conditions of the oxygen delivery device, and patient's therapeutic conditions.

In another aspect, a method is disclosed. The method includes determining data representative of one or more of environmental conditions, operating conditions of an oxygen delivery device, and a patient's therapeutic conditions, and controlling a driver actuating a piezoelectric valve coupled to an output of an oxygen delivery module of an oxygen delivery device based, at least in part, on the determined data from the one or more sensors representative of the one or more of the environmental conditions, the operating conditions of the oxygen delivery device, and the patient's therapeutic conditions, to cause controllable opening of the valve to enable flow of oxygen delivered by the oxygen delivery module to be directed for inhalation by the patient via the piezoelectric valve.

Embodiments of the method may include any of the features described in the present disclosure, including any of the features described above in relation to the devices and methods.

In yet a further aspect, an oxygen delivery device is disclosed. The oxygen delivery device includes an oxygen delivery module to produce at least concentrated oxygen, and a gas moving device to deliver air to the oxygen delivery module. The gas moving device includes at least one piston rotatable inside a first chamber defined in a housing, the rotational movement of the at least one piston inside the first chamber resulting in varying pressure generated in a first portion of the first chamber, and a vane member rigidly coupled to the at least one piston, the vane member being configured to move inside a vane chamber defined in the housing. The piston and the vane rigidly coupled to the piston define the first portion of the first chamber and a second portion of the first chamber.

Embodiments of the device may include any of the features described in the present disclosure, including any of the features described above in relation to the devices and methods, as well as any one of the following features.

The at least one rotatable piston may define a radial clearance between tangential surfaces of the at least one rotatable piston and the first chamber wall surface, the clearance being less than or equal to 50 microns.

The varying pressure resulting in the first chamber may be represented as a first periodic function of the pressure generated in the first portion of the first chamber.

The gas moving device may be configured as one or more of, for example, a compressor, and/or a vacuum pump.

The oxygen delivery device may further include at least one additional gas moving device. Each of the additional gas moving device may include a corresponding additional piston rotating inside a corresponding bore chamber defined in the housing, the rotational movement of the corresponding additional piston inside the corresponding bore chamber resulting in corresponding pressure represented as a corresponding additional periodic function created in a corresponding portion of the corresponding bore chamber. The each of the additional gas moving device may include a corresponding additional vane member coupled to the corresponding additional piston, the corresponding additional vane being configured to move inside a corresponding additional vane chamber defined in the housing.

The at least one additional gas moving device may include two, three, or four gas moving devices. The at least one additional gas moving device may all be driven by a single rotary power source.

Forces resulting from the rotational movement of the at least one piston in the first chamber may destructively interfere with forces resulting from the rotational movement of the corresponding additional piston of each of the at least one additional gas moving device in the corresponding bore chamber, such that net forces created in the oxygen delivery device are reduced.

The housing may include axially separated surfaces, and one or more endplates effectively sealing the first chamber. The at least one piston may include a cylindrical piston with an exterior diameter, the cylindrical piston being operatively associated with a drive member disposed within the first chamber and rotatable therein, and further being offset with respect to a centerline of the first chamber portion such that the exterior diameter of the piston is in close proximity to bounds of the first chamber portion during orbit of the piston, to divide the first chamber into a suction chamber portion and a compression chamber portion.

The oxygen delivery device may have a weight of between 2-15 pounds.

The at least one piston rotating inside the first chamber of the housing may include a first piston rotating inside the first chamber to facilitate compression operations, and a second, separate piston rotating inside a second chamber defined in the housing to facilitate vacuum pump operations. Compressor pressure generated in the first chamber may be represented as a first sinusoidal function, and pressure formed in the second chamber may be represented as a second sinusoidal function that is approximately 180° out of phase relative to the first sinusoidal function. The relative radial position of the first piston in the first chamber may be represented as a first periodic function, and the relative radial position of the second piston in the second chamber may be represented as a second periodic function that is out of phase in relation to the first periodic function.

Forces resulting from the rotational movement of the first piston in the first chamber may destructively interfere with forces resulting from the rotational movement of the second piston in the second chamber such that net forces created in the oxygen delivery device are reduced.

In another aspect, a method is disclosed. The method includes supplying air to a gas moving device configured to deliver compressed air to an oxygen delivery module of an oxygen delivery device, actuating at least one piston rotatable inside a first chamber defined in the housing of the gas moving device, the rotational movement of the at least one piston inside the first chamber resulting in varying pressure generated in a first portion of the first chamber. The at least one piston is rigidly coupled to a vane member configured to move inside a vane chamber defined in the housing, the piston and the vane rigidly coupled to the piston define the first portion of the first chamber and a second portion of the first chamber. The method also includes directing pressured air from the first chamber to the oxygen delivery module.

Embodiments of the method device may include any of the features described in the present disclosure, including any of the features described above in relation to the devices and methods, as well as any of the following features.

Actuating the at least one piston rotatable inside the first chamber may include actuating a first piston rotatable inside the first chamber configured to operate as a compressor to draw ambient air into the oxygen delivery module, the rotational movement of the at least one piston inside the first chamber resulting in compressor pressure created in the first chamber that is represented as a first periodic function, and may also includes actuating a second piston inside a second chamber of the housing, the second chamber configured to operate as a vacuum pump to draw exhaust gas from the oxygen delivery module, the rotational movement of the second piston inside the second chamber resulting in vacuum pump pressure created in the second chamber that is represented as a second periodic function. The first periodic function representative of the compressor pressure inside the first chamber may be approximately 180° out of phase relative to the second periodic function representative of the vacuum pump pressure created inside the second chamber such that forces resulting from the rotational movement of the first piston in the first chamber destructively interfere with forces resulting from the rotational movement of the second piston in the second chamber.

In an additional aspect, an oxygen delivery device is disclosed. The oxygen delivery device includes an oxygen delivery module to produce at least concentrated oxygen, a first gas moving device to deliver air to the oxygen delivery module, the first gas moving device being driven by a first motor to actuate the gas moving device to run at variable speeds. The device also includes a second gas moving device to draw exhaust gas from the oxygen delivery module, the second gas moving device being driven by a second motor, separate from the first motor, to actuate the second gas moving device to run at variable speeds.

Embodiments of the device may include any of the features described in the present disclosure, including any of the features described above in relation to the devices and methods, as well as any of the following features.

The oxygen delivery device may further include at least one sensor to determine data representative of one or more of, for example, environmental conditions, operating conditions of the oxygen delivery device, and/or patient's therapeutic conditions. The device may also include at least one controller to control the speeds of at least one of the first gas moving device and the second gas moving device by controlling operations of at least the first motor and the separate second motor based on the determined data.

The determined data may include data representative of one or more of, for example, oxygen flow, ambient pressure, ambient temperature, and/or required oxygen purity.

In a further aspect an oxygen delivery device is disclosed. The oxygen delivery device includes an oxygen delivery module, at least one sensor to determine at least one environmental condition in which the portable oxygen delivery device is operating, and a controller to control, based on the determined at least one environmental condition, at least the oxygen delivery module's operations to cause a specified therapeutic requirement for the patient to be achieved.

Embodiments of the device may include any of the features described in the present disclosure, including any of the features described above in relation to the devices and methods, as well the following features.

The at least one sensor may be configured to determine one or more of, for example, ambient temperature, and/or altitude.

In another aspect, an oxygen delivery device is disclosed. The oxygen delivery device includes an oxygen delivery module to produce at least concentrated oxygen, a first gas moving device to deliver air to an oxygen delivery module, the first gas moving device being driven by a first motor to actuate the gas moving device to run at variable speeds. The device also includes a second gas moving device to draw exhaust gas from the oxygen delivery module, the second gas moving device being driven by a second motor, separate from the first motor, to actuate the second gas moving device to run at variable speeds, a purity sensor to determine oxygen purity value produced by the oxygen delivery module, and a controller to control speeds of the first and second gas moving devices by controlling operations of at least the first motor and the separate second motor, based at least in part on the determined oxygen purity value, to cause the purity level of the oxygen produced by the oxygen delivery module to be substantially at a pre-determined purity value.

Embodiments of the device may include any of the features described in the present disclosure, including any of the features described above in relation to the devices and methods, as well as the following features.

The pre-determined purity value may be the minimum acceptable oxygen purity level to enable energy consumption of the system to be reduced, the pre-determined purity value having a value of between approximately 82% and approximately 93% of oxygen.

In an additional aspect, an oxygen delivery device is disclosed. The oxygen delivery device includes an oxygen delivery module to produce at least concentrated oxygen, and a controller to control at least some operations of the oxygen delivery device, including controlling operation affecting operations of the oxygen delivery module, the controller configured to enable the activation of one or more of a plurality of operational modes supported by the oxygen delivery device. The controller includes at least one processor based device, and at least one non-transitory memory storage device to store computer instructions, the computer instructions including instructions that when executed on the at least one processor-based device cause the at least one processor-based device to receive data indicative of one or more operational modes from the plurality of operational modes that are to be activated, and in response to the received data, enabling the one or more operational modes of the oxygen delivery device that are to be activated.

Embodiments of the device may include any of the features described in the present disclosure, including any of the features described above in relation to the devices and methods, as well as any of the following features.

The computer instructions that cause the at least one processor-based device to receive the data indicative of the one or more operational modes may include further instructions that further cause the at least one processor-based device to receive data indicative of at least one active operational mode that is to be disabled.

The controller may be configured to cause the oxygen delivery device to operate in a default generic mode when all other of the plurality of operational modes are not active.

In yet a further aspect, a method is disclosed. The method includes receiving data indicative of one or more operational modes, from a plurality of operational modes supported by an oxygen delivery device, that are to be activated, enabling the operational modes that are to be activated based on the received data, and controlling at least some operations of the oxygen delivery device, including controlling operation affecting operations of an oxygen delivery module to produce at least concentrated oxygen, based on the enabled operational modes.

Embodiments of the method device may include any of the features described in the present disclosure, including any of the features described above in relation to the devices and methods.

In an additional aspect, an oxygen concentrator system is disclosed. The system includes a cart, and an oxygen delivery device placed on the cart. The oxygen delivery device includes an oxygen delivery module, at least one sensor to measure data representative of at least one patient characteristic, the at least one sensor being secured to the cart. The oxygen delivery device further includes a controller to receive the measured data and monitor the at least one patient characteristic based on the received measured data.

Embodiments of the system may include any of the features described in the present disclosure, including any of the features described above in relation to the devices and methods, as well as any of the following features.

The at least one sensor may be secured to a handle of the cart such that the at least one sensor is configured to measure the data representative of the at least one patient characteristic while the patient is grasping the handle.

The at least one sensor may include one or more of, for example an oximeter to measure the patient's SpO2 level, and/or a pedometer to measure the patient's activity level.

The controller may further be configured to compare the measured data representative of the at least one patient characteristic to a respective at least one pre-determined threshold value representative of normal values for the corresponding at least one patient characteristic, and communicate an alert in response to a determination that the measured data representative of the at least one patient characteristic deviates from the respective at least one pre-determined threshold value representative of the normal values corresponding at least one patient characteristic.

In another aspect, a method is disclosed. The method includes measuring data representative of at least one patient characteristic using at least one sensor secured to a cart on which an oxygen delivery device is placed, receiving the measured data representative of the at least one patient characteristic, and monitoring the at least one patient characteristic based on the received measured data.

Embodiments of the method may include any of the features described in the present disclosure, including any of the features described above in relation to the devices, system, and methods, as well as any of the following features.

In another aspect, a respiratory device is disclosed. The respiratory device includes an oxygen delivery device including an oxygen delivery module to produce at least concentrated oxygen, and a gas moving device to deliver air to the oxygen delivery module, the gas moving device being driven by a motor to actuate the gas moving device. The respiratory device also includes a nebulizer containing liquid medication for a patient that is stored in a medication chamber defined within the nebulizer, the nebulizer being coupled to the oxygen delivery device such that the concentrated oxygen produced by the oxygen delivery module is directed into the inner medication chamber of the nebulizer to convert at least some of the liquid medication into aerosol medication. At least some of the concentrated oxygen directed into the nebulizer and the at least some of the converted aerosol medication are delivered for inhalation by a patient through a nebulizer outlet port.

Embodiments of the device may include any of the features described in the present disclosure, including any of the features described above in relation to the devices, system, and methods, as well as any of the following features.

The nebulizer may be coupled to the oxygen delivery module through a tubing connecting the nebulizer to an outlet of the oxygen delivery device through which the oxygen produced by the oxygen delivery module is delivered.

The nebulizer may include a jet nebulizer configured to use the concentrated oxygen directed into the nebulizer at high velocity as a gas source to cause the liquid medication to be concerted to aerosol.

The liquid medication may include one or more of, for example, liquid medication to treat cystic fibrosis, liquid medication to treat asthma, and/or liquid medication to treat other respiratory diseases.

In an additional aspect, a method is disclosed. The method includes producing concentrated oxygen using an oxygen delivery device including an oxygen delivery module to produce at least the concentrated oxygen, and a gas moving device to deliver air to the oxygen delivery module, converting at least some of liquid medication contained in a medication chamber of a nebulizer into aerosol medication by directing the concentrated oxygen produced by the oxygen delivery module into the nebulizer, and delivering at least some of the concentrated oxygen directed into the nebulizer and at least some of the converted aerosol medication for inhalation by a patient through a nebulizer outlet port.

Embodiments of the method may include any of the features described in the present disclosure, including any of the features described above in relation to the devices, system, and methods.

In a further aspect, an oxygen delivery device is disclosed. The oxygen delivery device includes an oxygen delivery device including an oxygen delivery module to produce at least concentrated oxygen, and a gas moving device to deliver air to the oxygen delivery module, the gas moving device being driven by a motor to actuate the gas moving device. The device also includes a container holding fluid, the container being coupled to the oxygen delivery device such that the concentrated oxygen produced by the oxygen delivery module is directed into the container to be passed through the fluid so as to entrain at least some fluid vapor. At least some of the concentrated oxygen directed into the container and the fluid vapor are delivered for inhalation by a patient through an outlet of the container.

Embodiments of the device may include any of the features described in the present disclosure, including any of the features described above in relation to the devices, system, and methods, as well as any one of the following features.

The container may be coupled to the oxygen delivery device through a tubing connecting the container to an outlet of the oxygen delivery device through which the oxygen produced by the oxygen delivery module is delivered.

The fluid in the container may include scented fluid. The entrained fluid vapor may include entrained scented fluid vapor used to perform one or more of, for example, encouraging patient compliance with oxygen therapy, providing respiratory disinfection, providing decongestion, providing expectoration, and/or providing beneficial psychological treatment to the patient.

The fluid in the container may include water. The entrained fluid vapor may include entrained water vapor to facilitate humidifying functionality.

In yet another aspect, a method is disclosed. The method includes producing concentrated oxygen using an oxygen delivery device including an oxygen delivery module to produce at least the concentrated oxygen, and a gas moving device to deliver ambient air to the oxygen delivery module. The method also includes directing the concentrated oxygen through fluid in a container to entrain at least some of fluid into fluid vapor, and delivering at least some of the concentrated oxygen directed into the fluid container and the entrained fluid vapor for inhalation by a patient through an outlet of the container.

Embodiments of the method may include any of the features described in the present disclosure, including any of the features described above in relation to the devices, system, and methods, as well as the following feature.

The fluid may include one of, for example, scented fluid, and/or water.

In another aspect, an oxygen delivery device is disclosed. The device includes an oxygen delivery module to produce at least concentrated oxygen, the oxygen delivery module including one or more adsorbent beds configured to selectively adsorb corresponding materials from fluid directed through the one or more adsorbent beds, a rotary valve for selectively transferring the fluid through the one or more adsorbent beds, and one or more position sensors to determine a value representative of the rotational position of the rotary valve. The device further includes a controller configured to, in response to termination of operation of the oxygen delivery module, cause actuation of the rotary valve, based on the data determined by the one or more position sensors, to rotate the rotary valve to a position where passages between ambient air and the one or more adsorbent beds are closed so as to prevent atmospheric moisture from reaching the one or more adsorbent beds.

Embodiments of the device may include any of the features described in the present disclosure, including any of the features described above in relation to the devices, system, and methods, as well as any of the following features.

The one or more position sensors may include at least one of, for example, a rotary encoder, and/or a shaft position indicator. The one or more position sensors may be placed proximate one or more of, for example, the rotary valve, and/or a shaft coupled to the rotary valve.

The rotary valve may include a rotary valve shoe and a valve port plate having respective engaged surfaces and the rotary valve shoe rotatable to provide valving action for selectively transferring fluids therethrough, the rotary valve shoe including multiple passages allowing fluid to flow therethrough, and a fluid distribution manifold to distribute fluids between the adsorption beds and the valve members, the fluid distribution manifold including multiple passages allowing fluid to flow therethrough. The rotary valve may also includes one or more passages of at least one of the rotary valve shoe and the fluid distribution manifold including one or more purge passages having a distinct flow control element disposed therein other than the at least one or more passages of at least one of the rotary valve shoe and the fluid distribution manifold to allow for precise control of purge fluid therethrough to improve pressure swing adsorption system performance.

In a further aspect, a method is disclosed. The method includes determining rotary position of a rotary valve for an oxygen delivery module using one or more position sensors, the rotary valve configured to selectively transfer fluid through the one or more adsorbent beds that selectively adsorb corresponding materials from the fluid. In response to termination of operation the oxygen delivery module, controllably actuating the rotary valve, based on the data determined by the one or more position sensors, to rotate the rotary valve to a position where passages between ambient air and the one or more adsorbent beds are closed so as to prevent atmospheric moisture from reaching the one or more adsorbent beds.

Embodiments of the method may include any of the features described in the present disclosure, including any of the features described above in relation to the devices, system, and methods.

In another aspect, an oxygen delivery device is disclosed. The oxygen delivery device includes an oxygen delivery module, at least one sensor to determine data representative of performance degradation of one or more filters used with the oxygen delivery device, and a controller to alert, based on the determined data representative of the performance degradation of the one or more filters, that performance of at least one of the one or more filters has degraded.

Embodiments of the device may include any of the features described in the present disclosure, including any of the features described above in relation to the devices, system, and methods, as well as any of the following features.

The one or more filters may include an intake filter to filter ambient air drawn into a gas moving device, wherein the at least one sensor is configured to determine pressure differential across the intake filter. The controller may be configured to alert that performance of the at least one of the one or more filters has degraded is configured to alert that the performance of the intake filter has degraded in response to a determination that the determined pressure differential across the intake filter exceeds a pre-determined pressure differential threshold.

In an additional aspect, a method is disclosed. The method includes measuring pressure differential across an intake filter configured to filter ambient air drawn into a gas moving device, determining whether the measured pressure differential across the intake filter exceeds a pre-determined pressure differential threshold, and alerting that performance of the intake filter had degraded in response to a determination that the measured pressure differential across the intake filter exceeds the pre-determined pressure differential threshold.

Embodiments of the method may include any of the features described in the present disclosure, including any of the features described above in relation to the devices, system, and methods.

In yet a further aspect, an oxygen delivery device is disclosed. The oxygen delivery device includes an oxygen delivery module to produce at least concentrated oxygen, and a controller to perform one or more of controlling at least some operations of the oxygen delivery device, identifying problems associated with the oxygen delivery device, resolving the identified problems associated with the oxygen delivery device, and calibrating the oxygen delivery device. The controller includes at least one processor based device, and at least one non-transitory memory storage device to store computer instructions, the computer instructions including instructions that when executed on the at least one processor-based device cause the at least one processor-based device to receive data representative of operation of the oxygen delivery device; and determine automatically problems associated with the operations of the oxygen delivery device based on the received data.

Embodiments of the device may include any of the features described in the present disclosure, including any of the features described above in relation to the devices, system, and methods, as well as any of the following features.

The computer instructions that cause the at least one processor based device to determine automatically problems associated with the operations of the oxygen delivery device may include instructions that cause the at least one processor-based device to determine automatically problems associated with the operations of the oxygen delivery device using an expert system learning engine.

The instructions may further include instruction to further cause the at least one processor based device to automatically determine data to controllably change one or more operation parameters of the oxygen delivery device to cause a change in the operation of the respiratory care device, and change the operation parameters of the oxygen delivery device according to the determined data.

In an additional aspect, an oxygen delivery device is disclosed. The oxygen delivery device includes an oxygen delivery module to produce at least concentrated oxygen, and a tracking device coupled to the oxygen delivery device to enable determining geographical location of the oxygen delivery device. The tracking device includes one or more of, for example, a) a WiFi-based geolocation device including a wireless receive configured to determine availability of WiFi-based network routers in the vicinity of the oxygen delivery device, and to communicate with one or more of the WiFi-based network routers available in the vicinity of the oxygen delivery device, wherein an approximation of the geographical location of the oxygen delivery device is determined based on location data associated with the one or more WiFi-based network routers communicating with the oxygen delivery device, b) a GPS-based tracking device to receive GPS signals from one or more satellite, determine approximate position of the GPS-tracking device based on the received GPS signals, and communicate to a remote location data representative of the determined the approximate position of the GPS-tracking device, and c) a device to monitor use of the oxygen delivery device, and to cause an alarm to be activated in response to a determination that the oxygen delivery device was not used for at least a pre-determined period of time.

Embodiments of the device may include any of the features described in the present disclosure, including any of the features described above in relation to the devices, system, and methods, as well as the following features.

The device to monitor use of the oxygen delivery device may include a PC board mounted within the oxygen delivery device.

In a further aspect, an oxygen delivery device is disclosed. The oxygen delivery device includes an oxygen delivery module to produce at least concentrated oxygen, at least one sensor to determine data representative of one or more of environmental conditions, operating conditions of the oxygen delivery device, and patient's therapeutic conditions, and a controller. The controller is configured to communicate the determined data to a remote station to facilitate determining values of operation parameters controlling operation of the oxygen delivery device based on, at least in part, the communicated data representative of the one or more of the environmental conditions, the operating conditions of the oxygen delivery device, and the patient's therapeutic conditions, receive from the remote station data representative of the values of the operation parameters controlling operation of the oxygen delivery device, and adjust the operation parameters of the oxygen delivery device based on the data received from the remote station.

Embodiments of the device may include any of the features described in the present disclosure, including any of the features described above in relation to the devices, system, and methods.

In another aspect, a method is disclosed. The method includes determining data representative of one or more of environmental conditions, operating conditions of an oxygen delivery device comprising an oxygen delivery module to produce at least concentrated oxygen, and patient's therapeutic conditions, and communicating the determined data to a remote station to facilitate determining values of operation parameters controlling operation of the oxygen delivery device based on, at least in part, the communicated data representative of the one or more of the environmental conditions, the operating conditions of the oxygen delivery device, and the patient's therapeutic conditions. The method also includes receiving from the remote station operation parameter data representative of the values of the operation parameters to control operation of the oxygen delivery device, and adjusting the operation parameters of the oxygen delivery device based on the data received from the remote station.

Embodiments of the method may include any of the features described in the present disclosure, including any of the features described above in relation to the devices, system, and methods.

In yet another aspect, an oxygen delivery device is disclosed. The oxygen delivery device includes an oxygen delivery module to produce at least concentrated oxygen, a purity sensor to determine oxygen purity value produced by the oxygen delivery module, one or more device sensors to monitor the operation of the oxygen delivery device, and a controller. The controller is configured to receive data from the purity sensor and the one or more device sensors, determine, based on the data received from the one or more device sensors, whether an operational problem condition exists in relation to the operation of the oxygen delivery device, and in response to a determination that a problem condition exists in relation to the operation of the oxygen delivery device, cause at least partial operation of the oxygen delivery device to be maintained upon a further determination, based on the data received from the purity sensor, that the oxygen purity level exceeds a pre-determined minimum purity threshold.

Embodiments of the device may include any of the features described in the present disclosure, including any of the features described above in relation to the devices, system, and methods, including any of the following features.

The pre-determined minimum purity threshold may be 21%.

The controller may be configured to cause the at least partial operation of the oxygen delivery device to be maintained is configured to cause a change from an operation mode that was active before the determination that a problem condition exists to another operational mode for the oxygen delivery device.

In an additional aspect, a method is disclosed. The method includes receiving data from a purity sensor representative of the oxygen purity level of oxygen produced by an oxygen delivery module of an oxygen delivery device, receiving data from one or more device sensors monitoring the operation of the oxygen delivery device, determining, based on the data received from the one or more device sensors, whether an operational problem condition exists in relation to the operation of the oxygen delivery device, and in response to a determination that a problem condition exists in relation to the operation of the oxygen delivery device, causing at least partial operation of the oxygen delivery device to be maintained upon a further determination, based on the data received from the purity sensor, that the oxygen purity level exceeds a pre-determined minimum purity threshold.

Embodiments of the method may include any of the features described in the present disclosure, including any of the features described above in relation to the devices, system, and methods.

In a further aspect, an oxygen delivery device is disclosed. The oxygen delivery device includes an oxygen delivery module to produce at least concentrated oxygen, a gas moving device to deliver the ambient air to the oxygen delivery module, a stepper motor comprising one or more electromagnetic coils arranged around a gear element, the stepper motor configured to drive at least the gas moving device, and a controller configured to modulate the driving signals used to energize the one or more electromagnetic coils to achieve a specified slew rate so as to reduce the vibration and structural noise emanating from the stepper motor without loss of efficiency.

Embodiments of the device may include any of the features described in the present disclosure, including any of the features described above in relation to the devices, system, and methods.

In yet another aspect, an oxygen delivery device is disclosed. The oxygen delivery device includes an oxygen delivery module to produce at least concentrated oxygen, the oxygen delivery module including one or more adsorbent beds configured to selectively adsorb corresponding materials from fluid directed through the one or more adsorbent beds, a rotary valve for selectively transferring the fluid through the one or more adsorbent beds, the rotary valve including an index indicator detectable by a sensor, and one or more sensors to detect the indexing indicator on the rotary valve. The oxygen delivery device further includes a controller configured to determine from information relating to the indexing indicator detected by the one or more sensors at least one of: rotational position of rotary valve, and number of rotation cycles completed by the rotary valve during a pre-determined period of time.

Embodiments of the device may include any of the features described in the present disclosure, including any of the features described above in relation to the devices, system, and methods, including any one of the following features.

The controller may be further configured to cause actuation of the rotary valve, based on the rotational position of the rotary valve determined from the information relation to the detected indexing indicator, to rotate the rotary valve to a position where passages between ambient air and the one or more adsorbent beds are closed so as to prevent atmospheric moisture from reaching the one or more adsorbent beds.

The rotary valve may include a rotary valve shoe and a valve port plate having respective engaged surfaces and the rotary valve shoe rotatable to provide valving action for selectively transferring fluids therethrough, the rotary valve shoe including multiple passages allowing fluid to flow therethrough, a fluid distribution manifold to distribute fluids between the adsorption beds and the valve members, the fluid distribution manifold including multiple passages allowing fluid to flow therethrough, and one or more passages of at least one of the rotary valve shoe and the fluid distribution manifold including one or more purge passages having a distinct flow control element disposed therein other than the at least one or more passages of at least one of the rotary valve shoe and the fluid distribution manifold to allow for precise control of purge fluid therethrough to improve pressure swing adsorption system performance.

The sensor may include a switch configured to be activated when the indexing indicator passes the switch, and to generate a signal to the controller indicative that the indexing indicator has passed the switch.

The switch may include one or more of, for example, an optical switch to optically detect the indexing indicator when the indexing indicator passes by the optical switch, and/or a mechanical switch configured to be mechanically activated upon mechanical actuation of the switch by the indexing indicator.

In a further aspect, a method is disclosed. The method includes detecting an indexing indicator included on a rotary valve for an oxygen delivery module using one or more sensors, the rotary valve configured to selectively transfer fluid through the one or more adsorbent beds that selectively adsorb corresponding materials from the fluid, and determining based on information relating to the indexing indicator detected by the one or more sensors at least one of, for example, rotational position of rotary valve, and/or number of rotation cycles completed by the rotary valve during a pre-determined period of time.

Embodiments of the method may include any of the features described in the present disclosure, including any of the features described above in relation to the devices, system, and methods.

In an additional aspect, an oxygen delivery device is disclosed. The device includes an oxygen delivery module to produce at least concentrated oxygen, a gas moving device to deliver the ambient air to the oxygen delivery module, a fan to cool the oxygen delivery device, at least one temperature sensor, and one or more sensors to determine data representative of one or more of environmental conditions, operating conditions of the oxygen delivery device, and a patient's therapeutic conditions, including at least one temperature sensor to measure temperature of the oxygen delivery device. The oxygen delivery device further includes a controller to control operation of the fan based on the data determined by the one or more sensors, including the temperature measured by the temperature sensor, to control the fan to cause the temperature of the oxygen delivery device to be at an optimal temperature at which power consumption of the oxygen delivery device for a particular set of performance requirements is optimized.

Embodiments of the device may include any of the features described in the present disclosure, including any of the features described above in relation to the devices, system, and methods, including any one of the following features.

The particular set of performance requirements includes a particular oxygen purity level of oxygen produced by the oxygen delivery module, and a particular fraction of inspired oxygen (FiO2) value required for the patient.

The controller may further be configured to determine the optimal temperature at which the power consumption of the oxygen delivery device for the particular set of performance requirements is optimized by varying fan speed in discrete steps over an interval of time, at each varied fan speed value, determining the corresponding temperature and corresponding power consumption at the corresponding temperature, and identifying the temperature that resulted in the minimal power consumption.

In another aspect, a method is disclosed. The method includes determining data representative of one or more of environmental conditions, operating conditions of an oxygen delivery device, and a patient's therapeutic conditions, including at least one temperature sensor to measure temperature of the oxygen delivery device, and controlling operation of a fan, configured to cool the oxygen delivery device, based on the data determined by the one or more sensors, including the temperature measured by the temperature sensor, so as to cause the temperature of the oxygen delivery device to be at an optimal temperature at which power consumption of the oxygen delivery device for a particular set of performance requirements is optimized.

Embodiments of the method may include any of the features described in the present disclosure, including any of the features described above in relation to the devices, system, and methods, including the following feature.

Controlling operation of the fan may include determining the optimal temperature at which the power consumption of the oxygen delivery device for the particular set of performance requirements is optimized by varying fan speed in discrete steps over an interval of time, at each varied fan speed value, determining the corresponding temperature and corresponding power consumption at the corresponding temperature, and identifying the temperature that resulted in the minimal power consumption.

In a further aspect, an oxygen delivery device is disclosed. The oxygen delivery device includes an oxygen delivery module to produce at least concentrated oxygen, a first gas moving device to deliver air to the oxygen delivery module, the first gas moving device being driven by a first motor to actuate the first gas moving device, and a second gas moving device to draw exhaust gas from the oxygen delivery module, the second gas moving device being driven by a second motor, separate from the first motor, to actuate the second gas moving device. A first power signal used to drive the first motor is approximately 180° out of phase with a second power signal used to drive the second motor, and wherein frequencies of the first and second power signals are dithered over a 20% span at a rate of 900 Hz to reduce generated electromagnetic interference.

Embodiments of the device may include any of the features described in the present disclosure, including any of the features described above in relation to the devices, system, and methods.

In another aspect, an oxygen delivery device is disclosed. The oxygen delivery device includes an oxygen delivery module to produce at least concentrated oxygen, a gas moving device to deliver air to an oxygen delivery module, the gas moving device being driven by a motor to actuate the gas moving device, a purity sensor to determine oxygen purity value produced by the oxygen delivery module, and a controller to control operations of at least the oxygen delivery module and the gas moving device, based at least in part on the determined oxygen purity value, to cause the purity level of the oxygen produced by the oxygen delivery module to be less than 90%.

Embodiments of the device may include any of the features described in the present disclosure, including any of the features described above in relation to the devices, system, and methods.

In yet another aspect, an oxygen delivery device is disclosed. The oxygen delivery device includes an oxygen delivery module to produce at least concentrated oxygen, a gas moving device to deliver air to the oxygen delivery module, the gas moving device being driven by a motor to actuate the gas moving device, a communication module to communicate with a remote sensor configured to determine peripheral oxygen saturation of a patient, and a controller to control operations of at least one of the oxygen delivery module and the gas moving device, based at least in part on the determined peripheral oxygen saturation, to adjust the oxygen purity level of the oxygen produced by the oxygen delivery module to cause the peripheral oxygen saturation level of the patient to converge to a pre-determined required peripheral saturation level.

Embodiments of the device may include any of the features described in the present disclosure, including any of the features described above in relation to the devices, system, and methods, including any one of the following features.

The remote sensor may include a pulse oximeter to monitor the patient's oxygen saturation, the pulse oximeter being secured to skin of the patient.

The pulse oximeter may be configured to determine the change in light absorbance by the patient's tissue.

The communication module may be configured to wirelessly communicate with the remote sensor.

In an additional aspect, a method is disclosed. The method includes receiving data representative of peripheral oxygen saturation of a patient, the data being communicated from a remote sensor configured to determine the peripheral oxygen saturation of the patient, and controlling operations of at least one of an oxygen delivery module and a gas moving device of an oxygen delivery device, based at least in part on the data representative of the determined peripheral oxygen saturation of the patient, to adjust the oxygen purity level of the oxygen produced by the oxygen delivery module to cause the peripheral oxygen saturation level of the patient to converge to a pre-determined required peripheral saturation level.

Embodiments of the method may include any of the features described in the present disclosure, including any of the features described above in relation to the devices, system, and methods.

Other and further objects, features, aspects, and advantages of the present disclosure will become better understood with the following detailed description of the accompanying drawings.

BRIEF DESCRIPTION OF THE DRAWINGS

These and other aspects will now be described in detail with reference to the following drawings.

FIG. 1A is a block diagram of an oxygen delivery device.

FIG. 21 is a schematic diagram of an oxygen delivery used with a nebulizer.

FIG. 23 is a flow chart of an example procedure to deliver aerosolized medications.

Like reference symbols in the various drawings indicate like elements.

DETAILED DESCRIPTION

Figure 1B:
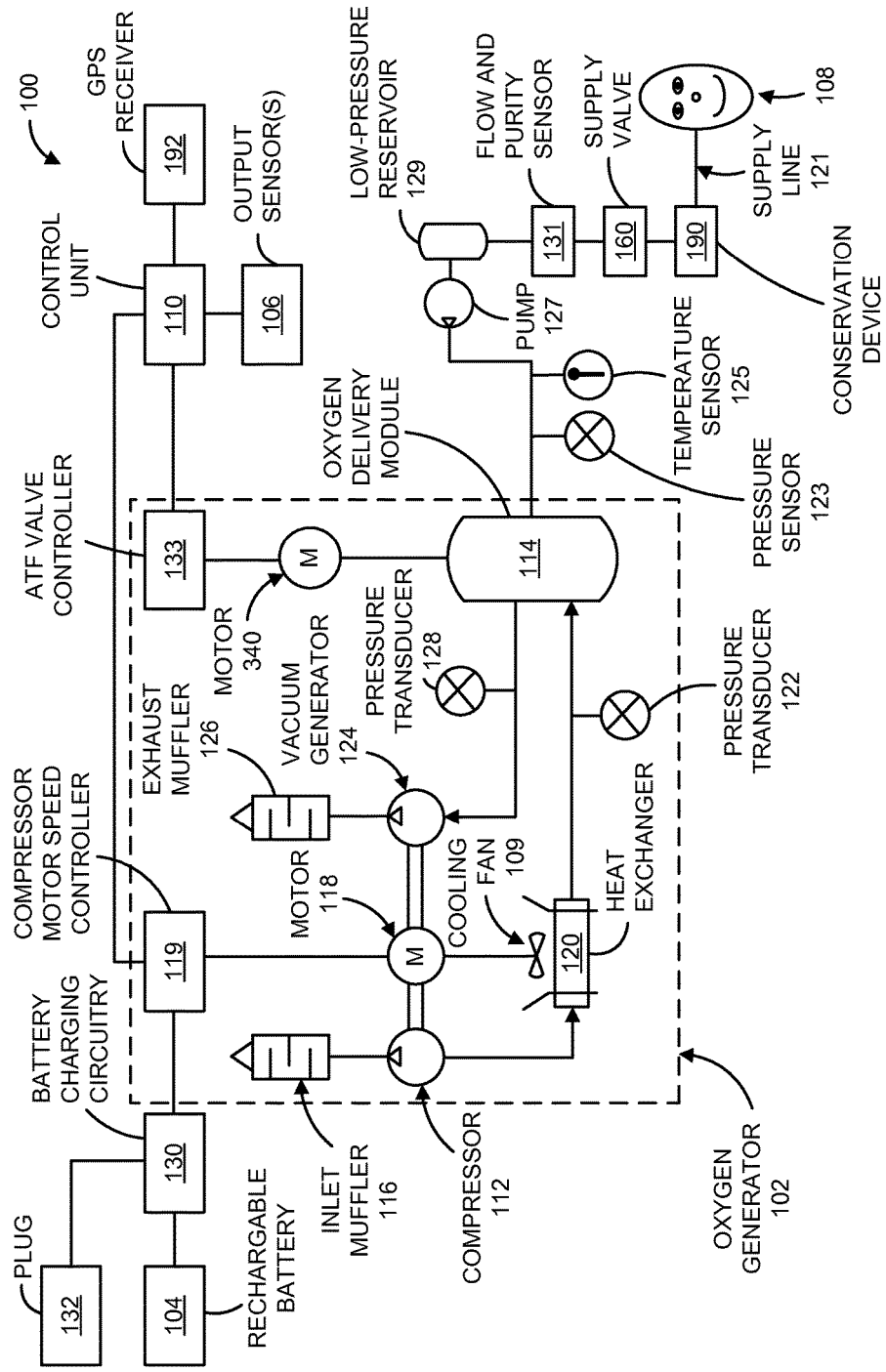
FIG. 1B is a schematic diagram of an oxygen delivery device that includes an example embodiment of an air separation device.

Disclosed herein are systems, methods and devices, including various implementations and embodiments of oxygen delivery devices.

In some implementations, an oxygen delivery device is provided that includes an oxygen delivery module (e.g., a pressure swing adsorption system, vacuum-pressure swing adsorption system, a vacuum swing adsorption system, a membrane seperator) to produce at least concentrated oxygen at a controllable purity level from ambient air, a gas moving device (e.g., a compressor, a vacuum pump) to deliver the ambient air to the oxygen delivery module), at least one controllable motor to controllably drive the gas moving device, an energy source to power the at least one controllable motor, a pressure sensor to determine a pressure level produced in the oxygen delivery device, and a purity sensor to determine oxygen purity value produced by the oxygen delivery module. The oxygen delivery device further includes a controller to control, based on the determined oxygen purity value and the pressure level, at least the gas moving device's operations and the oxygen delivery module's operations so as to cause the pressure resulting from the operation of the gas moving device to be substantially at a pre-determined pressure value and to cause the purity level of the oxygen produced by the oxygen delivery module to be substantially at a pre-determined purity value.

Also disclosed is an oxygen delivery device that includes an oxygen delivery module to produce at least concentrated oxygen, and a controller configured to control the oxygen delivery module to cause the oxygen delivery module to deliver oxygen to a patient based on a patient's tidal volume data representative of the normal volume of air displaced between inspiration and expiration by the patient, and further based on a fraction of inspired oxygen (FiO2) value required for the patient.

Further disclosed is an oxygen delivery device that includes an oxygen delivery module, at least one sensor to detect patient breathing, and a controller configured to control the oxygen delivery module to cause the oxygen delivery module to deliver oxygen to the patient based on data from the at least one sensor such that in response to a determination, based on data from the at least one sensor, that no breathing is detected for a first period of time, the controller causes the oxygen delivery module to deliver oxygen to the patient in continuous flow mode, and in response to a subsequent determination, based on data from the at least one sensor, that breathing is detected for a second period of time, the controller causes the oxygen delivery module to deliver oxygen to the patient in a pulse flow mode.

Also disclosed is an oxygen delivery device that includes an oxygen delivery module, one or more sensors to determine data representative of one or more of environmental conditions, operating conditions of the oxygen delivery device, and patient's characteristics, a controller to control, based at least in part on the determined data, at least the oxygen delivery module's operations, and a display module to present information based, at least in part, on the data representative of the characteristics of the patient.

In some implementations, an oxygen delivery device is provided that includes an oxygen delivery module configured to deliver a pulse including greater than 100 mL of concentrated oxygen, and a controller configured to control the oxygen delivery module to cause the oxygen delivery module to deliver the pulse including greater than the 100 mL of the concentrated oxygen within approximately first 60% of a patient's inspiratory period.

Further disclosed is an oxygen delivery device that includes an oxygen delivery module to provide at least concentrated oxygen, a piezoelectric valve coupled to an output of the oxygen delivery module to receive the produced concentrated oxygen, a driver to electrically actuate the piezoelectric valve, and a controller to control the driver to cause controllable actuation of the piezoelectric valve by the driver so as to cause controllable opening of the valve to enable flow of oxygen delivered by the oxygen delivery module to be directed for inhalation by a patient via the piezoelectric valve.

Further disclosed is an oxygen delivery device that includes an oxygen delivery module to produce at least concentrated oxygen, and a gas moving device to deliver air to the oxygen delivery module. The gas moving device includes at least one piston rotatable inside a first chamber defined in a housing, the rotational movement of the at least one piston inside the first chamber resulting in varying pressure generated in a first portion of the first chamber, and a vane member rigidly coupled to the at least one piston, the vane member being configured to move inside a vane chamber defined in the housing. The at least one piston and the vane rigidly coupled to the at least one piston defining the first portion of the first chamber and a second portion of the first chamber.

These and other embodiments of oxygen delivery devices are discussed in greater detail below.

I. Portable Oxygen Concentration System

With reference to FIG. 1A, a schematic diagram of a portable oxygen concentration system (also referred to herein as an oxygen delivery device), indicated generally by the reference numeral 100, and implemented in accordance with embodiments of the present disclosure, is shown. The oxygen delivery device 100 includes an air separation device such as an oxygen gas generator 102 that separates concentrated oxygen gas from air (ambient air), an energy source 104 such as rechargeable battery, battery pack, fuel cell, and/or a power transformer module (e.g., AC/DC or DC/DC converters) that powers at least a portion of the oxygen gas generator 102, and one or more output sensors 106 used to sense one or more conditions of the user 108, of the environment, etc., to determine the oxygen output needed by the user or required from the system 100. As depicted in FIG. 1, the device 100 also includes a control unit 110 (also referred to herein as a controller) coupled to the output sensor 106, the air separation device 102, and the energy source 104 to control the operation of the air separation device 102 in response to the one or more conditions sensed by the one or more output sensors 106.

In some embodiments, the device 100 may not include the one or more output sensors 106 coupled to the control unit 110. In such embodiments, conditions of the device 100, such as flow rate, oxygen concentration level, etc., may be constant for the system or may be controllable. For example, the system 100 may include a user interface (such as the user interface 111 depicted in FIG. 14) that enables a user, provider, doctor, etc., to enter information, e.g., prescription oxygen level, flow rate, etc., to control the oxygen output of the system 100.

Each element of the system 100 will now be described in more detail. A further description of other implementation of oxygen delivery device is provided, for example, in U.S. Pat. No. 6,691,702, entitled "Portable oxygen concentration system and method of using the same," the content of which is hereby incorporated by reference in its entirety.

A. Air Separation Device

With reference to FIG. 1B, a schematic diagram of a portable oxygen concentration system 100 (an "oxygen delivery device") is shown. In some embodiments, the air separation device is an oxygen generator 102 generally including a gas moving device, such as a compressor 112, and an oxygen delivery module 114 (also referred to as an oxygen concentrator, or OC) to provide at least concentrated oxygen, and may, in some embodiments, provide other types of concentrated gas). In some implementations, the oxygen delivery module may include one or more of, for example, a pressure swing adsorption system, a vacuum-pressure swing adsorption system, a liquid oxygen storage system, and/or a high pressure gaseous oxygen system. The gas moving device and oxygen delivery module may be integral.

In some embodiments, the oxygen generator 102 may also include one or more of the elements described below and shown within the segmented boundary line in FIG. 1B. Ambient air may be drawn through an inlet muffler 116 by the gas moving device (e.g., the compressor) 112. The compressor 112 may be driven by one or more DC motors 118 (M) that run off of DC electrical current supplied, for example, by the rechargeable battery 104 (RB). The motor 118 may also, in some embodiments, drive the cooling fan part of the heat exchanger 120. A variable-speed controller (VSC) or compressor motor speed controller 119 may be integral with or separate from the control unit 110 (CU) and may be coupled to the motor 118 to facilitate conserving electricity consumption. The compressor 112 delivers the air under pressure to the oxygen delivery module 114 that produces the at least concentrated oxygen.

In some embodiments, at maximum speed, air may be delivered to the oxygen delivery module 114 at 7.3 psig nominal and may range from 5.3 to 12.1 psig. At maximum speed, the flow rate of feed may be a minimum of 23.8 SLPM at inlet conditions of 14.696 psi absolute, 70 degrees F., 50% relative humidity.

In some implementations, a heat exchanger 120 may be located between the compressor 112 and the oxygen delivery module 114 to cool or heat the air to a desired temperature before entering the concentrator 114. A filter (not shown) may be located between the compressor 112 and the oxygen delivery module 114 to remove any impurities from the supply air, and a pressure transducer 122 may be located between the compressor 112 and the, oxygen delivery module 114 to get a pressure reading of the air flow entering the oxygen delivery module 114.

The oxygen delivery module 114 separates oxygen gas from air for eventual delivery to the user 108 via, for example, a supply line 121. One or more of the following components may be located along the supply line 121 between the concentrator 114 and the user 108: a pressure sensor 123, a temperature sensor 125, a pump 127, a low-pressure reservoir 129, a supply valve 160, a flow and purity sensor 131, and a conservation device 190. As used herein, supply line 121 may refer to the tubing, connectors, etc., used to connect the components in the line. The pump 127 may be driven by the motor 118, or by another motor. The oxygen may be stored in the low-pressure reservoir 129 and delivered therefrom via the supply line 121 to the user 108. The supply valve 160 may be used to control the delivery of oxygen gas from the low-pressure reservoir 129 to the user 108 at atmospheric pressure.

Exhaust gas may also be dispelled from the oxygen delivery module 114. In some embodiments, another gas moving device 124 (e.g., such as a vacuum generator), which may also be driven by the motor 118 and may be integral with the compressor 112, draws exhaust gas from the oxygen delivery module 114 to improve the recovery and productivity of the oxygen delivery module 114. The exhaust gas may exit the system 100 through an exhaust muffler 126. A pressure transducer 128 may be located between the concentrator 114 and the vacuum generator 124 to get a pressure reading of the exhaust flow from the oxygen delivery module 114. At maximum rated speed and a flow rate of 20.8 SLPM, the pressure at the vacuum side is, in some embodiments, −5.9 psig nominal and may range from −8.8 to −4.4 psig.

It is to be noted that in some embodiments, gas moving devices (e.g., a compressor and/or a vacuum pump) may be provided where the compressor and vacuum pump are included in a single casing driven by a single motor. However, in some embodiments, the compressor and vacuum pump may be separate elements. For instance, a separate variable speed compressor and a separate variable speed vacuum pump may be included where the compressor and vacuum pump are driven by separate motors and are thus capable of running independently from one another. In such a configuration, a VPSA system may be run at a multiplicity of settings based on a pressure and vacuum set point that has been optimized individually or based on a given pressure to vacuum and/or flow to pressure ratio. Optimization of the pressure and vacuum set points refers to a condition or conditions where the power required to run the system is relatively low for a specified oxygen flow and oxygen purity than a comparable system that has not been so optimized.

Thus, in some embodiments, an oxygen delivery device may be provided that includes an oxygen delivery module to produce at least concentrated oxygen, a first gas moving device (e.g., a compressor) to deliver air to the oxygen delivery module, with the first gas moving device being driven by a first motor to actuate the gas moving device to run at variable speeds, and a second gas moving device (e.g., a vacuum pump) to draw exhaust gas from the oxygen delivery module, with the second gas moving device being driven by a second motor, separate from the first motor, to actuate the second gas moving device to run at variable speeds.

By including an independent compressor and vacuum pump the system is not limited to operation at a fixed flow ratio, and may, therefore, be run at different operating points that may be optimized so as to account for a variety of inputs such as oxygen flow, a given ambient temperature or atmospheric pressure, required output purity, and the like. Further optimization may be achieved by combining the control of the compressor and/or vacuum pump in combination with one or more sensors for determining the purity of the flow. In such a manner, a purity feedback loop, for example, may be established so as to control the operation of the system at the lowest acceptable level of purity that is therapeutically appropriate and thereby reduce the power consumed. Such a range would be 85-90% oxygen purity, but could extend as low as 40% oxygen purity. As described herein, generally any suitable motor may be used to drive a compressor and/or vacuum pump described herein. In some embodiments, the motor may be a variable speed motor.

Thus, in such embodiments, an oxygen delivery device may be provided that further includes at least one sensor to determine data representative of one or more of environmental conditions, operating conditions of the oxygen delivery device, and patient's therapeutic conditions, and one or more controllers to control the speeds of the first gas moving device and the second gas moving by controlling operations of at least the first motor and the separate second motor based on the determined data. In some embodiments, each motor driving its respective gas moving device may be controlled by a separate controller, and in some embodiments a single controller may be used to control both motors. The determined data representative of the one or more of the environmental conditions, the operating conditions of the oxygen delivery device, and the patient's therapeutic conditions may include data representative of one or more of, for example, oxygen flow, ambient pressure, ambient temperature, and/or required oxygen purity.

In some embodiments, an oxygen delivery device may include separate motors for two different gas moving devices that are controlled using an oxygen purity feedback mechanism. Thus, in such embodiments, an oxygen delivery device may be provided that includes an oxygen delivery module (e.g., a PSA, VPSA) to produce at least concentrated oxygen, a first gas moving device to deliver air to an oxygen delivery module, with the first gas moving device being driven by a first motor to actuate the gas moving device to run at variable speeds, and a second gas moving device to draw exhaust gas from the oxygen delivery module, the second gas moving device being driven by a second motor, separate from the first motor, to actuate the second gas moving device to run at variable speeds. Such an oxygen delivery device also includes a purity sensor to determine oxygen purity value produced by the oxygen delivery module, and a controller to control speeds of the first and second gas moving devices by controlling operations of at least the first motor and the separate second motor based, at least in part, on the determined oxygen purity value, to cause the purity level of the oxygen produced by the oxygen delivery module to be substantially at a pre-determined purity value. In some embodiments, the pre-determined purity value may be the minimum acceptable oxygen purity level to enable energy consumption of the system to be reduced, such a pre-determined purity value having a value of between approximately 82% and approximately 93% of oxygen.

The inclusion of separate compressor and vacuum pump motors could cause an increase in the noise of the system and/or may cause an increase in the mechanical vibrations and stress of the oxygen delivery device. Noise resulting from use of a separate compressor and vacuum pump may be reduced in part by configuring the motors and/or control thereof for active EMI cancellation. For instance, the PWM signal used to drive the two motors may be configured so as to be 180° (or approximately 180°) out of phase with one another, and to have their frequencies be dithered over a 20% span, such as at a rate of 900 Hz, thus reducing the noise of the system overall. For example, by controlling the currents driving each motor so as to be out of phase with one another, the ripple noise on the DC bus may be cancelled and EMI reduced. Further noise reduction may be achieved by dithering the frequency of the current which reduces the radiated EMI. Accordingly, in some implementations, an oxygen delivery device may include an oxygen delivery module to produce at least concentrated oxygen, a first gas moving device to deliver air to the oxygen delivery module, with the first gas moving device being driven by a first motor to actuate the first gas moving device. Such an oxygen delivery device also includes a second gas moving device to draw exhaust gas from the oxygen delivery module, with the second gas moving device being driven by a second motor, separate from the first motor, to actuate the second gas moving device. In such implementations, a first power signal used to drive the first motor is approximately 180° out of phase with a second power signal used to drive the second motor, and frequencies of the first and second power signals are dithered over a 20% span at a rate of 900 Hz to reduce generated electromagnetic interference.

In some embodiments, one or more stepper motors may be provided to drive the oxygen delivery device's oxygen delivery module. For instance, a modulated stepper driver may be included where the controller produces a modulating signal that is injected into a full-step stepper motor drive signal. For example, the controller may be configured (by appropriate programming of a programmable processor-based controller) to modulate the slew rate of the full-step current waveform that is driven into the stepper motor coils. As a result, the vibration and structural noise emanating from the stepper motor may be reduced without a loss in efficiency or the need for extraneous sound suppression methods. Accordingly, in such embodiments, an oxygen delivery device may be provided that includes an oxygen delivery module to produce at least concentrated oxygen, a gas moving device to deliver the ambient air to the oxygen delivery module, a stepper motor comprising one or more electromagnetic coils arranged around a gear element, with the stepper motor being configured to drive at least the oxygen delivery module. Such a device (also includes a controller configured to modulate the driving signals used to energize the one or more electromagnetic coils to achieve a specified slew rate so as to reduce the vibration and structural noise emanating from the stepper motor without loss of efficiency.

1. Compressor/Variable Speed Controller

Example of compressor technologies that may be used for gas moving devices (e.g., the compressor 112 and vacuum generator 124 depicted in FIG. 1B) include, but not by way of limitation, rotary vane, linear piston with wrist pin, linear piston without wrist pin, nutating disc, scroll, rolling piston, a rotatable piston (for use in implementations of rotary gas moving device, which will be described in greater details below), diaphragm pumps, and acoustic. In some embodiments, the compressor 112 and vacuum generator 124 are integrated with the motor 118 and are oil-less, thus preventing the possibility of oil or grease from entering the air flow path.

The compressor 112 includes, in some embodiments, a 3:1 speed ratio, with a low speed of at least 1,000 rpm and a 15,000 hour operating life when run at full speed. Operating temperature surrounding the compressor/motor system may be, in some embodiments, 32 to 122 degrees F. Storage temperature may be −4 to 140 degree F. Relative humidity may be 5 to 95% RH noncondensing. Voltage for the compressor 112 may be 12 V DC or 24V DC and the electrical power requirements may be less than 100 W at full speed and rated flow/nominal pressure and less than 40 W at ⅓ speed and ⅓ flow at rated pressure. A shaft mounted fan or blower may be incorporated with the compressor 112 for compressor cooling and possible complete system cooling. In some embodiments, the maximum sound pressure level of the compressor 112 may be 46 dBA at a maximum rated speed and flow/pressure and 36 dBA at ⅓ rated speed. In some embodiments, the compressor 112 weighs less than 3.5 pounds.

In some embodiments, the compressor 112 is configured to run at a variety of speeds, provide the required vacuum/pressure levels and flow rates, emit little noise and vibration, emit little heat, be small, not be heavy, and consume little power.

The variable-speed controller 119 is important for reducing the power consumption requirements of the compressor 112 on the energy source 104. With a variable-speed controller, the speed of the compressor 112 may be varied with the activity level of the user, metabolic condition of the user, environmental conditions, or other condition indicative of the oxygen needs of the user as determined through the one or more output sensors 106.

For example, the variable-speed controller may decrease the speed of the motor 118 when it is determined that the oxygen requirements of the user 108 are relatively low, e.g., when the user is sitting, sleeping, at lower elevations, etc., and may increase the speed of the motor when it is determined that the oxygen requirements of the user 108 are relatively high or higher, e.g., when the user stands, when the user is active, when the user is at higher elevations, etc. This helps to conserve the life of the energy source 104, reduce the weight and size of the battery 104, and reduce the compressor wear rate, thus improving its reliability.

Thus, in some embodiments, a variable-speed controller, such as the controller 119 depicted in FIG. 1B, to regulate the compressor speed to operate the compressor only at the speed and power needed to deliver oxygen at the user's prescribed flow rate is provided. Such a variable speed controller may thus be configured to regulate the speed of the compressor (or other gas moving devices) based, at least in part, on data determined by one or more sensors (i.e., through measurements) representative of one or more of environmental conditions (e.g., ambient pressure, ambient temperature), operating conditions of the oxygen delivery device (e.g., power level of the power source, existence of faults or malfunctions, etc.), and/or therapeutic conditions of the user (patient) using the oxygen delivery device (e.g., patient's breathing rate). Additional details regarding variable-speed controllers are provided in U.S. Pat. Nos. 5,593,478 and 5,730,778, the contents of all of which are hereby incorporated by reference in their entireties as though set forth in full.

The variable-speed controller 119 described herein allows the compressor 112 to operate at a low average rate, where typically the average rate or speed will be between full speed and ⅙ full speed of the compressor 112 (or some other gas moving device), resulting in an increase in battery life, decrease in battery size and weight, and decrease in compressor noise and emitted heat.

Additionally, to facilitate controlling operations of the gas moving device (such as the compressor), a rotary valve is included with the oxygen delivery module (the rotary valve regulates the air flow entering the oxygen delivery module, and selectively transfers fluids into the oxygen delivery module) may be an indexed valve to enable determination of operating state of the oxygen delivery module. For instance, the valve assembly may include an index mark so that the valve position as well as the number of valve rotations may be tracked. For example, the rotary valve may include an indicator that indicates a rotary position. The indicator may be aligned with features on the face of the valve. As the indexing indicator passes a switch, a signal from the switch is communicated to the controller. In one embodiment, the switch may be an optical switch (see, for example, the switch 1810 shown in FIG. 30) and the indexing indicator may be an interrupt flag, such as for a transmissive type switch, or a contrasting color/stripe, such as for a reflective type switch. In some embodiments, the switch may be mechanically activated and the indexing feature may be any suitable feature sufficient to activate the switch by mechanical actuation of the switch by the indexing indicator.

Accordingly, in some implementations, an oxygen delivery module, of an oxygen delivery device, may include one or more adsorbent beds configured to selectively adsorb corresponding materials from fluid directed through the one or more adsorbent beds, and a rotary valve for selectively transferring the fluid through the one or more adsorbent beds, with the rotary valve including an index indicator detectable by a sensor. The oxygen delivery device also includes one or more sensors to detect the indexing indicator on the rotary valve. In such implementations, a controller of the oxygen delivery device is configured to determine from information relating to the indexing indicator detected by the one or more sensors at least one of, for example, rotational position of rotary valve, and/or number of rotation cycles completed by the rotary valve during a pre-determined period of time. Such a controller may further be configured to cause actuation of the rotary valve, based on the rotational position of the rotary valve determined from the information relating to the detected indexing indicator, to rotate the rotary valve to a position where passages between ambient air and the one or more adsorbent beds are closed so as to prevent atmospheric moisture from reaching the one or more adsorbent beds.

As will be described in greater details below, in some implementations, the rotary valve may include a rotary valve shoe and a valve port plate having respective engaged surfaces, with the rotary valve shoe being rotatable to provide valving action for selectively transferring fluids therethrough, the rotary valve shoe including multiple passages allowing fluid to flow therethrough. The rotary device also includes a fluid distribution manifold to distribute fluids between the adsorption beds and the valve members, with fluid distribution manifold including multiple passages allowing fluid to' flow through them, and one or more passages of at least one of the rotary valve shoe and the fluid distribution manifold including purge passages.

The determination of valve rotations is useful in tracking the number of cycles performed, which in turn may be used to determine actual usage of the device and wear on the valve assembly. Further, in circumstances where the motor is a stepper motor, when a stop command is issued, the controller can command the stepper to stop the valve one or more steps after the index mark has been passed. Such a configuration enables the valve position to be such that there is no open conduit between the adsorbent and the ambient air, thus further serving to prevent moisture from interacting with the sieve.

Figure 6:
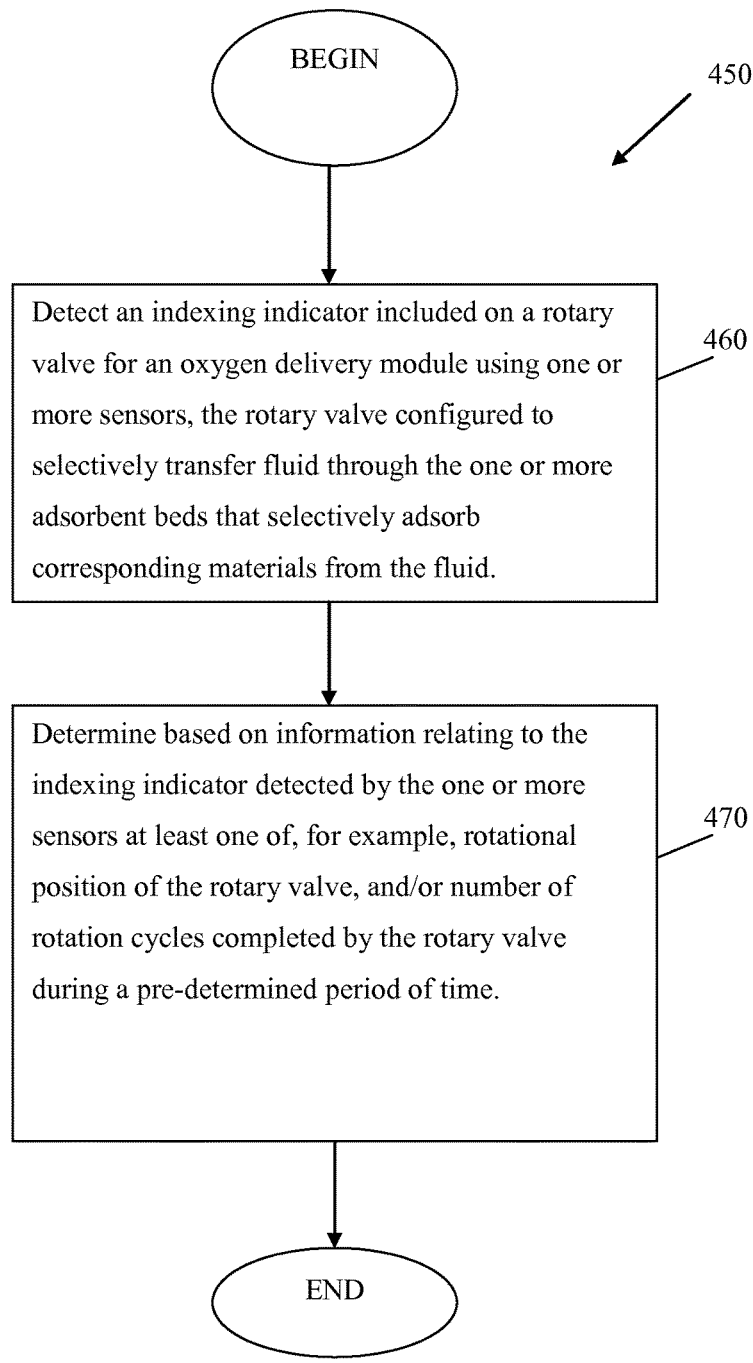
FIG. 6 is a flow chart of an example procedure for moving/directing gas.

With reference to FIG. 6, a flow chart of an example embodiment of a procedure 450 based on the use of an indexed rotary valve is shown. The procedure 450 includes detecting 460 an indexing indicator on a rotary valve for an oxygen delivery module using one or more sensors (e.g., an optical switch to optically detect the indexing indicator when the indexing indicator passes by the optical switch, a mechanical switch configured to be mechanically activated upon mechanical actuation of the switch by the indexing indicator). A determination is made 470, e.g., by a controller in communication with the one or more sensors, based on information relating to the indexing indicator detected by the one or more sensors, of at least one of, for example, rotational position of the rotary valve, and/or number of rotation cycles completed by the rotary valve during a pre-determined period of time. As noted, in some embodiments, the rotary valve may be actuated based on the rotational position of the rotary valve determined from the information relation to the detected indexing indicator, to rotate the rotary valve to a position where passages between ambient air and the one or more adsorbent beds are closed.

2. Rotary Gas Moving Devices

In some embodiments, it may be desirable to have the compressor and vacuum pump provided as a single unit. Thus, in some implementations, a swing compressor may be provided where the compressor and vacuum pump are provided as two opposed heads that are integrated into a single unit. The unit may include two rotating heads, e.g., a pressure and a vacuum pump head, that are offset from one another so as to be about 180° out of phase. In this manner, vibration and structural noise may also be reduced without having to introduce extraneous sound suppression mechanisms.

The swing compressor may include a piston that articulates within a compression chamber, forming a compressor head, and a second piston that articulates within a second compression chamber, forming a vacuum head. The two heads may be positioned to be about 180° opposed to one another. As the piston of the compressor head approaches top-dead center, pressure in a first compression chamber increases, and as a result, the torque required to turn the shaft driving the piston increases. Due to the configuration of the system, this pressure and torque may be periodic, e.g., roughly sinusoidal. The piston of the vacuum head produces comparable pressures and torques as it reaches top-dead center. By offsetting these loads by about 180 degrees the sinusoidal pressures and torques can serve to cancel one another out. By doing so, the net forces resulting on the swing compressor assembly are minimized, which in turn leads to less vibration and therefore less sound being generated, consequently reducing the noise level. This also serves to lessen peak torques in the assembly, which in turn reduces peak electrical currents drawn by the motor driving the compressor head and vacuum head assembly.

Thus, as described herein, in some implementations, an oxygen delivery device is provided that includes an oxygen delivery module to produce at least concentrated oxygen, and a gas moving device to deliver air to the oxygen delivery module. The gas moving device (e.g., a compressor, a vacuum pump) includes at least one piston rotatable inside a first chamber defined in a housing, the rotational movement of the at least one piston inside the first chamber resulting in varying pressure generated in a first portion of the first chamber. The gas moving device also includes a vane member rigidly coupled to the at least one piston, the vane member being configured to move inside a vane chamber defined in the housing. The piston and the vane rigidly coupled to the piston define the first portion of the first chamber and a second portion of the first chamber. Implementations of a gas moving device that include at least one such rotating piston may also be referred to as rotary gas moving device, e.g., rotary compressors. In some embodiments, oxygen delivery devices, implemented using, for example, rotary gas moving devices, may have a weight of between 2-15 pounds.

Figure 2A:
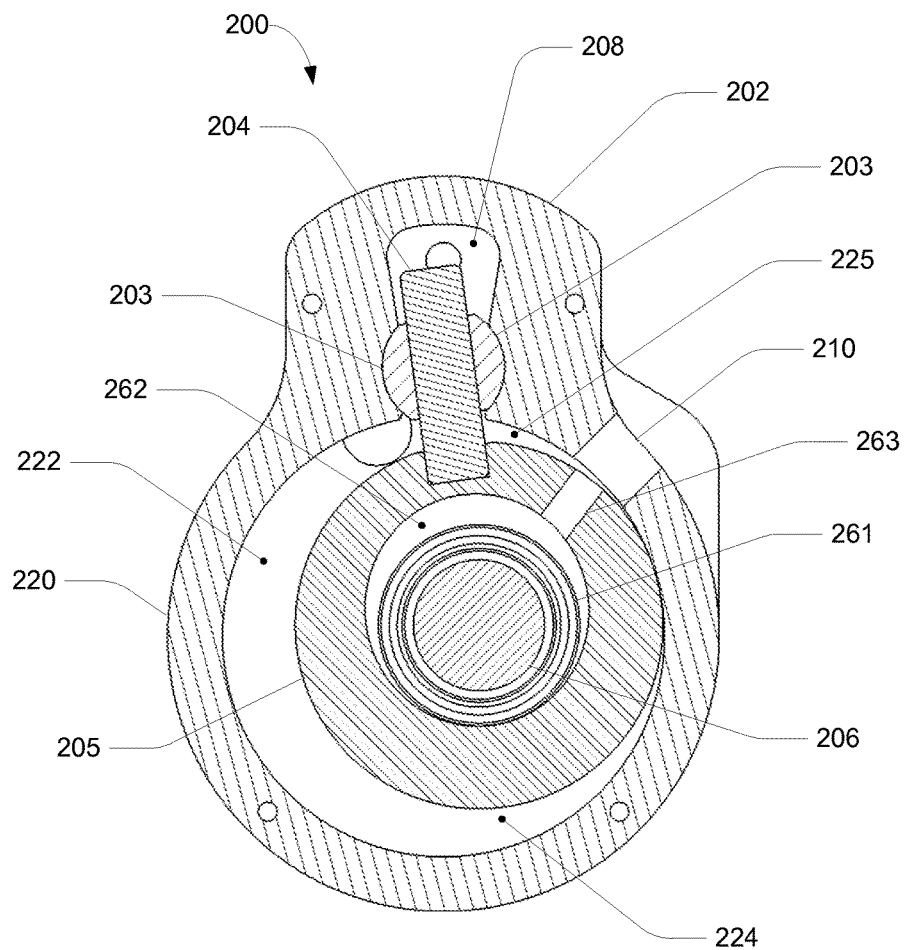
FIG. 2A is a cross-sectional diagram of an example rotary gas moving device.

With reference to FIG. 2A, a cross-sectional diagram of a rotary gas moving device (e.g., a rotary compressor) 200 is shown. Details regarding some implementations of rotary (swing) gas moving devices are provided, for example, in co-owned patent application Ser. No. 12/879,998, entitled "Rotary Compressor and Method," the content of which is hereby incorporated by reference in its entirety. In some embodiments, the rotary gas moving device (rotary compressor) 200 includes, in some implementations, a stator 202 that is associated with a bushing 203, a vane 204, and a piston 205. The piston 205 is rotatable inside a chamber 222 defined in a housing 220 of the compressor. The piston may be, in some embodiments, a cylinder rotatable inside the chamber 222 having curved (arched) walls. The rotational movement of the piston 205 results in varying pressure generated in a first portion 224 of the first chamber 222. In some embodiments, the varying pressure may be represented as a first periodic function (e.g., a sinusoidal-based function) of the pressure generated in the first portion of the first chamber. The vane 204 is rigidly coupled to the piston 205 and is configured to move inside a vane chamber 208 defined in the housing 220. The structure including the vane 204 rigidly coupled to the piston 205 defines the first portion 224 of the chamber 222, and a second chamber 225 (which, in some embodiments, may be a suction chamber).

As further shown in FIG. 2A, the rotary compressor 200 also includes a shaft 206 having the bearing 261 associated therewith. As can be seen, in this embodiment, the stator 202 includes the inlet port 210. Further, an inner chamber 262 and a passage 263 in the piston 205 form an accumulator volume. The accumulator volume may function in part to reduce inlet pulsation noise. For instance, as the piston moves past the suction port 210 in the stator 202, the incoming flow is abruptly slowed. This inlet flow stagnation can result in pressure waves that can typically cause objectionable noise. This configuration of the piston accumulation volume and stator containing inlet port can reduce the abrupt slowing of the flow and thereby reduce objectionable noise. The accumulator volume can also be formed by modifying the stator 202 in the inlet area or by allowing fluid communication between the vane chamber 208 and second (suction) chamber 225. It is to be noted that since the piston is moving relative to the stator, the inlet port will be periodically opened and closed, as will be described in greater detail below.

Figure 2B:
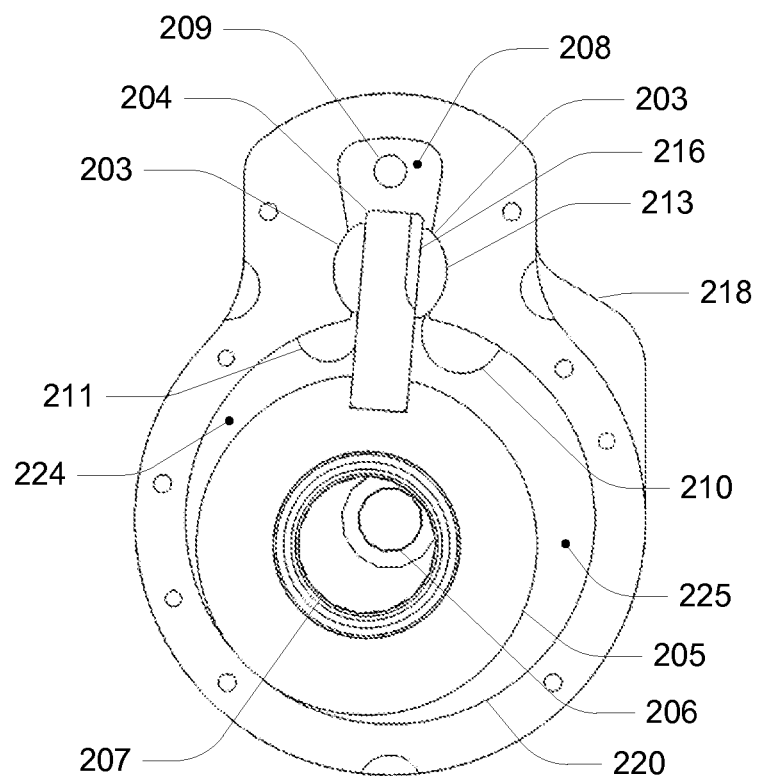
FIG. 2B is a cross-sectional view of an example rotary compressor.

Operation of the rotary compressor of oxygen delivery device will be explained with reference to FIG. 2B showing a front elevation view of another example embodiment of a rotary compressor (which may similar to the example embodiment of a rotary compressor shown in FIG. 2A).

In FIG. 2B, the inlet or suction port 210 is visible in a suction endplate 218 (also shown in FIG. 3, described below). The location of a discharge port (not shown) is indicated by a discharge dimple 211 located in the suction plate 218. As noted, the shaft 206 has a cylindrical shaft eccentric 207 the centerline of which is parallel to but not concentric with the shaft 206 centerline. The shaft eccentric 207 occupies the space within the piston interior diameter, and is rotatably mounted with the inside diameter of the piston 205 such that the centerline of the piston 205 is eccentric with respect to the centerline of the stator bore chamber 220. The interface between the shaft eccentric 207 and the interior diameter of the piston 205 may additionally include one or more bearings, e.g., rolling element bearings, plain bearings, journal bearings, and the like.

As the shaft 206 rotates, e.g., clockwise, the offset eccentric rotates, thus driving the piston around in a rotation that is approximately orbital. The eccentricity of the piston 205 is such that the piston outside diameter contacts, or nearly contacts, a small zone of the stator surface defining the bore 220. The vane 204 extends radially from the piston 205, and is slidably engaged between the two bushings 203. The bushings 203 are rotatably engaged in the in the bushing chambers 213.

As the shaft 206 continues to rotate the piston 205 is driven along a circular or orbital path. Rotation of the piston 205 is limited by the engagement of the vane 204 with the bushings 203. Therefore, the motion of the piston 205 is nearly orbital.

The arrangement of the vane 204 and the eccentricity of the piston 205 is such that the volume within the stator bore chamber 220 is divided into a suction chamber 225 and a compression chamber 224. As the shaft 206 rotates, e.g., clockwise, fluid is passed through the inlet port 210, e.g., via tubing connected to a fluid source, and into the suction chamber 225 that is increasing in volume as the compression chamber 224 decreases in volume. The increasing volume of the suction chamber 225 causes fluid to be drawn into the suction chamber 225 via the suction port 210. As the piston 205 moves in its orbital rotation, the suction port 210 becomes progressively closed off by the piston 205, and the suction volume will become a compression volume.

As the piston 205 continues in its rotation, the compression volume 224 decreases. The decreasing volume of the compression chamber 224 compresses the fluid in the compression chamber 224 until the pressure in the compression chamber is approximately the same pressure as the fluid downstream of a discharge port 219 (depicted in FIG. 3).

The implementation of the rotary compressor 200 may include a valve covering the downstream end of the discharge port 219 in a manner that the general flow of fluid is only permitted out of the compression chamber 224. For example, in some embodiments, when the pressure within the compression chamber is about equal to or greater than the pressure downstream of the discharge valve, the valve is caused to open and the fluid is forced out of the compression chamber 224.

As the shaft 206 continues to rotate the volume of the compression chamber 224 reaches a minimum and the volume in the suction chamber 225 reaches a maximum. Additional rotation isolates the suction volume 225 from the suction port 210. At this point the suction chamber 225 no longer draws fluid, and as the piston 205 continue to rotate the chamber 225 will decrease in volume. Accordingly, at the point that the chamber into which fluid (liquid and/or gas) was drawn no longer functions to draw fluid, that chamber becomes a compression chamber, whereas the hitherto compression chamber 224 will start drawing fluid into its volume, and thus will become a suction chamber. This cycle repeats as the shaft rotates, such that a continuous flow of compressed fluid is produced. Hence, fluid is continuously drawn in on one side, compressed and discharged on the other side of the larger bore chamber 222 of the compressor 200.

The vane chamber 208 located near the top of the compressor in the FIG. 2A operates, in part, as a clearance for the vane 204 such that as the piston 205 rotates, the vane is moved up and down in and out of the vane chamber 208 in a linear and/or rotational oscillation. An optional vane chamber vent 209 (shown in FIG. 2B) is located in the vane chamber 208. The vane chamber vent 209 may be included so as to control the fluid pressure within the vane chamber. The vent 209 may be controlled by an external or internal source. For example, in certain instances, a pressure source may be provided where the pressure source is in fluid communication with the vane chamber portion, e.g., through a controlled vane. Accordingly, a control mechanism may also be provided to control the fluid pressure in the vane chamber. In some implementations, the control mechanism may control one or more of the valve and/or a pressure source. The pressure source may be any suitable pressure source, and in certain instances the pressure source may include an ambient pressure source, a pressure source that is above ambient pressure, or a pressure source is below ambient pressure.

In some implementations, the compressor includes axially separated surfaces, and one or more endplates effectively sealing the first chamber the rotatable piston includes a cylindrical piston with an exterior diameter, the cylindrical piston being operatively associated with a drive member disposed within the first chamber and rotatable therein, and further being offset with respect to a centerline of the first chamber portion such that the exterior diameter of the piston is in close proximity to bounds of the first chamber portion during orbit of the piston, to divide the first chamber into a suction chamber portion and a compression chamber portion. Examples of such implementations are depicted in FIG. 3, showing an exploded perspective view of an example rotary compressor.

Figure 3:
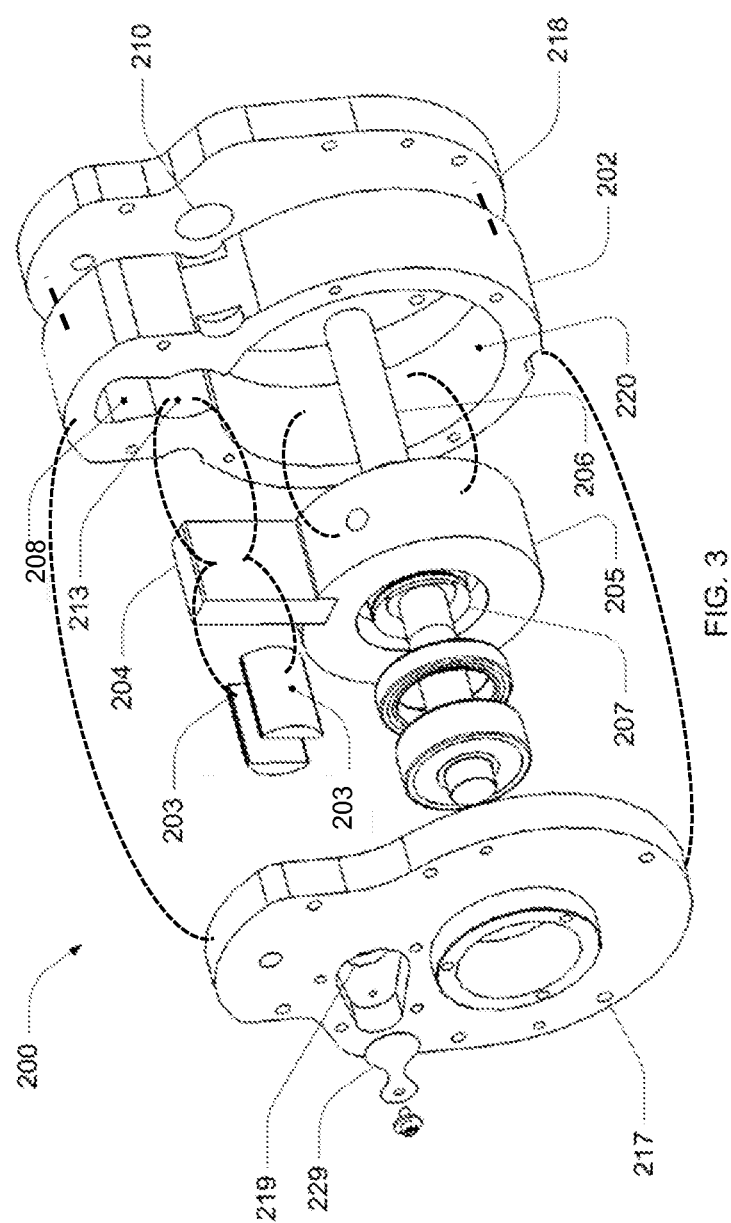
FIG. 3 is an exploded perspective view of an example rotary compressor.

As noted, and as also depicted in FIG. 3, the rotary compressor 200 includes several inter-related parts. For example, the compressor includes the housing which may be formed as the stator 202 and may include two endplates, namely, a discharge end plate 217 and a suction end plate 218. As depicted, the discharge end plate 217 includes a discharge port 219, and the suction endplate 218 includes the suction port 210. It is to be noted that although the discharge and suction ports are shown as being associated with respective endplates, in some embodiments, one or both ports may be associated with a single endplate or other parts of the compressor housing. Also, it is to be noted that although the endplates are depicted as separate components from the housing, an endplate can be an integral part of the housing.

With reference again to FIG. 2B, as noted, the cavity includes three sections or chambers. One chamber defines the vane chamber 208 (also discussed in relation to FIG. 2A), in which the vane 204 resides and moves. Another chamber is a bushing chamber 213 in which bushings 203 reside. The chamber 222 comprises a large cylinder or bore chamber that forms a suction and/or compression space volume in which the piston 205 resides.

The vane 204 is an extended member, a portion of which is associated with the piston 205 and another portion of which extends into one or both of the bushing chamber 213 and the vane chamber 208. In certain instances, the vane is integrally formed with the piston and in other instances the vane is detachably attached to the piston.

The bushing chamber 213 may include one or more bushings and a vane. The bushing chamber 213 of the stator 202 is formed by opposing curved surfaces which may interface with bushing bearings, which in turn interface with bushings 203. Consequently, the bushings 203 may include both a curved surface, configured to fit snugly within the curved recess of the bushing chamber of the stator 202 and/or bushing bearings positioned therein, and a relatively flat surface, adapted to interface with a flat surface of the vane 204. The bushings 203 in conjunction with the vane 204 form a fluid seal that separates the suction and/or compression portions (224 and 225, respectively, as depicted in FIG. 2A) defined in the bore chamber 222, from the vane chamber 208.

As noted, the piston 205 may be, in some implementation, a cylindrical member comprising both an exterior portion having an exterior diameter and an interior portion having an interior diameter. The exterior portion diameter is less than that of the large bore diameter and thus the piston 205 does not occupy the entire space of the large bore chamber 220, but rather moves about in an orbital motion therein. The interior diameter portion forms an orifice within which the shaft 206 and a shaft eccentric 207 are positioned. The exterior portion of the piston 205 includes a cut out portion, e.g., a vane cleft, which is configured for receiving a distal portion of the vane 204. The vane 204 is rigidly coupled (affixed) to the piston 205 such that relative motion between the vane 204 and piston 205 generally does not occur. Alternatively, the vane 204 and piston 205 can be a single component. The vane 204 interacts with the piston 205 and the bushings 203 so as to define two distinct sub-chambers within the large bore chamber 222, namely, the first chamber portion 224, and the second chamber portion 225.

The piston 205 may be offset from a centerline of the large bore such that as the piston orbits within the bore the outer diameter portion of the piston approximates the exterior surface of the stator 202. In some embodiments, the outer portion may contact the exterior surface defining the stator bore chamber, in other instances there will be a small clearance there between. In instances where there is a small clearance, this clearance may range from about 1 micron up to, and including, about 50 microns. Additionally, where there is an axial clearance between axial surfaces, such as between the piston and the endplates, the axial clearance may range from about 1 to about 100 microns. In some embodiments, the compressor may have a compression ratio of between about 1 and about 5 (for example, between about 2 or 2.5 and 4, including about 3 and about 3.15).

In some embodiments, the oxygen delivery device may further include at least one additional gas moving device, with each of the additional gas moving device including a corresponding additional piston rotating inside a corresponding bore chamber defined in the housing, the rotational movement of the corresponding additional piston inside the corresponding bore chamber results in corresponding pressure represented as a corresponding additional periodic function created in a corresponding portion of the corresponding bore chamber, and a corresponding additional vane member coupled to the corresponding additional piston, the corresponding additional vane being configured to move inside a corresponding additional vane chamber defined in the housing.

For example, in some embodiments, the oxygen delivery device may include two gas moving devices, e.g., two compressors. Thus, in such embodiments, a first gas moving device may include a first piston rotating inside a first chamber (e.g., a bore chamber) of the first gas moving device) to facilitate compression operations, and a second gas moving device includes a second, separate piston rotating inside a second chamber (another bore chamber) defined in the housing to facilitate vacuum pump operations.

Figure 4:
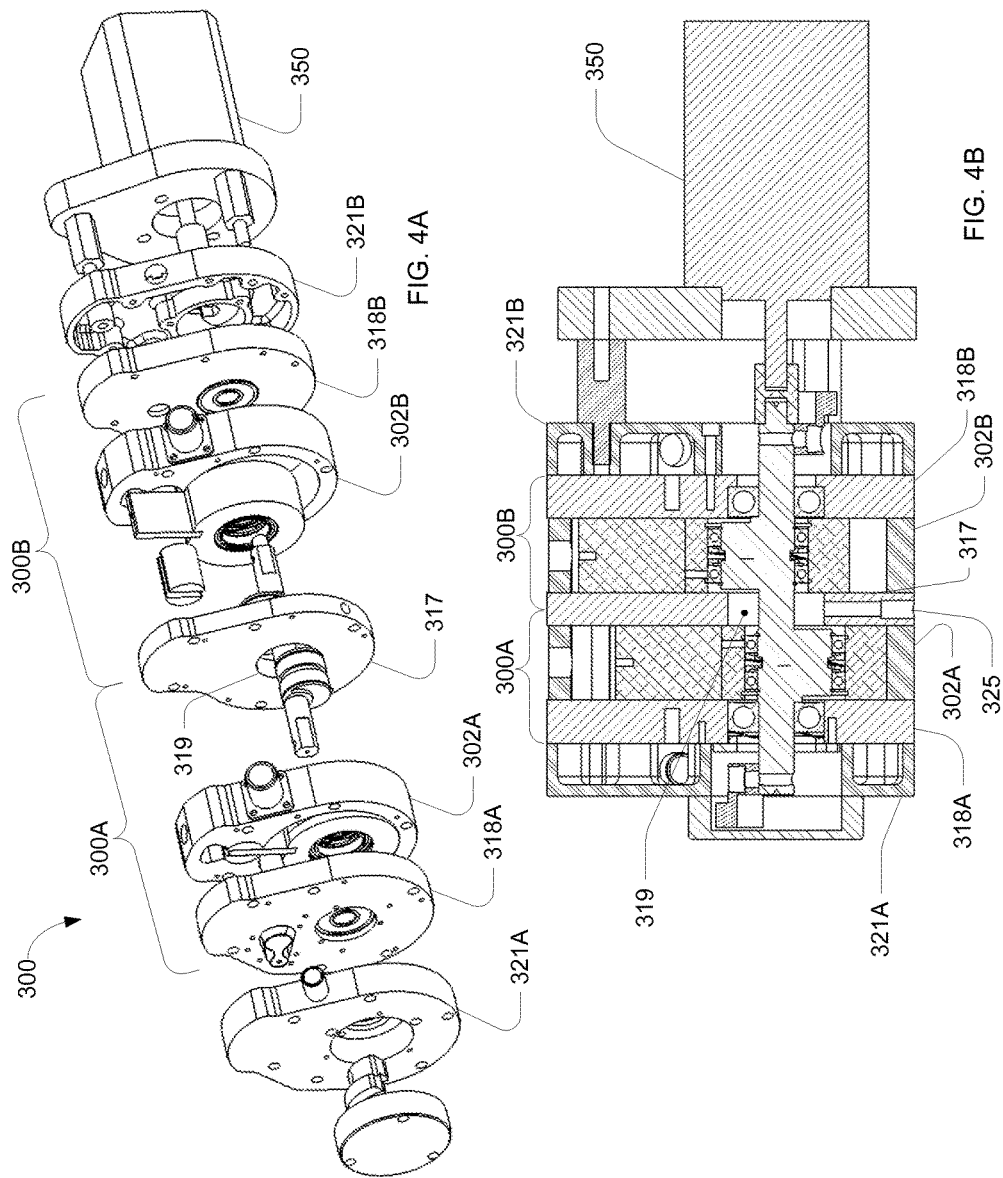
FIG. 4A is an exploded perspective view of a two-compressor implementation operated by a single motor for use with, for example, an oxygen delivery device.
FIG. 4B is a cross-sectional view of the implementation of FIG. 4A.

Particularly, with reference to FIG. 4A, an exploded perspective view of a two compressor implementation 300 operated by a single motor for use with, for example, an oxygen delivery device is shown. The implementation 300 includes compressors 300A and 300B that are driven by a single motor 350. As can be seen with respect to FIG. 4A, the first compressor 300A includes a housing 302A, which is positioned between two endplates 318A and 317. The second compressor 300B includes a housing 302B, which is positioned between two endplates 318B and 317. As depicted, both compressors 300 A and B share the common endplate 317. However, in some embodiments, each compressor can each have its own, non-shared endplates. Also included are mufflers 321A and 321B. In implementations of two compressors driven by a single motor, as shown in the cross-sectional view of FIG. 4B, one compressor may act to increase pressure above ambient pressure, and one compressor may act to reduce pressure below ambient pressure. In some embodiments, gas may leak into an endplate chamber, e.g., endplate chamber 319. Gas that leaks into the endplate chamber from the pressure unit may be relatively hot and at a relatively high pressure. Such gas will tend to be drawn from one unit into another, such as into the vacuum unit, thus reducing efficiency. A vent hole 325 (shown in FIG. 4B), therefore, may be positioned in the shared endplate and used to keep the endplate chamber at an optimal pressure. This optimal pressure may be ambient pressure or some other pressure and/or may be from another source. This can prevent shared fluid exchange between the compressors and/or can reduce the effects of the pressure of one compressor from having deleterious effects on the other compressor.

It is to be noted that other types of gas moving devices may be used in addition to or in place of the compressors 300A and 300B depicted in FIGS. 4A and 4B, and also that additional, gas moving devices may be used in a multi-gas moving device configuration. For example, in some embodiments, three, four, or more gas moving devices may be used, of which one, some, or all may be driven by a single rotary power source.

As noted, in some embodiments, the operation of rotary pistons such as those described herein may be implemented so as to reduce overall mechanical vibrations, reduce structural, stress, and/or reduce noise produce through operations of the gas moving devices. For example, mechanical vibrations, stress and/or noise can be reduced by having rotary pistons (in implementations that employ multiple piston) have a phase offset from one another. Thus, in some implementations, forces resulting from the rotational movement of a first piston in a first chamber may destructively interfere with forces resulting from the rotational movement of a second piston in a second chamber such that net forces created in the oxygen delivery device are reduced.

Thus, in embodiments such as those depicted in FIGS. 4A and 4B, the pistons could be rotating so that pressure (e.g., compression pressure) created in a first chamber where a first piston rotates (such pressure being represented as a periodic function) is approximately 180° out of phase with pressure (e.g., compression pressure) created in a second chamber where a second piston rotates (with the pressure in the second chamber also represented as a periodic, for example, a sinusoidal, function). In some embodiments, the relative radial position of a first piston in a first chamber (where the first piston rotates), which may be represented as a first periodic function, and the relative radial position of a second piston in a second chamber (where the second piston rotates), which may be represented as a second periodic function, are configured to be out of phase in relation to each other. That is, in some embodiments, the relative radial position of the two pistons are made to be offset from each other (e.g., by about 180°) so that pressure build up in the chambers, and thus mechanical vibrations and noise, can destructively interfere with each other to reduce overall vibrations and noise.

Figure 5:
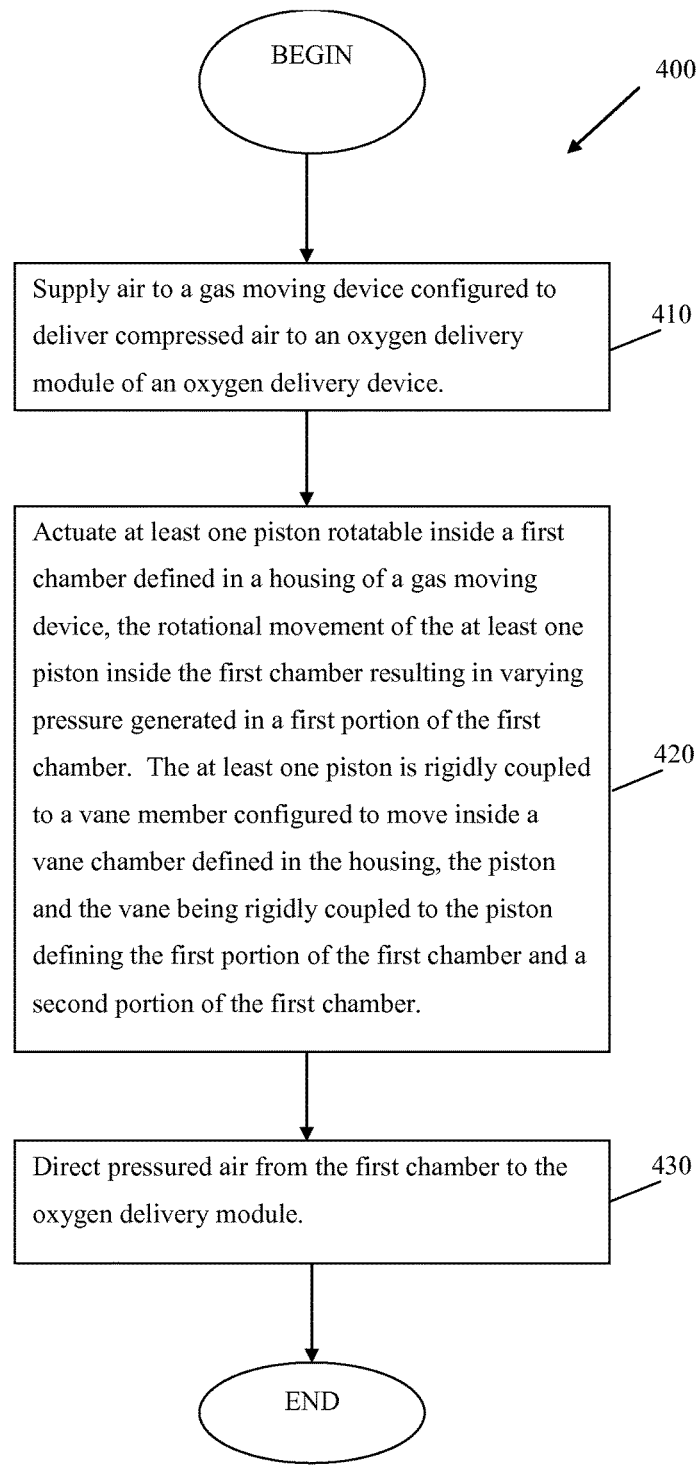
FIG. 5 is a flow chart of an example procedure for moving/directing gas in, for example, an oxygen delivery device.

With reference to FIG. 5, a flow chart of an example embodiment of a procedure 400 for moving/directing gas in, for example, an oxygen delivery device is shown. The procedure 400 includes supplying air 410 to a gas moving device configured to deliver compressed air to an oxygen delivery module of an oxygen delivery device. At least one piston rotatable inside a first chamber defined in the housing of the gas moving device is actuated 420, with the rotational movement of the at least one piston inside the first chamber resulting in varying pressure (which may be represented as a periodic function) generated in a first portion of the first chamber. The at least one rotatable piston is rigidly coupled to a vane member configured to move inside a vane chamber defined in the housing, with the piston and the vane rigidly coupled to it defining the first portion of the first chamber and a second portion of the first chamber. Pressured air from the first chamber, generated through the rotation of the at least one piston, is directed 430 to the oxygen delivery module.

In some embodiments, actuation of the at least one piston may include actuating a first piston rotatable inside a first chamber configured to operate as a compressor to draw ambient air into the oxygen delivery module, with the rotational movement of the at least one piston inside the first chamber resulting in compressor pressure created in the first chamber that is represented as a first periodic function, and actuating a second piston inside a second chamber of the housing, with the second chamber configured to operate as a vacuum pump to draw exhaust gas from the oxygen delivery module. The rotational movement of the second piston inside the second chamber results in vacuum pump pressure created in the second chamber that is represented as a second periodic function. The first periodic function representative of the compressor pressure inside the first chamber may be approximately 180° (or some other offset) out of phase relative to the second periodic function representative of the vacuum pump pressure created inside the second chamber such that forces resulting from the rotational movement of the first piston in the first chamber destructively interfere with forces resulting from the rotational movement of the second piston in the second chamber.

3. Concentrator

With reference again to FIG. 1B, in some embodiments, the oxygen delivery module (also referred to herein as "concentrator") 114 is an Advanced Technology Fractionator (ATF) that may be used for medical and industrial applications. The ATF may implement a pressure swing adsorption (PSA) process, a vacuum pressure swing adsorption (VPSA) process, a rapid PSA process, a very rapid PSA process, or other processes. If a PSA process is implemented, the concentrator may include a rotating valve or a non-rotating valve mechanism to control air flow through multiple sieve beds. Examples of ATF concentrators are shown and described in U.S. Pat. Nos. 5,268,021, 5,366,541, Re. 35,099, which are hereby incorporated by reference in their entireties as though set forth in full.

Although an ATF concentrator 114 is used in the implementations described herein, other types of concentrators or air-separation devices may be used such as, but not by way of limitation, membrane separation types and electrochemical cells (hot or cold). Use of other types of concentrators or air-separation devices may require modifications of some aspects described herein. For example, if the air-separation device is a membrane separation type, pumps other than a compressor may be used to move air through the system.

The ATF's used in the implementations described herein are significantly smaller than prior art implementations. It is noted that reducing the size of the ATF concentrator 114 not only makes the system 100 (depicted in FIGS. 1A and 1B) smaller and more portable, but also improved the recovery percentage, i.e., the percentage of oxygen gas in air that is recovered or produced by the concentrator 114, as well as the productivity (liters per minute/lb. of sieve material) of the concentrator 114. Reducing the size of the ATF decreases the cycle time for the device. As a result, productivity is increased.

Further, use of finer sieve materials also increases recovery rates and productivity. The time constant to adsorb unwanted gases is smaller for finer particles at least partly because the fluid path is shorter for the gases than for larger particles. An example of a sieve material that may be used in an ATF concentrator, such as the concentrator 114, is described in U.S. Pat. No. 5,413,625, which is incorporated by reference in its entirety as though set forth in full. In some embodiments, the sieve material may be a LithiumX Zeolite that allows for a high exchange of Lithium ions. The bead size may, for example, be 0.2-0.6 mm. In some embodiments, the Zeolite may be in the form of a rigid structure such as an extruded monolith or in the form of rolled up paper. In such embodiments, the Zeolite structure would allow for rapid pressure cycling of the material without introducing significant pressure drop between the feed and product streams.

The size of the concentrator 114 may vary with the flow rate desired. For example, the concentrator 114 may come in a 1.5 Liter per minute (LPM) size, a 2 LPM size, a 2.5 LPM size, a 3 LPM size, etc.

The oxygen gas generator 102 may also include an oxygen source in addition to the concentrator 114 such as, but not by way of limitation, a high-pressure oxygen reservoir.

An ATF valve controller 133 (depicted schematically in FIG. 1B) may be integral with or separate from the control unit 110 and may be coupled with valve electronics in the concentrator 114 for controlling the valve (s) of the concentrator 114.

The concentrator may have one or more of the following energy saving modes: a sleep mode, a conserving mode, and an active mode. Selection of these modes may be done manually by the user 108 or automatically based on data determined using the one or more sensors 106 and control unit 110.

Figure 7A:
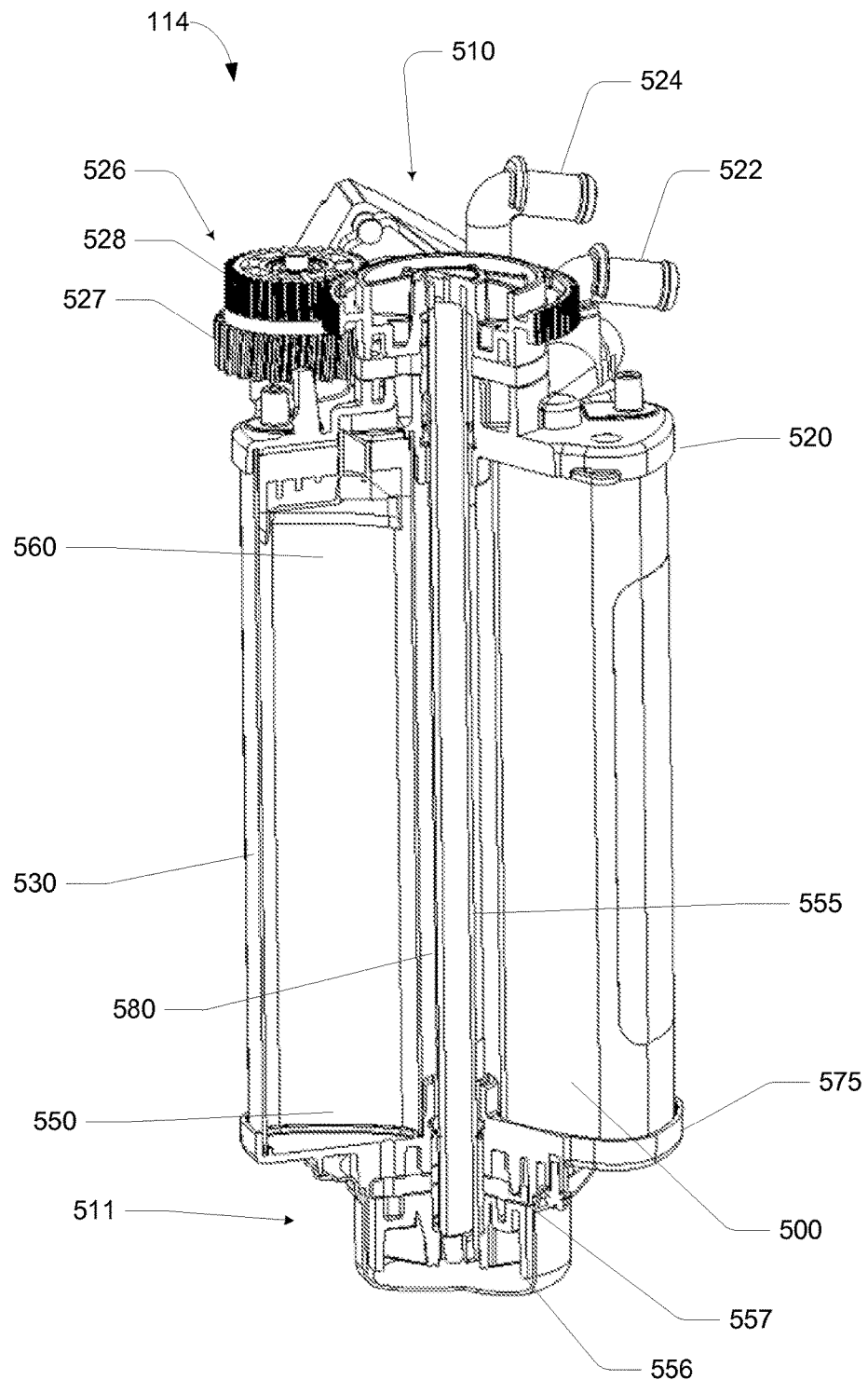
FIG. 7A is a perspective, cut-away view of an example oxygen delivery module (concentrator) that may be used with an oxygen delivery device.
Figure 7B:
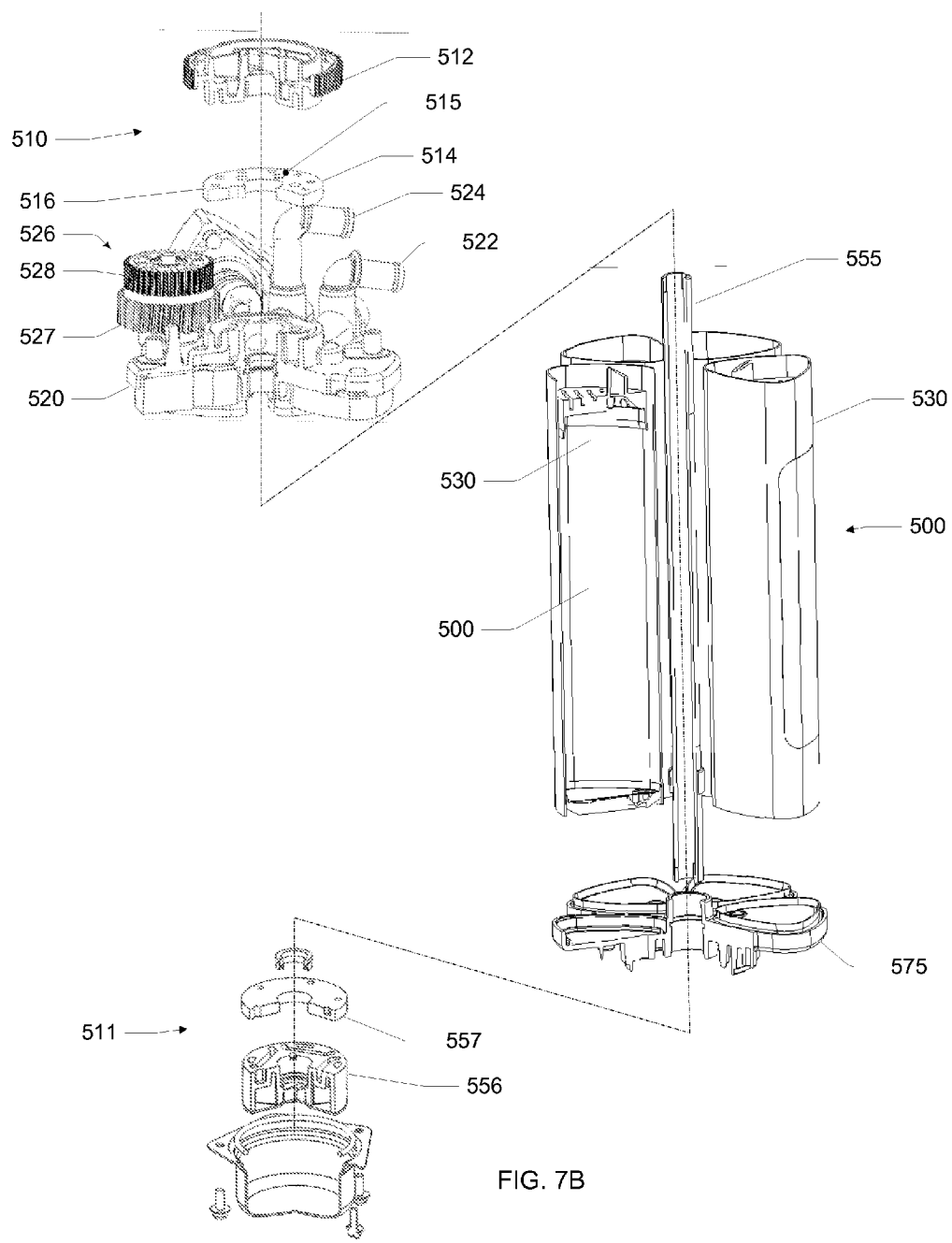
FIG. 7B is a perspective, exploded view of the concentrator illustrated in FIG. 7A.

With reference to FIGS. 7A and 7B, an example embodiment of a concentrator 114 that may be used in the oxygen generator 102 will now be described in more detail. Although the concentrator 114 will be described as separating oxygen from air, it should be noted that the concentrator 114 may be used for other applications such as, but not by way of limitation, air separations for the production of nitrogen, hydrogen purification, water removal from air, and argon concentration from air. As used herein, the term "fluids" includes both gases and liquids.

The concentrator 114 includes numerous improvements over previous concentrators that result in increased recovery of the desired component and increased system productivity. Improved recovery is important since it is a measure of the efficiency of the concentrator. As a concentrator's recovery increases, the amount of feed gas required to produce a given amount of product decreases. Thus, a concentrator with higher recovery may require a smaller feed compressor (e.g., for oxygen concentration from air) or may be able to more effectively utilize feed gas to recover valuable species (e.g., for hydrogen purification from a reformate stream). Improved productivity is important since an increase in productivity relates directly to the size of the concentrator. Productivity is measured in units of product flow per mass or volume of the concentrator. Thus, a concentrator with higher productivity will be smaller and weigh less than a concentrator that is less productive, resulting in a more attractive product for many applications. Therefore, concentrator improvements in recovery, productivity, or both are advantageous.

As shown in FIG. 7A, the concentrator 114 includes, in some embodiments, multiple (e.g., five) adsorption beds 500, each containing a bed of adsorbent material which is selective for a particular molecular species of fluid or contaminant, two rotary valve assemblies 510, 511 for selectively transferring fluids through the adsorption beds 500, and an integrated tube-assembly and manifolds 520/530/575.

The adsorption beds 500 are, in some implementations, straight, elongated, noncircular vessels. The beds may also have circular cross sections. The adsorption beds 500 are surrounded by the metal cover 530 to provide structural support and to mitigate the detrimental effects of water influx that occur when adsorbents are exposed to ambient moisture. The adsorption bed vessels are capped by the manifolds 520 and 575.

Each adsorption bed 500 may include a product end 550 and a feed end 560. The product ends 550 of the beds 500 communicate with product passages (not shown in FIGS. 7A and 7B) of a product manifold 575 for communication with the rotary valve assembly 511. The feed ends 560 of the beds 500 communicate with incoming and outgoing gas passages (not shown) of the feed manifold 520 for communication with the rotary valve assembly 510.

The feed manifold 520 may also include an incoming feed passage that communicates the rotary valve assembly 510 with a feed pressure line 524, and a vacuum chamber that communicates the rotary valve assembly 510 with a vacuum pressure line 522. A product delivery line, communicates with the low pressure reservoir 129. The vacuum pressure line may communicate directly or indirectly with the vacuum generator 124 for drawing exhaust gas from the concentrator 114. Mounted on the manifold 520 is a compound gear 526 that includes a lower gear 527 (e.g., a worm type gear) for engaging with a worm gear on the motor shaft, and an upper gear 228 (e.g., a spur type gear) for engaging with the rotary valve.

In operation, air flows from the compressor 112 to the feed pressure line 524, and through the incoming feed passage of the feed manifold 520. From there, air flows to the feed rotary valve assembly 510 where it is distributed back through outgoing feed passages of the feed manifold 520. From there, the feed air flows to the feed ends 560 of the adsorption beds 500.

The adsorption beds 500 include adsorbent media that is appropriate for the species that will be adsorbed. For oxygen concentration, packed particulate adsorbent material may be used that adsorbs, for example, nitrogen relative to oxygen in the feed air so that oxygen is produced as the non-adsorbed product gas. Thus, in some embodiments, an adsorbent such as a highly Lithium exchanged X-type Zeolite may be used. A layered adsorbent bed that contains two or more distinct adsorbent materials may also be used. As an example, for oxygen concentration, a layer of activated alumina or silica gel used for water adsorption may be placed near the feed end 560 of the adsorbent beds 500 with a lithium exchanged X-type zeolite used as the majority of the bed toward the product end 550 to adsorb nitrogen. The combination of materials, used correctly, may be more effective than a single type of adsorbent. In alternative embodiments, the adsorbent may be a structured material and may incorporate both the water adsorbing and nitrogen adsorbing materials.

The resulting product oxygen gas flows towards the products ends 550 of the adsorption beds 500, through the product manifold 575, product port plate 557, and to the product rotary valve 556. It then redirected by the product rotary valve 556 and product port plate 557 into other passages of the product manifold 575 and directed via the outgoing product passage and into a low pressure reservoir 129. From the low pressure reservoir 129, oxygen gas is supplied to the user (e.g., the user 108 in FIG. 1A) through the supply line 121.

With reference to FIG. 7B, a diagram of an example embodiment of the feed rotary valve assembly 510 is shown. The rotary valve assembly 510 includes a feed rotary valve shoe or disk 512 and a feed valve port plate (or disk) 514. The feed rotary valve shoe 512 and feed valve port plate 514 both have, in some implementations, a circular shape, and may be made from a durable material such as, for example ceramic or engineering thermoplastic, which can be ground to a highly polished flat finish to enable the faces of the feed valve shoe 512 and feed valve port plate 514 to form a fluid-tight seal when pressed together.

The feed rotary valve shoe 512 and the product rotary valve shoe 556 may have a flat, bottom engagement surface and a smooth cylindrical sidewall. The feed valve shoe 512 and the product rotary valve shoe 556 may have several symmetrical arcuate passages or channels cut into the engagement surface, all of which may have as their center the geometric center of the circular engagement surface. The passages or channels include opposite high-pressure feed channels, equalization channels, opposite low-pressure exhaust passages, circular low-pressure exhaust groove which communicates with exhaust passages, opposite product delivery channels, opposite purge channels, a high-pressure central feed passage, a first annular vent groove, and a second annular vent groove.

The feed valve port plate 514 and product valve port plate 557 generally have a flat engagement surface 515, configured to engage the flat engagement surface of the opposing rotary valve shoe, and a smooth disc-shaped (cylindrical sidewall) body 516. An underside of the valve port plates 514 may be disposed on a manifold gasket (not shown). The valve port plates 514, 557 also includes multiple sets of generally symmetric concentrically disposed ports or openings aligned with openings in the manifold gasket to communicate the ports in the plates 514, 557s with the passages in the respective manifolds 520 and 575. The ports extend vertically through the valve port plate 514, 557 in a direction generally substantially perpendicular to the engagement surface 515. In some embodiments, the ports may extend through the valve port plate 51, 5574 in an angular direction toward the engagement surface 515. Generally, all of the ports of each concentric set have the same configuration.

As noted, in some embodiments, the feed valve port plate 514 and the product valve port plate 557 may include multiple concentric sets of ports concentrically disposed at various radii from the geometric center of the feed valve port plate 514 and product valve port plate 557. For example, in some implementations, one set of ports may be configured to communicate with the vacuum chamber of the manifold 520 and the exhaust gas grooves of the valve shoe 512. Another set of ports (which, in some embodiments, includes five round ports) corresponds to the outgoing feed ports that are concentrically disposed at a second radius from the geometric center of the valve port plate 514, and communicate with outgoing feed passages of the manifold 520, the feed channels of the valve shoe 512, and the vacuum ports via the exhaust passages of the valve shoe 512. Another set of ports are incoming product ports that communicate with the incoming product passages of the product manifold 575, the equalization channels of the product valve shoe 556, the purge channels of the product valve shoe 556, and the product delivery channels.

Within the channels of the product valve shoe there may be passages that allow for fluid communication between adsorption beds. This fluid communication may be for the purposes of purge, product delivery, or equalization. Said passages may pass substantially perpendicular to the face of the valve shoe or though the cylindrical sidewall so as to be in fluid communication with one or more channels.

A round central incoming feed port may also be included on the feed port plate 514 to communicate with the incoming feed passage of the feed manifold 520 and the central feed passage of the feed rotary valve shoe 512. Additional sets of ports on the feed port plate 514 of the rotary valve 510 may be included.

In the rotary valve assemblies 510 and 511 described above, a maximum of 1 PSI pressure drop occurs through any port of the valve assembly 510 when the system is producing 3 LPM of oxygen product. At lesser flows, the pressure drop is negligible.

In some embodiments, when in operation, a rotary valve such as the rotary valve 510 depicted in FIGS. 7A and 7B may stop in a position that creates a continuous open passage allowing ambient air to come into contact with adsorbent material in the adsorbent beds of an oxygen delivery module (e.g., an oxygen delivery module implemented as a pressure swing adsorption, or PSA, a vacuum pressure swing adsorption system, or VPSA, etc.) In such situations, the size of the diffusion pathway may not be sufficient to prevent atmospheric moisture from contaminating the adsorbent. Hence, in such circumstances, it may be useful to control the stopping of the valve such that as the valve stops the position of the valve prevents such an open passage and thus atmospheric moisture cannot reach the adsorbent, for instance, when the PSA system is not operating. Therefore, a controller, such as the controller 119 depicted in FIG. 1B, may be configured to perform a shutdown sequence so as to control one or more rotary valves of the system such that when the valve shuts down inadvertent communication with a source of moist air can be avoided. In some implementations, one or both of a rotary encoder or shaft position indicator, for example, may be included and positioned in proximity to the rotary valve or shaft and operatively coupled to the controller, which in turn can control the functioning of the rotary valve. Under these circumstances, the sieve in the VPSA or PSA module may be isolated from ambient moisture, thereby increasing module life.

Thus, in some embodiments, an oxygen delivery device may be provided that includes an oxygen delivery module to produce at least concentrated oxygen. As noted, examples of such an oxygen delivery module include, for example, a pressure swing adsorption system (PSA), a vacuum-pressure swing adsorption system (VPSA), vacuum swing adsorption system (VSA), etc. The oxygen delivery module includes one or more adsorbent beds configured to selectively adsorb corresponding materials from fluid directed through the one or more adsorbent beds, a rotary valve for selectively transferring the fluid through the one or more adsorbent beds, and one or more position sensors to determine a value representative of the rotational position of the rotary valve. The oxygen delivery device may further include (in addition to the oxygen delivery module) a controller configured to, in response to termination of operation of the oxygen delivery module, cause actuation of the rotary valve (e.g., using a stepper motor, which may separate and independent from other motors included with the device that drive other units/components of the device), based on the data determined by the one or more position sensors, to rotate the rotary valve to a position where passages between ambient air and the one or more adsorbent beds are closed so as to prevent atmospheric moisture from reaching the one or more adsorbent beds.

Figure 8:
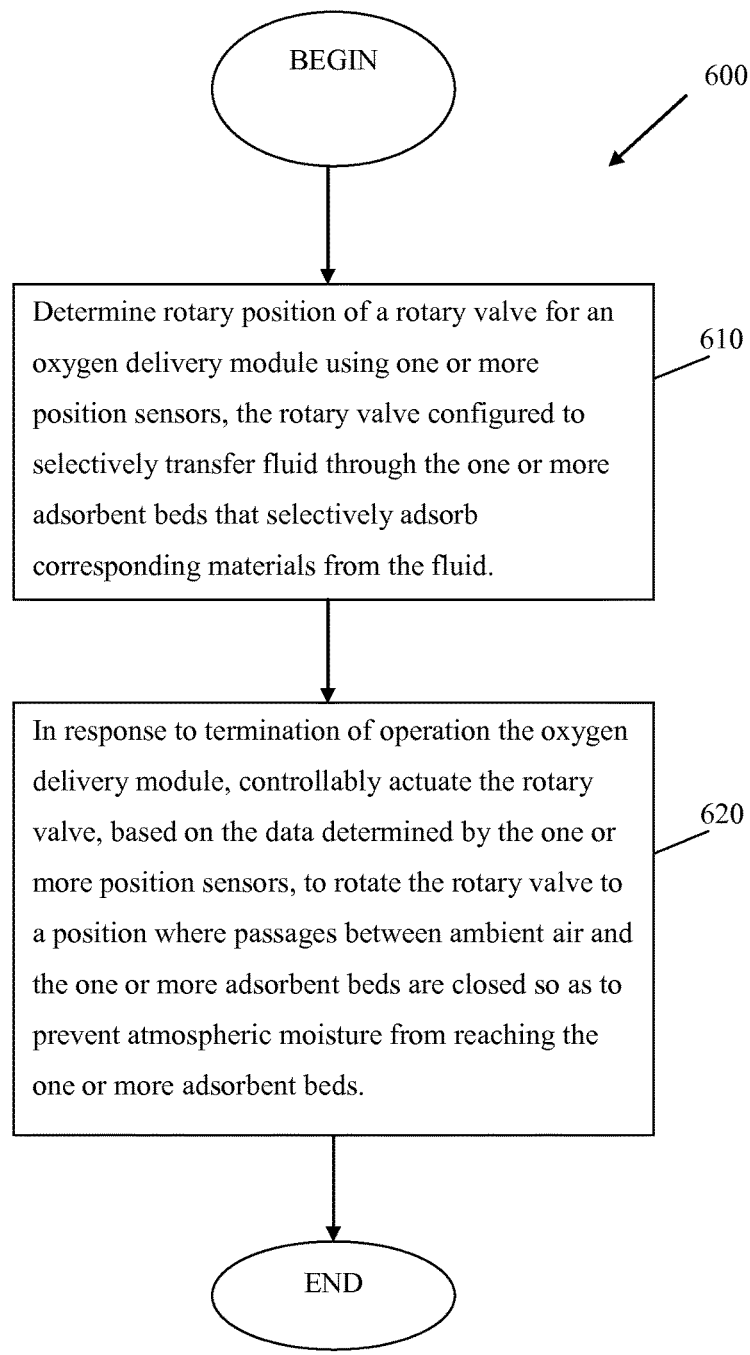
FIG. 8 is a flow chart of an example embodiment of a procedure to control fluid flow into an oxygen delivery device.

With reference to FIG. 8, a flow chart of an example embodiment of a procedure 600 to control fluid flow into an oxygen delivery device is shown. The procedure 600 includes determining 610 rotary position of a rotary valve (such as, for example, the rotary valves 510, 511 shown in FIG. 7B) for an oxygen delivery module using one or more position sensors, with the rotary valve being configured to selectively transfer fluid through the one or more adsorbent beds that selectively adsorb corresponding materials from the fluid. In response to termination of operation of the oxygen delivery module, the rotary valve is controllably actuated 620, based on the data determined by the one or more position sensors, to rotate the rotary valve to a position where passages between ambient air and the one or more adsorbent beds are closed so as to prevent atmospheric moisture from reaching the one or more adsorbent beds. In some embodiments, the one or more position sensors may include at least one of, for example, a rotary encoder, and/or a shaft position indicator, which may be placed proximate one or more of, for example, the rotary valve, and/or a shaft coupled to the rotary valve.

Figure 9:
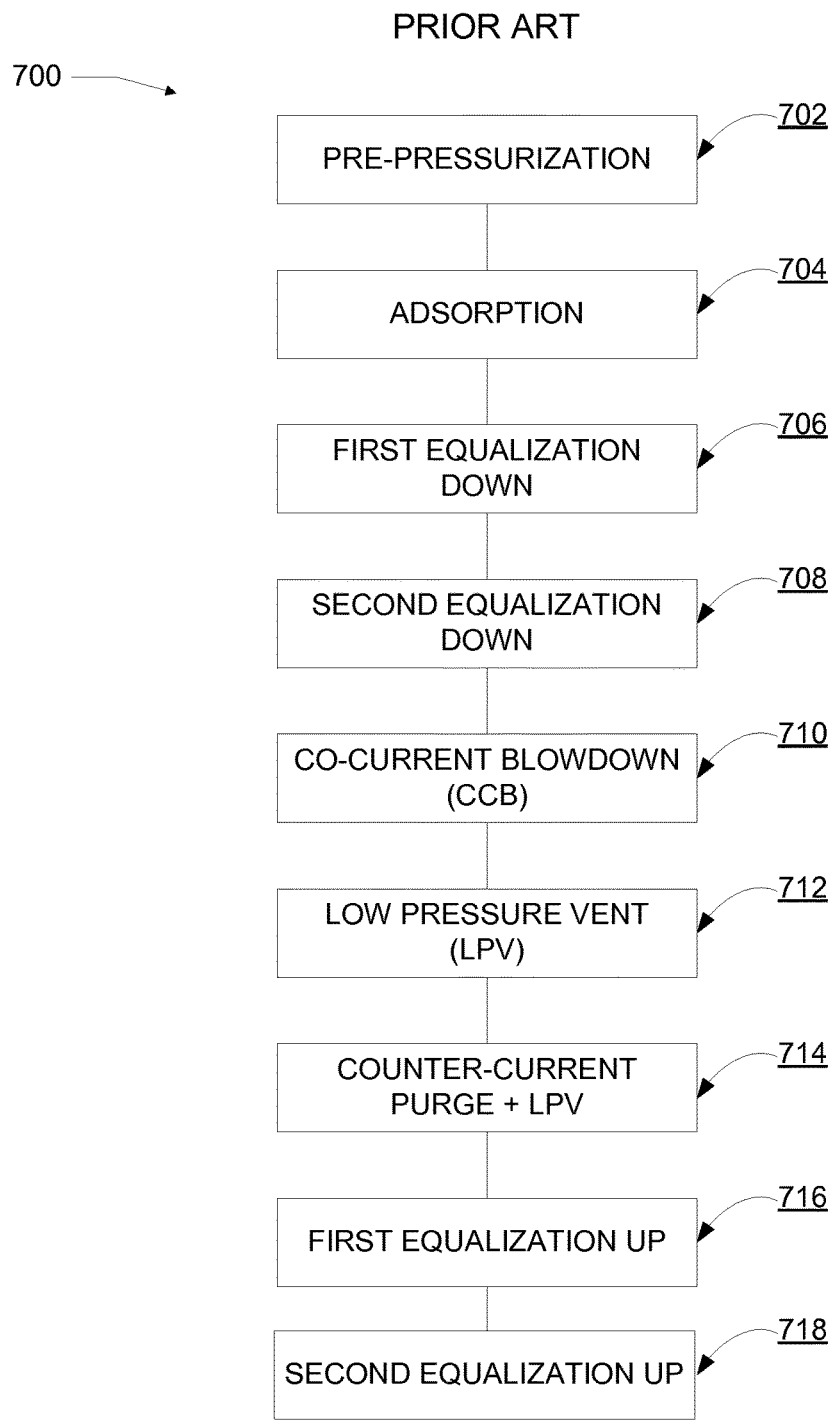
FIG. 9 is a flow chart of an example process cycle for the concentrator illustrated in FIGS. 7A and 7B.

Operations of the oxygen delivery module will now be described. With reference additionally to FIG. 9, showing a flow diagram of an example embodiments of a process 700 performed in the course of a single pressure swing adsorption cycle of an oxygen delivery module, such as the concentrator 114. During use, the rotary valve shoes 512, 556 rotates with respect to the valve port plates 512, 557 so that the cycle described below is sequentially and continuously established for each adsorption bed 500. The speed of rotation of the feed valve shoe 512 and product valve shoe 556 with respect to the feed port plate 514 and product port plate 557 may be varied alone, or in combination with a variable-speed compressor, in order to provide the optimal cycle timing and supply of ambient air for a given production of product. With each revolution of the valve shoes 512 and 556, the adsorption beds 500 undergo two complete cycles. For each cycle, the stages/operations include: 1) pre-pressurization 702, 2) adsorption 704, 3) first equalization down 706, 4) second equalization down 708, 5) co-current blowdown 710, 6) low-pressure venting 712, 7) counter-current purge and low-pressure venting 714, 8) first equalization up 716, and 9) second equalization up 718. The following description of the cycle is provided with respect to one of the multiple adsorbent beds 500 of the oxygen delivery module. Additional details regarding this procedure, as well as configurations and implementations of oxygen delivery devices with respect to which the process 700 is performed are provided, for example, in U.S. Pat. No. 6,691,702, entitled "Portable oxygen concentration system and method of using the same," the content of which is hereby incorporated by reference in its entirety.

During pre-pressurization 702, air flows from the compressor 112 to the feed pressure line, through the incoming feed passage of the feed manifold 520. From there, air flows through the central incoming feed port of the feed port plate 514, through the central feed passage and out the feed channels of the feed valve shoe 512, through the outgoing feed ports, and through outgoing feed passages of the feed manifold 520. From there, the feed air flows to the feed ends 560 of the adsorption beds 500. Because the feed channel is advanced with respect to the product delivery channel (i.e., initially the feed channel is in communication with outgoing feed port and the product delivery channel is blocked, and is not in communication with the incoming product port), the feed end 560 of the adsorption bed 500 is pressurized with feed gas, i.e., pressurized, prior to the commencement of product delivery. In alternative embodiments, the product end 550 may be pre-pressurized with product gas, or the product end 550 may be pre-pressurized with product gas and the feed end 560 may be pre-pressurized with feed gas.

At the adsorption stage 704, because the product delivery channel is in communication with the incoming product port, adsorption of Nitrogen occurs in the bed 500 and the resulting product oxygen gas flows towards the product ends 550 of the adsorption beds 500, through the product lines, and through incoming product passages of the product manifold 575. From there, oxygen gas flows through the incoming product port, into and out of the product delivery channel, through outgoing product port, through the outgoing product passage, and into the low pressure oxygen reservoir 129. From the low pressure oxygen reservoir 129, oxygen gas is supplied to the user 108 through the supply line 121 (shown in FIG. 1B).

In the first equalization-down stage 706, the product end 550 of the bed 500, which is at a high pressure, is equalized with the product end of another bed, which is at a low pressure, to bring the product end 550 of the bed 500 to a lower, intermediate pressure. The product ends 550 communicate through the equalization channels of product valve 556, passages of product port plate 557 and passages of product manifold 575. During the stage 706 and the equalization stages 708, 716, and 718, more particularly described below, the adsorption beds 500 may be equalized at either the feed end 560, the product end 550, or a combination of the feed end 560 and the product end 550.

During the second equalization-down stage 708, the product end 550 of the bed 500, which is at an intermediate pressure, is equalized with the product end of another bed, which is at a lower pressure, to bring the product end 550 of the bed 500 further down to an even lower pressure than in stage 706. Similar to the first equalization-down stage 706, the product ends 550 communicate through equalization channels of product valve 556, passages of product port plate 557 and passages of product manifold 575.

In the co-current blowdown ("CCB") stage 710, oxygen enriched gas produced from the product end 550 of the adsorption bed 500 is used to purge a second adsorption bed 500. Gas flows from the product side of the adsorption bed 500, through passages of product port plate 557 and passages of product manifold 575. The gas further flows through purge channels and purge passages, of the product valve shoe 556, through the purge channel, through the incoming product port, through the incoming product passage, through the product line, and into the product end 550 of adsorption bed 500 to serve as a purge stream. In alternative embodiments, during stage 710 and the following stage 712, co-current blowdown may be replaced with counter-current blowdown.

In the low-pressure venting ("LPV") stage 712, the adsorption bed 500 is vented to low pressure through the feed end 560 of the adsorption bed 500. The vacuum in the exhaust groove of the feed rotary valve shoe 512 communicates with the exhaust passage and the feed end 560 of the adsorption bed 500 (via the outgoing feed port and outgoing feed passage) to draw the regeneration exhaust gas out of the adsorption bed 500. The low pressure venting step 712 occurs without introduction of oxygen enriched gas because the exhaust passage is in communication with the outgoing feed port and the purge channel is not in communication with the incoming product port.

In the counter-current purge and low-pressure venting ("LPV") stage 714, oxygen enriched gas is introduced into the product end 550 of the adsorption bed 500 in the manner described above in stage 710 concurrently with the feed end 560 of the adsorption bed 500 being vented to low pressure as was described in the above step 712. Counter-current purge is introduced into the product end 550 of the adsorbent bed 500 through fluid communication with the product end 550 of a second adsorption bed 500. Oxygen enriched gas flows from the product end 550 of the second adsorption bed 500 through passages of product port plate 557 and passages of product manifold 575. The gas further flows through purge channels and purge passages, of the product valve shoe 556 through the purge channel, through the incoming product port, through the incoming product passage, through the product line, and into the product end 550 of adsorption bed 500. Because the exhaust passage is also in communication with the outgoing feed port during the stage 714, oxygen enriched gas flows from the product end 550 to the feed end 560, regenerating the adsorption bed 500. The vacuum in the exhaust groove of the feed rotary valve shoe 512 communicates with the exhaust passage and the feed end 560 of the adsorption bed 500 (via the outgoing feed port and outgoing feed passage) to draw the regeneration exhaust gas out of the adsorption bed 500. From the exhaust passage, the exhaust gas flows through the vacuum ports, into the vacuum chamber, and out the vacuum pressure line. In alternative embodiments, the vacuum may be replaced with a low-pressure vent that is near atmospheric pressure or another pressure that is low relative to the feed pressure. In some embodiments, product gas from the low pressure oxygen reservoir 129 is used to purge the product end 550 of the adsorbent bed 500.

In the first equalization-up stage 716, the product end 550 of the bed 500, which is at a very low pressure, is equalized with the product end of another bed, which is at a high pressure, to bring the adsorption bed 500 to a higher, intermediate pressure. The product ends 550 communicate through the equalization channels of product valve 556, passages of product port 557 and passages of product manifold 575.

In the second equalization-up stage 718, the product end 550 of the bed 500, which is at an intermediate pressure, is equalized with the product end of another bed, which is at a higher pressure, to bring the product end 550 of the bed 500 further up to an even higher pressure than in stage 716. Similar to the first equalization-down stage 706, the product ends 550 communicate through equalization channels of product valve 556, passages of product port plate 557 and passages of product manifold 575.

It should be noted that in some embodiments, the combined duration of feed stages 702, and 704 may be substantially the same as the combined duration of purge stages 710, 712, and 714, which may be substantially three times the duration of each equalization stage 706, 708, 716, and 718. In alternative embodiments, the relative duration of the feed stages 702, and 704, the purge stages 710, 712, 714, and each of the equalization stages 706, 708, 716, and 718 may vary.

After the second equalization-up stage 718 has been completed, a new cycle begins in the adsorption bed 500 starting with the pre-pressurization step 702.

The example five-bed concentrator 114 described herein, and the cycle of example process 700 described herein, have a number of advantages over conventional concentrators and associated cycle processes employed in the past. The multiple equalization stages 716, and 718 at the product ends 550 and the pre-pressurization stage 702 contribute to the pre-pressurization of the adsorption beds 500 prior to product delivery. As a result, the beds 500 reach their ultimate pressure (substantially equal to the feed pressure) quickly, and thus enable maximum utilization of the adsorbent media. Additionally, pre-pressurizing the adsorbent beds 500 allows product to be delivered at substantially the same pressure as the feed, thus retaining the energy of compression in the stream, which makes the product stream more valuable for use in downstream processes. In alternative embodiments, pre-pressurizing the beds 500 with product before exposing the feed end 560 of the bed 500 to the feed stream substantially eliminates any pressure drop experienced due to the fluid interaction or fluid communication between two or more adsorbent beds 500 on the feed end 560. Additionally, compared to systems with greater numbers of beds, use of a 5-bed system, such as the system described herein, reduces the duration and number of beds that are in fluid communication with the feed channels at the same time, thus reducing the propensity for fluid flow between adsorption beds. Because fluid flow between adsorption beds is associated with a reversal of the flow direction in the higher pressure bed (resulting in decreased performance), reduction of this effect is advantageous.

A further advantage of a 5-bed system over other commercial systems is that it includes a small number of adsorption beds 500, allowing the concentrator to be relative small, compact, and light-weight, while delivering sufficient flow and purity and maintaining high oxygen recovery. Other oxygen delivery modules (PSA systems), e.g., typically those with a small number of adsorption beds, result in deadheading the compressor (thus resulting in high power use) during a portion of the cycle. Deadheading the compressor eliminates detrimental flow between the feed side 560 of the two or more adsorption beds 500 but increases system power. 5-bed system eliminates compressor deadheading and minimizes performance-limiting feed side 560 flow between adsorbent beds 500.

Use of the multiple pressure equalization stages 706, 708, 716, and 718 reduces the amount of energy of compression required to operate the concentrator 114. Equalizing the beds 500 conserves high-pressure gas by moving it to another bed 500 rather than venting it to the atmosphere or to a vacuum pump. Because there is a cost associated with pressurizing a gas, conserving the gas provides a savings and improves recovery. Also, because a bed 500 may contain gas enriched with product, usually at the product end 550 of the bed 500, allowing this gas to move into another bed 500, rather than venting it, conserves product and improves recovery. The number of equalizations is, in some embodiments, between one and four. It should be noted that each equalization process represents two equalization stages, namely, an equalization-down stage and an equalization-up stage. Thus, two equalizations means two down equalizations and two up equalizations, or four total equalizations. The same is true for other-number equalizations. In some embodiments, one to four equalizations processors (two to eight equalization stages) are used in each cycle. In some embodiments, one to three equalizations processes (two to six equalization stages) are used in each cycle. In some embodiments, two equalizations processes (four equalization stages) are used in each cycle.

In alternative embodiments, the concentrator 114 may have other numbers of adsorption beds 500 based on the concentration of the feed stream, the specific gases to be separated, the implementation of the pressure swing adsorption cycle, and operating conditions. For example, but not by way of limitation, under some circumstances it may be advantageous to use four-bed concentrators or six-bed concentrators. When operating a cycle similar to that described above with a four-bed concentrator, the problem of fluid communication between the feed channels and more than one adsorption bed (at one instant) is generally eliminated. When the feed-end fluid communication is eliminated, the feed stages 702, and 706 (depicted in FIG. 9) occur in a more desirable fashion resulting in improved recovery of the desired product. The advantages of a six-bed system, compared to a five-bed system, are realized when the pressure-swing cycle described above is modified so that there are three equalization up stages and three equalization down stages instead of two equalization up stages and two equalization down stages. A third equalization is advantageous when the feed gas is available at high pressure. The third equalization conserves compressor energy because it allows the equalized beds to obtain substantially 75% of the feed pressure compared to substantially 67% of the feed pressure when two equalization stages are used. In any PSA cycle, whenever an equalization-up operation/stage occurs, there is a corresponding equalization down operation that needs to be performed. The requirement of matching equalization stages imparts some restrictions on the relative timing of the cycle stages. If, for example, the duration of the feed stage is substantially the same as the duration of each equalization stage then a six-bed cycle would provide the required matching of equalization stages.

B. Energy Source and Communication Functionality

To properly function as a lightweight, portable system, the system 100 schematically depicted in FIG. 1A needs to be energized by a suitable energy source, such as the energy source 104 shown in FIG. 1A. In some embodiments, the energy source 104 may include a rechargeable battery such as a lithium-ion type rechargeable battery. In some implementations, the system 100 may be powered by a portable energy source other than a lithium-ion battery. For example, a rechargeable or renewable fuel cell may be used. Although the system is generally described as being powered by a rechargeable battery, the system 100 may be powered by multiple batteries. Thus, as used herein, the word "battery" includes one or more batteries. Further, a rechargeable battery constituting at least part of the energy source 104 may comprise one or more internal and/or external batteries. The energy source (also referred to as a battery module when the energy source includes a battery) may be removable from the system 100. In some embodiments, the system 100 may use a standard internal battery, a low-cost battery, an extended-operation internal battery, and an external secondary battery in a clip-on module. Thus, in some embodiments, an oxygen delivery device, such as the system 100, may include an internal battery to power, at least partly, the oxygen delivery device. In such implementations, the internal battery located within a housing of the oxygen delivery device. The oxygen delivery device may also include an external battery pack secured to the housing of the oxygen delivery device to supplement power requirements of the oxygen delivery device.

In some implementations, the system 100 may have a built-in adapter including battery charging circuitry 130 and one or more plugs 132 (both depicted schematically in FIG. 1B) configured to allow the system 100 to be powered from a DC power source (e.g., car cigarette lighter adapter) and/or an AC power source (e.g., home or office 110 VAC wall socket) while a battery-based energy source 104 is simultaneously being charged from the DC or AC power source. The adapter or charger could also constitute separate accessories. For example, the adapter may be a separate cigarette lighter adapter used to power the system 100 and/or charge the battery in an automobile. A separate AC adapter may be used to convert the AC from an outlet to DC for use by the system 100 and/or charge the battery. Another example of an adapter may be an adapter used with wheel chair batteries or other carts.

In some embodiments, the device may include a power supply, such as an AC/DC power supply which may be external or internal to the device. However, in certain instances, an external power supply may be provided.

Accordingly, in some embodiments, an oxygen delivery device may further include an internal DC/DC power converter placed within a housing of the oxygen delivery device and/or may further include a cart to hold the oxygen delivery device, an AC adapter external to a housing of the oxygen delivery device, with the AC adapter being mounted on the cart. Such a device may also include a battery pack external to the housing of the oxygen delivery device, the battery pack being mounted on the cart.

Power supplies may generate large amounts of heat and can be heavy relative to the total weight of the device. This can cause increased requirements for electrical safety, thus increasing the cost of the overall device. Additionally, an external power supply can get lost and may make the device awkward to transport. Hence, in some embodiments, an AC and/or DC power supply may be mounted inside of a casing of a device, such as within the power bus.

For example, a power supply, such as an internal AC adapter, may be built into a main body, e.g., mounted inside, of the oxygen delivery device. Thus, in such embodiments, an oxygen delivery device may further include an internal AC adapter placed within a housing of the oxygen delivery device. Additionally, in certain embodiments, an internal DC converter, such as a 12V to 24V DC/DC boost converter may be positioned inside the concentrator. In certain instances, a universal power input, along with the necessary electronics to convert voltage from an external source (e.g., AC/DC/Airplane) may be positioned inside of oxygen concentrator. Such a configuration may preclude the need for a separate device that a patient needs to carry around and keep track of. This will prevent the power supply from getting lost and may make the system easier to transport. Accordingly, in such implementations, an oxygen delivery device may be provided that includes a universal power adapter configured to connect to a plurality of power outlet types and to adapt power delivered from the plurality of power outlet types to produce an output power with power characteristics required for operation of the oxygen delivery device. Such a universal power adapter may be disposed within a housing of the oxygen delivery device.

In some embodiments, an oxygen delivery device of the disclosure may include, e.g., in addition to a built in battery, a strap-on battery. For example, in certain embodiments, an internal battery may be included, wherein the battery is of a sufficient in size to handle short trips between location where external power connectable to the oxygen delivery device is available. Although these batteries may be relatively small, in certain instances, they may be relatively large to allow for increased operating time. Such a battery may have a capacity ranging from 40-400 Watt-hours. The physical size of a battery with said capacity would vary dependent on battery chemistry-utilized, but in embodiments utilizing lithium-ion rechargeable cells would occupy a volume of 0.072 to 0.722 liters and weigh 204 to 2.04 kilograms Yet, when a longer operating time on battery is useful, the oxygen delivery device may be connected to an external battery pack to supplement the internal power supply.

In some implementations, an oxygen delivery device may include an indicator configured for displaying actual battery time remaining. Accurate battery capacity can be determined and calibrated, which calibration will allow the device to display actual battery time remaining. This will help a subject to adequately gauge the amount of time until connection to an alternate power source is required. Accordingly, an oxygen delivery device may be provided that includes a user interface including an indicator to indicate time remaining for a battery-based power source included with the oxygen delivery device. Additionally, in some embodiments, the device may include a backup battery that may be employed to power a buzzer and/or an indicator light, such as an LED, which buzzer and/or light may be used to indicate a change in power supply, such as a loss of power.

In some embodiments, the oxygen delivery device may include one or more USB ports. The one or more USB ports may enable configuration of the oxygen delivery device in host/salve arrangements, e.g., a USB interface will allow for data acquisition and transmission to and from the oxygen delivery device, as well as software upgrades while the host interface facilitates further sensor connections. This allows for increased data transferring speed. Accordingly, in some implementations, an oxygen delivery device may be provided that includes a device interface module including one or more universal serial bus (USB) ports to enable the oxygen delivery device to function as one of, for example, a slave and/or a host when connected to at least one external device. The one or more USB ports of the device interface module enable the oxygen delivery device to perform one or more of, for example, communicating data to and from the at least one connected external device, upgrading software-based implemented functionality of at least one operation of the oxygen delivery device, and/or connecting to one or more sensors configured to measure one or more of, for example, environmental conditions, operating conditions of the oxygen delivery device, and a patient's therapeutic conditions.

The oxygen delivery devices described herein may also be configured for interoperability with additional devices. Accordingly, in some implementations, an oxygen delivery device may be provided that includes a device interface module configured to interface with one or more additional devices to enable interoperability functionality of the oxygen delivery device with the one or more additional devices. The interoperability functionality includes one or more of, for example, directing power/energy from a power source of the oxygen delivery device to the one or more additional devices, and/or communicating data between the oxygen delivery device and the one or more additional devices. The one or more additional devices may include one or more of, for example, pulse oximeter, pedometer, mathemoglobin monitor, carboxyhemoglobin monitor, total hemoglobin sensor, a wireless telephone, a wireless modem, a remote computing device, and/or a respiration monitor. The device interface module may include at least one dedicated port to interface with at least one of the one or more additional devices.

The telemetry mechanism (also referred to as a modem or communication module) of the oxygen delivery device may be used to communicate physiological information of the user such as, without limitation, heart rate, oxygen saturation, respiratory rate, blood pressure, EKG, body temperature, inspiratory/expiratory time ratio (I:E ratio) with one or more remote computers. The telemetry mechanism may also be used to communicate other types of information, such as, but not by way of limitation, oxygen usage, maintenance schedules on the system 100, and battery usage, to one or more remote devices (e.g., remote computers).

Because the system 100 is small and light (e.g., 2-15 pounds), the system 100 may simply be lifted from a cradle (where a cradle can be used) and readily be carried, e.g., with a shoulder strap, by an average user to the destination. If the user is unable to carry the system 100, the system 100 may be readily transported to the destination using a cart or other transporting apparatus. Alternatively, in some embodiments, the system 100, where the system includes a built-in adapter, power may be drawn from power sources such as a car cigarette lighter adapter and/or an AC power outlet available at the destination. Further, spare battery packs 104 may be used for extended periods away from standard power sources.

The oxygen delivery device therefore may be operatively coupled to a variety of accessories that require power and/or may be configured (e.g., through programming) to allow the oxygen delivery device to exchange information therewith. For example, the oxygen delivery device may be configured to be coupled to a device for the purpose of receiving information therefrom. Hence, the devices and systems described herein may allow for the collection and/or transmission of clinical data, which can be reported to clinicians, electronic medical record repository, or caregiver. Such information can be processed by the controller so as to optimize the manner in which oxygen is delivered to the subject. Auxiliary devices may include one or more of a pulse oximeter, pedometer, methemoglobin monitor, carboxyhemoglobin monitor, total hemoglobin sensor, wireless phone, wireless modem, and/or respiration monitor and the like. Hence, the power supply of the concentrator may be configured to serve as a power source for one or more of these auxiliary devices.

If the battery pack connected to the energy source 104 includes multiple batteries, the system (oxygen delivery device) 100 may include a battery sequencing mechanism to conserve battery life.

C. Output Sensor

Figure 10:
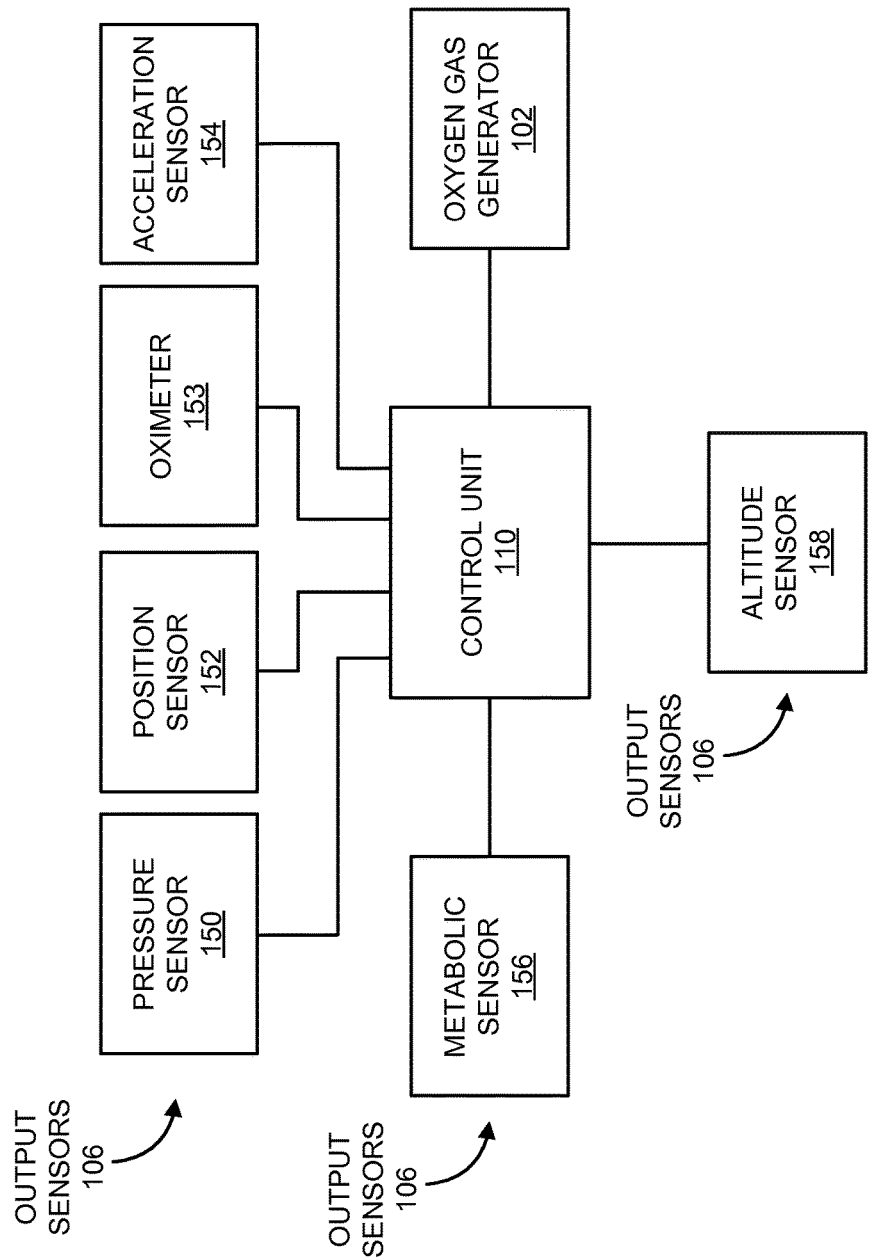
FIG. 10 is a block diagram of one or more sensors that may be used with an oxygen delivery device.

With reference to FIGS. 1A and 1B, and 10, one or more output sensors 106 are used to sense one or more conditions of the user 108, environment conditions, operational conditions of the oxygen delivery device, etc., to determine, among other things, the oxygen flow rate needs of the user and, hence, the oxygen flow rate output requirements for the system 100. The control unit (controller) 110 is linked to the one or more output sensors 106, from which the control unit 110 receives measured/determined data representative of the conditions being sensed. The controller is also linked to the oxygen gas generator 102 to control oxygen generation operations (including operations of the oxygen delivery module, any of the gas moving devices, etc.) in response to the condition(s) sensed by the one or more output sensors 106. For example, the output sensor(s) 106 may include any or all of the activity sensors shown and described in U.S. Pat. No. 5,928,189, which is incorporated herein by reference in its entirety as though set forth in full. These output sensors include, for example, a pressure sensor 150, a position sensor 152, an acceleration sensor 154, as well as a physiological condition or metabolic sensor 156 and an altitude sensor 158.

The first three sensors 150, 152, 154 (and, in certain circumstances, the physiological condition sensor 156) are activity sensors because these sensors provide signals/data representing activity of the user 108. In the delivery of oxygen using a portable oxygen concentration system, it is important to deliver an amount of oxygen gas proportional to the activity level of the user 108 without delivering too much oxygen. Too much oxygen may be harmful for the user 108 and may deplete the energy source 104 (e.g., reduces the life of a battery comprising the energy source 104). The control unit 110 (which, in some embodiments, may be implemented using a programmable processor-based controller) is configured to regulate the oxygen gas generator 102 to control the flow rate of oxygen gas to the user 108 based on the one or more signals representative of the activity level of the user produced by the one or more sensors 106. For example, if the output sensor(s) 106 indicates that the user 108 has gone from an inactive state to an active state, the control unit 110 may cause the oxygen gas generator 102 to increase the flow rate of oxygen gas to the user 108, e.g., by causing the speed of a gas moving device delivering air to the oxygen delivery module of the oxygen gas generator to increase, and/or may provide a burst of oxygen gas to the user 108 from a high-pressure oxygen reservoir. If the output sensor(s) 106 indicates that the user 108 has gone from an active state to an inactive state, the control unit 110 may cause the oxygen gas generator 102 to reduce the flow rate of oxygen gas to the user.

As noted, in some embodiments, the amount of oxygen gas supplied is controlled by controlling the speed of the motor 118 of the gas moving device (compressor) via the variable-speed controller 119 described herein.

Alternatively, or in addition to the variable-speed controller, the supply of oxygen gas may be controlled by the supply valve 160 located in the supply line 121 between the oxygen gas generator 102 and the user 108. For example, the supply valve 160 may be variably movable between at least a first position and a second position, the second position allowing a greater flow of concentrated gaseous oxygen through than the first position. The control unit 110 may cause the supply valve 160 to move from the first position to the second position when one or more of the activity level sensors 152, 154, and 156 sense or determine an active level of activity of the user 108. For example, the control unit 110 may include a timer, and when an active level is sensed for a time period exceeding a predetermined timed period, the control unit 110 causes the valve 160 to move from the first position to the second position.

Examples of pressure sensors 150 include, without limitation, a foot switch that indicates when a user is in a standing position compared to a sedentary position, and a seat switch that indicates when a user is in a seated position compared to a standing position.

A pendulum switch is an example of a position sensor 152. For example, a pendulum switch may include a thigh switch positioned pendulously to indicate one mode when the user is standing, i.e., the switch hangs vertically, and another mode when the user seated, e.g., the thigh switch being raised to a more horizontal position. A mercury switch may be used as a position sensor.

An acceleration sensor 158 such as an accelerometer is another example of an activity sensor that provides a signal representing activity of the user.

The physiological condition or metabolic sensor 156 may also function as an activity sensor. The physiological condition sensor 156 may be used to monitor one or more physiological conditions of the user for controlling the oxygen gas generator 102, or for other purposes. Examples of physiological conditions that may be monitored with the sensor 156 include, but without limitation, blood oxygen level, heart rate, respiration rate, blood pressure, EKG, body temperature, and I to E ratio (the inspiration to expiration ratio). An oximeter, such as the oximeter 153 depicted in FIG. 10, is an example of another sensor to monitor conditions of the patient that may be used in the system 100. The oximeter measures the blood oxygen level of the user, upon which oxygen production may be at least partially based. Other types of sensors to monitor conditions of the patient (e.g., therapeutic conditions) may also be included.

An altitude sensor 158 is an example of an environmental or ambient condition sensor that may sense an environmental or ambient condition upon which control of the supply of oxygen gas to the user may be at least partially based. The altitude sensor 158 may be used alone or in conjunction with any or all of the above sensors, the control unit 110 and the oxygen gas generator 102 to control the supply of oxygen gas to the user in accordance with the sensed altitude or elevation. For example, at higher sensed elevations, where air is less concentrated with oxygen, the control unit may increase the flow rate of oxygen gas to the user 108. At lower sensed elevations, where air is more concentrated, the control unit may decrease the flow rate of oxygen gas to the user 108 or maintain it at a control level. Other types of sensors to monitor environmental conditions that may also impact operation of the oxygen delivery device, e.g., sensors to monitor ambient temperature, may also be coupled to the controller 110, or to another controller.

In some embodiments, the concentrator may be configured for the remote monitoring of peripheral oxygen saturation (SpO2), for instance, so as to provide a closed loop O2 delivery. For example, an oxygen delivery device/concentrator, such as any of the concentrators described herein, may be configured to employ a sensor, such as a pulse oximeter, to monitor a subject's oxygen saturation. The output level of the oxygen delivery device can then be adjusted to deliver a level of oxygen that more precisely meets the needs of the subject given a particular oxygen saturation. For instance, a pulse oximeter may be operatively connected, e.g., via a wired or wireless communications link to the controller, which controller may in turn use data provided by the sensor to control the output level of the oxygen to be delivered so as to be in accordance with a particular oxygen saturation requirement for a subject. Accordingly, in some embodiments, an oxygen delivery device is provided that includes an oxygen delivery module to produce at least concentrated oxygen, and a gas moving device (e.g., a compressor) to deliver air to the oxygen delivery module, with the gas moving device being driven by a motor to actuate the gas moving device. In such embodiments, the oxygen delivery device also includes a communication module to communicate with a remote sensor, e.g., a remote pulse oximeter, configured to determine peripheral oxygen saturation of a patient, and a controller to control operations of at least one of the oxygen delivery module and the gas moving device based, at least in part, on the determined peripheral oxygen saturation, to adjust the oxygen purity level of the oxygen produced by the oxygen delivery module to cause the peripheral oxygen saturation level of the patient to converge to a pre-determined required peripheral saturation level.

For example, an oximeter sensor may be secured to the subject, such as to secure the remote oximeter sensor to the fingertip or earlobe of the subject, and the oximeter may thus be configured to determine the change in light absorbance by the patient's tissue. Particularly, a light, such as a light containing both red and infrared wavelengths, is passed from one side to the other. The change in absorbance of the wavelength is then measured. This will allow for a determination of the light's absorbance due to the pulsing arterial blood alone, exclusive of venous blood, skin, bone, muscle, fat, and the like. Based upon the ratio of the change in absorbance of the red and infrared light caused by the difference in color between oxygen-bound (bright red) and oxygen unbound (dark red) blood hemoglobin, the oxygenation (e.g., % of hemoglobin molecules bound with oxygen molecules) of the blood may be determined. This information may then be communicated, e.g., via wireless communication, to the controller of the oxygen delivery device, which may then adjust the purity and/or flow level of the oxygen being delivered so as to achieve a particular saturation level.

For instance, a target oxygenation (e.g., saturation) level may be input to the controller or otherwise set, e.g., via a user interface, via a communication module receiving data transmitted from a remote location that indicates the target oxygenation level, etc. The pulse oximeter sensor will measure the level of saturation and communicate the determined data to the controller of the oxygen delivery device. If the oxygenation is below the selected level, e.g., 90%, the controller will cause an increase in the level of oxygen (e.g., purity, flow) in the flow being delivered to the subject. The system will then recheck the pulse oxygenation to determine if the desired, saturation has been reached. If not, the process will repeat until the selected oxygenation has been achieved. Once a particularly selected oxygenation level has been achieved, the system may be configured for periodic monitoring of the oxygenation level so as to ensure that level is maintained. In a manner such as this, the amount of time a subject spends at optimal saturation may be regulated so as to help prevent treatment exacerbations and to minimize the amount of power consumed by the oxygen delivery device, thus maximizing battery life.

Figure 11:
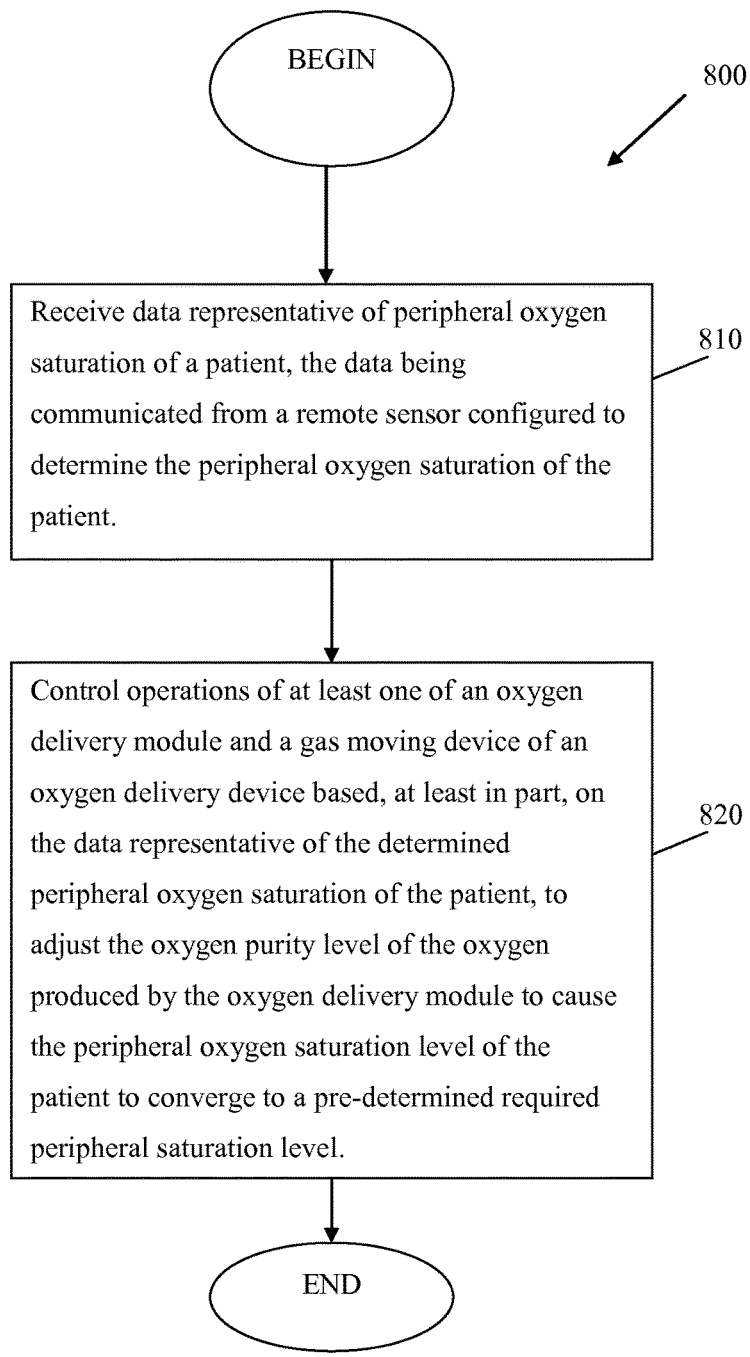
FIG. 11 is a flow chart of an example procedure to control oxygenation level of a patient.

Accordingly, with reference to FIG. 11, a flow chart of an example embodiment of a procedure 800 to control oxygenation level of a patient is shown. The procedure 800 includes receiving 810 data representative of peripheral oxygen saturation of a patient, the data being communicated from a remote sensor (such as a remote pulse oximeter) configured to determine the peripheral oxygen saturation of the patient. Having received the data representative of the peripheral oxygen saturation of the patient, operations of at least one of an oxygen delivery module (e.g., PSA, VPSA, etc.) and a gas moving device (e.g., a compressor) of an oxygen delivery device are controlled based, at least in part, on the data representative of the determined peripheral oxygen saturation of the patient, to adjust the oxygen purity level of the oxygen produced by the oxygen delivery module to cause the peripheral oxygen saturation level of the patient to converge to a pre-determined required peripheral saturation level.

In some implementations, one or more sensors may be provided so as to continuously monitor the breathing pattern of a subject in either pulse dose or continuous flow modes. For instance, when a subject is operating the device in a pulsed dose mode, the controller may be configured (e.g., through computer instructions where the controller is a programmable processor-based device) to determine a subject's breathing and/or ensuring that a pulse of oxygen is delivered periodically in accordance with a predetermined breathing pattern. The controller can also then be employed to determine and ascertain that the desired pulse is in fact delivered. This is important because if the subject does not breathe and/or the desired pulse is not delivered that may mean that the subject might not be getting the oxygen needed. In such an instance, the concentrator may be configured to change modes to continuous flow to ensure that the appropriate level of oxygen is being delivered to the subject.

For example, in some embodiments, such as when a subject is talking, when the cannula has been dislodged, or when a subject breathes through its mouth, an inspiration sensor, e.g., a sensor detecting air pressure, may not be able to detect inspiration. Therefore, by implementing a procedure for continuous flow breath detection, the concentrator can change modes back to pulsed dose mode if it detects that a subject has resumed breathing and it is safe to resume pulse dose mode. This will help to extend operating time on battery, because the pulse dose mode requires less power than does the continuous flow mode of delivery.

For example, if a subject stops breathing or no trigger is sensed, the pulse dose mode that may be activated may be turned off for a period of time to revert to continuous flow, which in turn may be turned off to revert back to pulse dose mode once normal breathing has been detected. Further, such a configuration can help ensure that the subject's saturation level is maintained even when they are talking or breathing from their mouth, such as by sensing the breath in pulse or continuous mode and regulating the delivery accordingly.

Accordingly, in some implementations, an oxygen delivery device is provided that includes an oxygen delivery module (e.g., a pressure swing adsorption system, a vacuum-pressure swing adsorption system, a vacuum swing adsorption system, a membrane separation device, etc.), and at least one sensor to detect patient breathing. In some embodiments, the at least one sensor may include, for example, a pressure sensor fluidly connected to a cannula, coupled to the oxygen delivery module, that is structured to deliver the oxygen from the oxygen delivery module through the patient's nasal passages. The pressure sensor fluidly connected to a cannula is configured to detect pressure changes within the patient's nasal passages, and to generate data representative of the pressure changes.

The oxygen delivery device also includes a controller configured to control the oxygen delivery module to cause the oxygen delivery module to deliver oxygen to the patient based, at least in part, on data from the at least one sensor such that in response to a determination, based on data from the at least one sensor, that no breathing is detected for a first pre-determined period of time, the controller causes the oxygen delivery device to deliver oxygen to the patient in continuous flow mode. The controller is also configured to subsequently (i.e., after switching to the continuous flow mode), in response to a determination, based on data from the at least one sensor, that breathing is detected for a second pre-determined period of time, the controller causes the oxygen delivery device to revert back to pulse mode to thus cause oxygen to be delivered to the patient in a pulse flow mode. In some embodiments, the restoration of pulse mode in oxygen delivery may occur after some pre-determined time period (e.g., 5 minutes, 10 minutes) has elapsed. In some embodiments, determination of when breathing has resume may be performed by processing (filtering) data received from a sensor sensing pressure to determine onset of an inspiratory cycle for the patient. Such filtering may enable early detection/determination of the beginning of the patient's inspiratory cycle, to thus revert to continuous flow mode more expeditiously (which in turn would reduce power consumption requirements). Such filtering may utilize, for example, time averaging methods or low pass methods.

Figure 12:
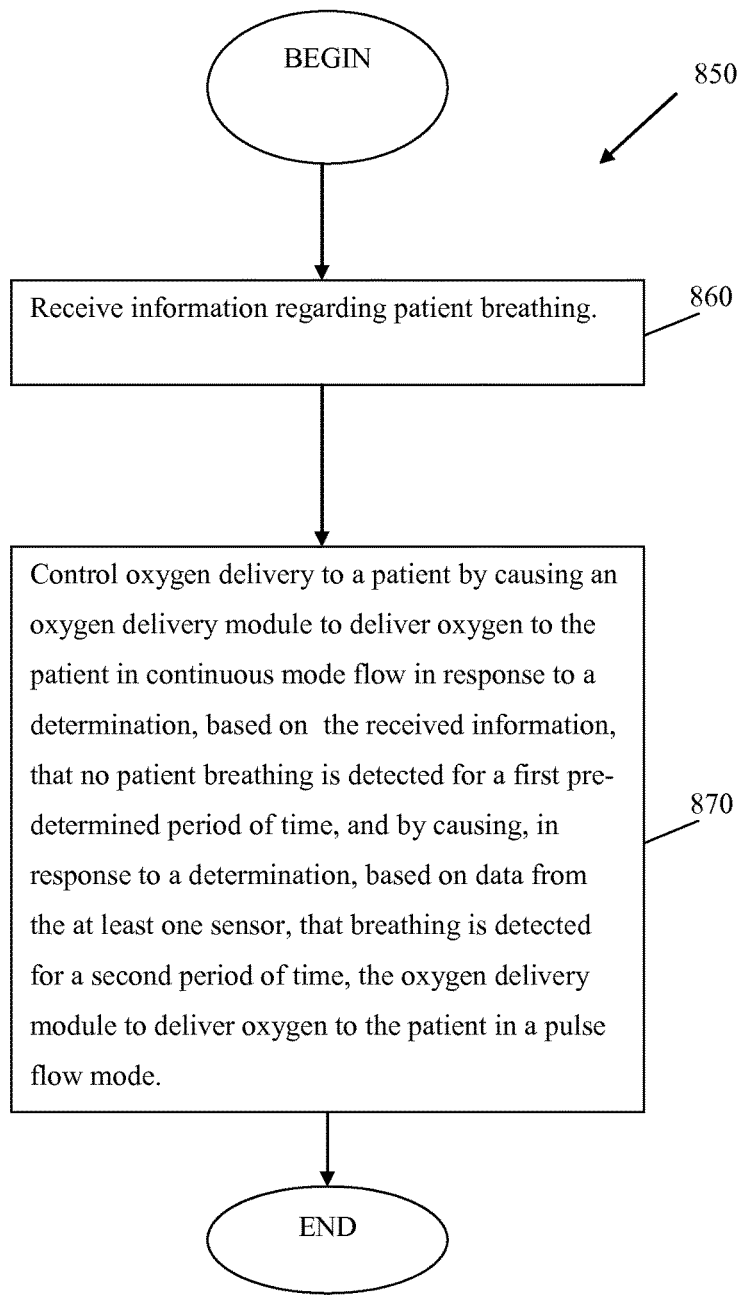
FIG. 12 is a flow chart of an example procedure to enable continuous breathing monitoring and control of oxygen delivery modes.

With reference now to FIG. 12, a flow chart of an example procedure 850 to enable continuous breathing monitoring and control of oxygen delivery modes is shown. Initially, oxygen may be delivered in pulse mode, and data regarding patient breathing is received 860. For example, a controller controlling operation of the oxygen delivery device may receive data from a pressure sensor connected to a cannula through which oxygen is delivered. Based on the received information, oxygen delivery to the patient is controlled 870 by causing an oxygen delivery module to deliver oxygen to the patient in continuous mode flow in response to a determination, based on the received information, that no patient breathing is detected for a first pre-determined period of time (e.g., 30 second, 60 seconds, or some other period of time). Additionally, in response to a determination, based on data from the at least one sensor, that breathing is detected for a second period of time, the controller causes termination of the continuous flow mode, and further causes the oxygen delivery module to deliver oxygen to the patient in a pulse flow mode. In some embodiments, pulse mode may also be restored after some pre-determined period of time has elapsed (e.g., 5 minutes, 10 minutes, etc.)

In addition, in some embodiments, when a patient is in continuous mode and starts to exercise, a continuous monitor of breathing pattern in continuous flow would allow the system to change the continuous setting to match the breathing pattern. For example, if a patient is prescribed 1 lpm continuous flow at a resting BPM of 15, the system can detect the 15 bpm and maintain 1 lpm. If the patient's BPM goes to 25 BPM, the system can automatically change the continuous setting to a higher flow value for 25 BPM.

Additional or different sensors may be used to sense a condition upon which control of the supply of oxygen gas to the user may be at least partially based. Further, any or all of the embodiments described above for regulating the amount of oxygen gas supplied to the user 108, i.e., variable-speed controller 119, supply valve 160, (or alternative embodiments) may be used with the one or more sensors and the control unit 110 to control of the supply of oxygen gas to the user 108.

In some implementations, a sensor may also be provided so as to detect one or more problems with respect to one of the filters of the device. For example, a sensor may be provided so as to determine a possible faulting intake filter. A dirty intake filter may choke the flow of air to the compressor and thus adversely affect the concentrator such as by causing an incomplete PSA cycle. An incomplete PSA cycle may in turn lead to water buildup on the adsorbent bed which may result in a degradation of system performance. Consequently, a sensor for detecting when a filter, such as an intake filter, has become dirty may alert a user of the need to change or clean the filter, for example, when a given differential pressure across the filter has been reached which signals that the filter may be dirty. Such a configuration could be useful in prolonging the life of the compressor and/or oxygen delivery module.

Figure 13:
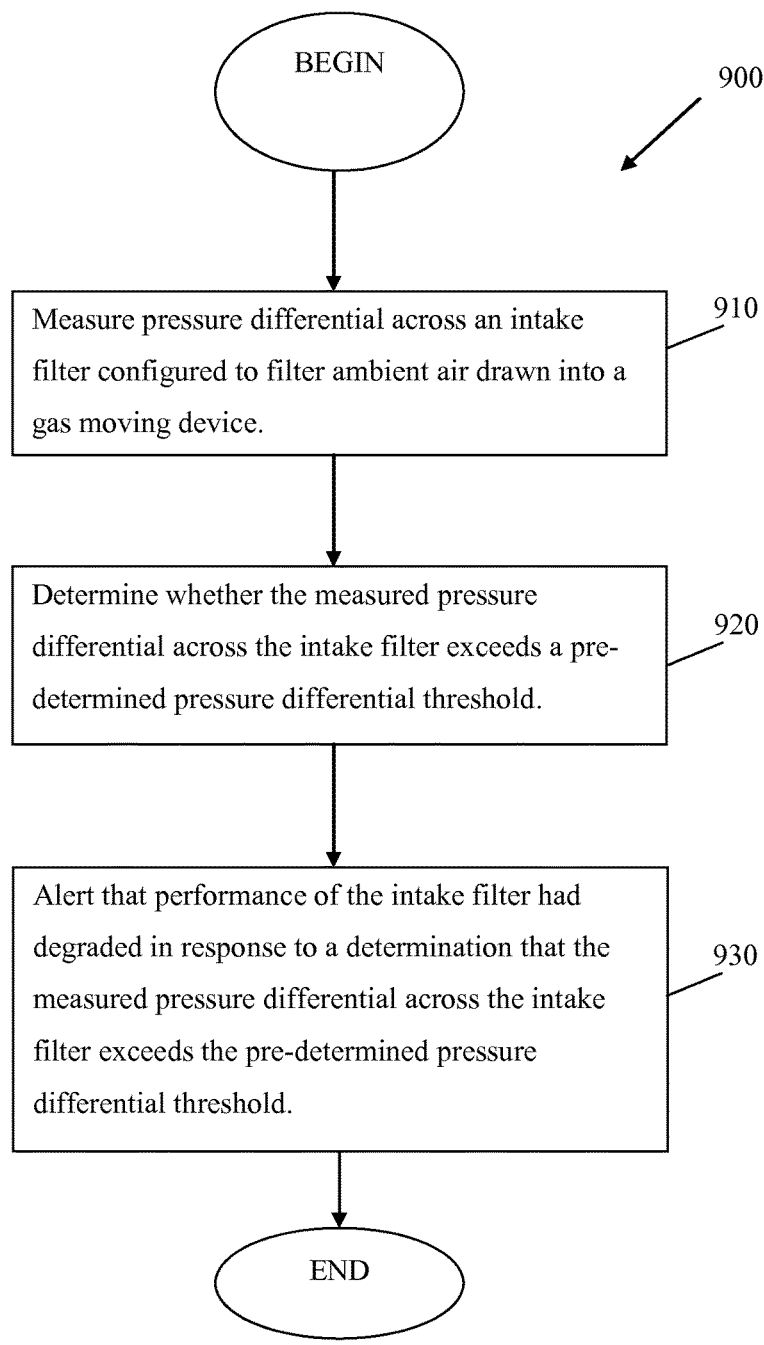
FIG. 13 is a flow chart of an example procedure to monitor and control filter performance.

Accordingly, in some embodiments, an oxygen delivery device may be provided that includes an oxygen delivery module (e.g., PSA, VPSA, etc.), at least one sensor to determine data representative of performance degradation of one or more filters used with the oxygen delivery device, and a controller (such as the controller 110 depicted in FIG. 1A and FIG. 10) to alert, based on the determined data representative of the performance degradation of the one or more filters, that performance of at least one of the one or more filters has degraded. As noted, in some embodiments, the one or more filters may include an intake filter to filter ambient air drawn into a gas moving device, where the at least one sensor is configured to determine pressure differential across the intake filter, and where the controller is configured to alert that the performance of the intake filter has degraded in response to a determination that the determined pressure differential across the intake filter exceeds a pre-determined pressure differential threshold. With reference to FIG. 13, a flow chart of an example procedure 900 to monitor and control filter performance is shown. The procedure 900 includes measuring 910 pressure differential across an intake filter configured to filter ambient air drawn into a gas moving device. A determination is then made 920 as to whether the measured pressure differential across the intake filter exceeds a pre-determined pressure differential threshold. In response to a determination that the measured pressure differential across the intake filter exceeds the pre-determined pressure differential threshold, an alert that performance of the intake filter had degraded is made 930.

In some implementations, a check valve and a gas filter may be mounted within the product tank. Such a tank may be designed to help keep non-metallic parts downstream of the PSA module (e.g., tanks, tubing, filter housings, etc) from passing atmospheric moisture to the PSA module via permeation. For instance, the check valve 1710 and filter housing 1720 (depicted in FIG. 29) may be positioned with respect to the product tank so as to provide a metallic shield that protects the downstream components of the device from atmospheric moisture which cannot penetrate the plastic structure typically enclosing such components. This may be useful because a configuration such as this prevents water, e.g., in the form of humidity, from passing through non-metallic materials on the product end of the PSA module and attached gas conduits thereby helping to prolong PSA module operating life.

Figure 29:
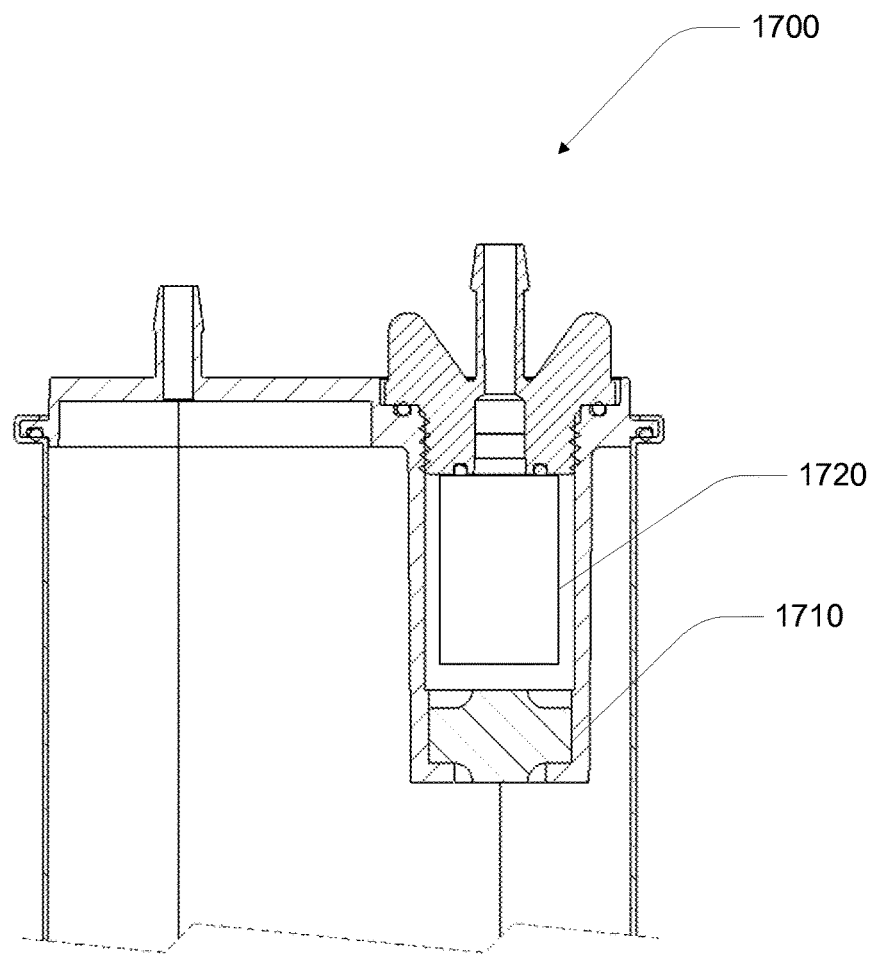
FIG. 29 is a cross-sectional diagram of an example embodiment of a check valve and integrated filter assembly.

Thus, with reference to FIG. 29, a cross-sectional diagram of an example embodiment of an assembly 1700 including the check valve 1710 and integrated filter assembly 1720 is shown. The assembly 1700 thus includes a check valve and gas filter included within a housing of an oxygen delivery device and positioned downstream of the oxygen delivery module. As noted, the check valve and gas filter are configured to prevent moisture present in components of the oxygen delivery device located downstream of the oxygen delivery module from entering the oxygen delivery module.

D. Control Unit

Figure 14:
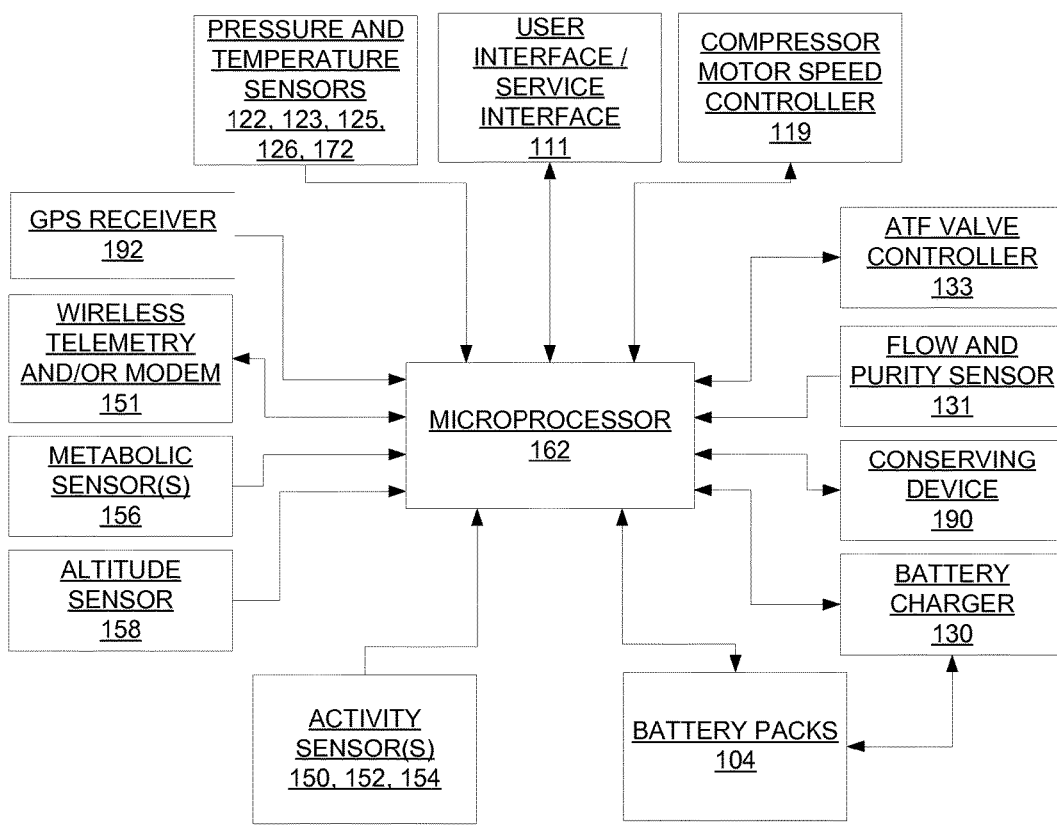
FIG. 14 is a block diagram of at least some components that may be controlled by a control unit of a portable oxygen delivery device.

With reference to FIG. 14, a block diagram of an arrangement of at least some of the components/units/modules of an example embodiment of an oxygen delivery device (oxygen concentration system) is shown. The control unit 110 (also depicted in FIGS. 1A and 1B) may be constituted in various configurations, and may include, for example, a central microprocessor or CPU 162 in communication with the components of the system described herein via one or more interfaces, controllers, ports or other electrical circuit elements for controlling and managing the system. The system 100 may include a user interface 111 that constitutes a part of the control unit 110, or the user interface may be coupled to the control unit 110 to enable the user, provider, doctor, etc., to enter information, e.g., prescription oxygen level, flow rate, activity level, etc., to facilitate controlling of the system 100.

While the CPU 162 is shown to be coupled to the various sensors depicted in FIG. 14, and to also be coupled to other units/components of an oxygen delivery device, in some embodiments, additional controllers, separate from the controller implemented using the CPU 162, may be used to separately and/or independently control any of the units/components depicted in FIG. 1. For example, separate controllers may be coupled to any number of the depicted sensors (to enable receipt and processing of data received from those sensors, and/or to control those sensors). Such controllers (or just the single controller implemented using the CPU 162) may also be coupled to additional components/units (such as additional sensors) not specifically depicted in FIG. 14, or in any of the other figures provided herein.

In some embodiments, it is useful to control the purity of oxygen in the flow from the device to the subject. For example, depending on a subject's complications, the delivery of oxygen at or above a given purity level may be required. However, in certain instances, it may be useful to deliver oxygen at the lower end of the acceptable range, for example, in those situations where the conservation of energy is of concern. Hence, by controlling oxygen purity to the lower end of the acceptable range of therapy, less power is consumed.

Accordingly, the controller may be configured to receive information pertaining to the acceptable purity range that may be delivered. One or more sensors, e.g., a flow/purity sensor, may be provided so as to determine the purity of the oxygen being delivered to the subject. This data may be sent to the controller. If the purity is above a given set point, for instance, above the lower range of what is acceptable for that subject, e.g., 90% purity, then the controller can adjust the operation of the system so as to down regulate the purity being delivered to the lower limit. For example, regulation of the purity of the generated oxygen can be performed by controlling the compressor's pressure, by controlling the ATF valve speed, etc. As less power is required for delivering oxygen at the lower purity limit, this mode conserves power, thereby allowing longer duration on battery. If the purity is below the acceptable level, the controller may then up regulate the system so as to ensure the oxygen being delivered is at least at the minimum required purity.

Thus, in some implementations, an oxygen delivery device is provided that includes an oxygen delivery module (e.g., PSA, VPSA, etc.) to produce at least concentrated oxygen at a controllable purity level from air, a gas moving device (e.g., a compressor) to deliver the ambient air to the oxygen delivery module, and at least one controllable motor to controllably drive the gas moving device. The oxygen delivery device further includes an energy source (a battery, such as a rechargeable battery, an external power source whose power is adapter by an adapter to the power requirements of the oxygen delivery device) to power the at least one controllable motor, a pressure sensor to determine a pressure level produced in the oxygen delivery device, a purity sensor to determine oxygen purity value produced by the oxygen delivery module. A controller of the oxygen delivery device is configured to control based on the determined oxygen purity value and the pressure level, at least the gas moving device's operations and the oxygen delivery module's operations so as to cause the pressure resulting from the operation of the gas moving device to be substantially at a pre-determined pressure value and to cause the purity level of the oxygen produced by the oxygen delivery module to be substantially at a pre-determined purity value. In some embodiments, the controller is configured to cause the pressure resulting from the operation of the gas moving device to be substantially at the pre-determined pressure value and to cause the purity level of the oxygen produced by the oxygen delivery module to be substantially at the pre-determined purity value in response to a determination that an energy source to power the oxygen delivery device is a battery (and thus it becomes more important to conserve the available power by controlling the oxygen delivery device to operate at the pre-determined oxygen purity level and/or the pre-determined pressure level).

The pre-determined pressure value may correspond to a minimum acceptable pressure level, e.g., between approximately 3-7 psig pressure, and the pre-determined purity value may correspond to a minimum acceptable oxygen purity level, e.g., between approximately 82-93% oxygen, such that energy consumption of the system is reduced.

Figure 15:
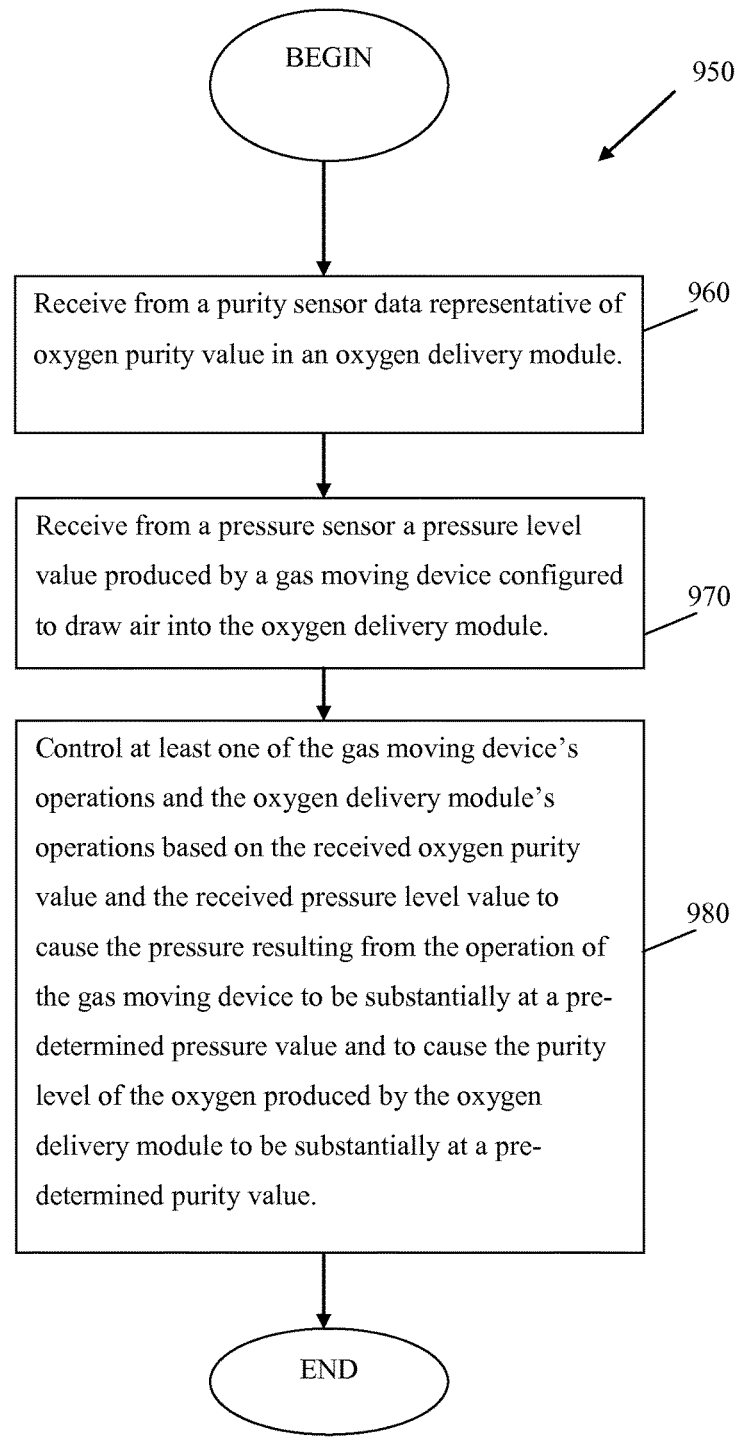
FIG. 15 is a flow chart of an example procedure to control operations of an oxygen delivery device based on measured oxygen purity and pressure values.

With reference to FIG. 15, a flow chart of an example embodiment of a procedure 950 to control operations of an oxygen delivery device based on measured oxygen purity and pressure values is shown. The procedure 950 includes receiving 960 data representative of oxygen purity value in an oxygen delivery module from a purity sensor, and receiving 970 from a pressure sensor a pressure level value produced by a gas moving device configured to draw air into the oxygen delivery module. Based on the received oxygen purity value and the received pressure level value, at least one of, for example, the gas moving device's operations and/or the oxygen delivery module's operations is controlled 980 to cause the pressure resulting from the operation of the gas moving device to be substantially at a pre-determined pressure value and to cause the purity level of the oxygen produced by the oxygen delivery module to be substantially at a pre-determined purity value. Additionally, by controlling oxygen purity to the lower end of the acceptable range of therapy, the pressure too can be down regulated to a minimum acceptable level for a selected flow to be delivered and product purge to be maintained. This may lead to an additional reduction of operating power, thus allowing longer duration on a battery-based energy source.

In addition to controlling the purity level of oxygen being delivered, the concentrator may additionally control the pulse volume being delivered. For instance, depending on the needs of the subject, a pulse of oxygen may be delivered in a volume that is anywhere from about 10 ml to 270 ml, such as about 90 ml to about 195 ml, including about 100 ml to about 192 ml. For example, the concentrator may be configured so as to produce a selected purity of oxygen to be delivered in a selected volume at a selected rate. In some embodiments, the concentrator is configured to deliver up to 3 liters per minute (LPM) continuously. Accordingly, when a selected volume, e.g., 3.0 LPM, is to be delivered in pulses, such as 192 ml per pulse, over a given time period, e.g., one minute, the amount to be delivered per pulse and the timing of the delivery may be controlled by the controller such that the amount per pulse is well within the range of the subject's normal breathing rate, thus ensuring that the maximum amount of oxygen is actually delivered to the subject in a manner and at a time that the subject can use it.

For example, if 192 ml pulses are to be delivered, the number of pulses needed that can be supported by an oxygen delivery device that delivers 3.0 liters per minute of oxygen is 3.0 LPM/0.192 mL=15.6 pulses/minute, or 15 BPM. 15 BPM is well within the normal breath rate for a typical resting subject. When the pulse volume of oxygen delivered during inspiration is larger, the fraction of inspired oxygen (FiO2) will be much higher. Therefore, simply by delivering in pulse mode, the concentrator is able to provide a fraction of inspired oxygen (FiO2) that may be 20% higher than that achieved with continuous flow using the same amount of power. Thus, larger pulse volumes help to increase FiO2 in those ambulatory subject's that need higher pulses. In some embodiments, to increase the FiO2, the pulse may be delivered during the first 60% of the patient's inspiratory period, which is the time period during which the body absorbs most of the oxygen available in the pulse.

Accordingly, in some implementations, an oxygen delivery device is provided that includes an oxygen delivery module (e.g., PSA, VPSA) configured to deliver a pulse including greater than 100 mL of concentrated oxygen, and a controller (which may be implemented as part of the control unit 110 shown in FIG. 1A) configured to control the oxygen delivery module to cause the oxygen delivery module to deliver the pulse including greater than the 100 mL of the concentrated oxygen within approximately first 60% of a patient's inspiratory period. To enable delivery of the pulse within the first 60%, it is generally required to achieve early detection of the onset of the patient's inspiratory cycle. As described herein, in some implementations, early detection of the onset of an inspiratory cycle is performed by receiving data from a sensor configured to detect patient's breathing, e.g., by detecting pressure changes within the patient's nasal passages by, for example, using a pressure sensor placed inside the cannula used to deliver oxygen. The received data representative of such detected pressure changes in the patient's nasal passages is processed, e.g., applying filtering functions that determine based on the raw data whether the inspiratory cycle has commenced.

Figure 16:
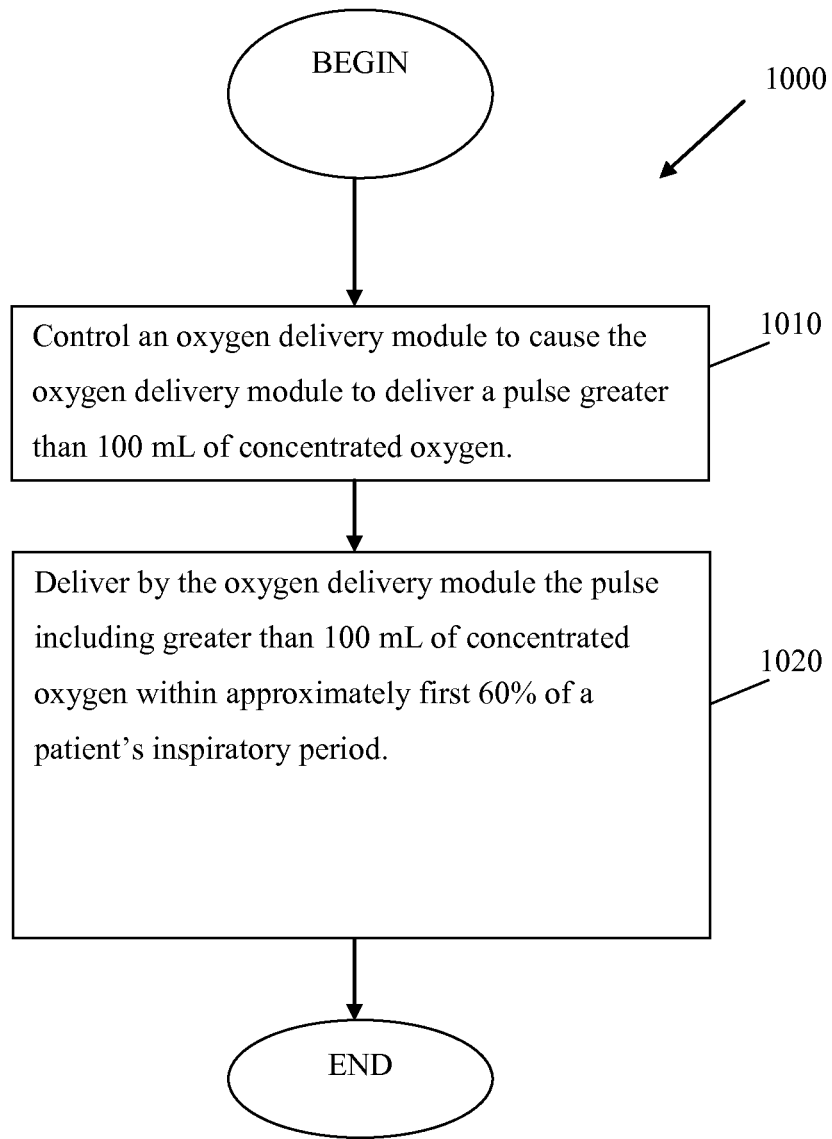
FIG. 16 is a flow chart of an example procedure to deliver oxygen pulses.

With reference to FIG. 16, a flow chart of an example procedure 1000 to deliver oxygen pulses is shown. The procedure includes controlling 1010 an oxygen delivery module (e.g., a PSA, VPSA, etc.) to cause the oxygen delivery module to deliver a pulse greater than 100 mL of concentrated oxygen. The oxygen delivery module delivers 1020 the pulse including greater than 100 mL of concentrated oxygen within approximately first 60% of a patient's inspiratory period of a patient's breathing.

To illustrate the efficacy of delivering large boluses of oxygen, consider the following three examples. In all three examples, the Inspiration:Expiration ratio (I:E) is assumed to be 1:3 (e.g., inspiration takes 1 second, while expiration lasts 3 seconds), the tidal volume is assumed to be 500 mL, the breath rate is assumed to be 15 BPM, and the oxygen delivery module, in these examples, produces oxygen with a purity of 92%.

In the first example, a three liter per minute continuous flow of oxygen is produced by a concentrator, equating to 50 mL/second delivered to the patient from the oxygen delivery device. Accordingly, the percent of oxygen in that flow is 92%×50 mL=46 mL $O_2$. The remainder of the tidal volume inhaled by the patient is 450 mL of air (500 mL-50 mL delivered by the oxygen delivery device), of which 94.5 mL (21%) is oxygen. Thus, with a continuous flow of 50 mL/second from the oxygen delivery device, the FiO2 in this example is computed to be (94.5 mL $O_2$+46 mL $O_2$)/500 mL=28.1%.

In the second example, a 96 mL pulse dose is to be delivered to the patient with each breath. The percent of oxygen in that pulse is 92%×96 mL=88.32 mL $O_2$. The remainder of the tidal volume inhaled by the patient is 404 mL of air (500 mL-96 mL delivered by the oxygen delivery device), of which 84.84 mL (21%) is oxygen. Thus, with a pulse of 96 mL from the oxygen delivery device, the FiO2 in this example is computed to be (88.32 mL $O_2$+84.84 mL $O_2$)/500 mL=34.6%.

In the third example, a 192 mL pulse dose is to be delivered to the patient with each breath. The percent of oxygen in that pulse is 92%×192 mL=176.64 mL $O_2$. The remainder of the tidal volume inhaled by the patient is 308 mL of air (500 mL-192 mL delivered by the oxygen delivery device), of which 64.68 mL (21%) is oxygen. Thus, with a pulse of 192 mL from the oxygen delivery device, the FiO2 in this example is computed to be (176.64 mL $O_2$+64.68 mL $O_2$)/500 mL=48.2%.

Accordingly, the ability to deliver larger oxygen pulse doses to the patient improves the FiO2 for the patient.

In some implementations, a boost mode may also be provided. Particularly, when a concentrator is operating at temperature or altitude extremes or from a limited (or limitless) power source, the flow from the compressor/vacuum pump and cycle time of the PSA/VPSA process can be adjusted to operate the concentrator to most efficiently meet a given selected therapeutic level. For example, a therapeutic level may be determined and prescribed by a clinician and that data entered into the controller, which will then control the components of the system so as to deliver the selected, e.g., prescribed, purity of oxygen to the subject. More specifically, a clinician may prescribe a continuous flow rate to a subject and/or a respiratory therapist may titrate the subject on a pulse dose machine such that the subject will have the same pulse oxygenation as they would when using a continuous flow mode. What is desired is that the subject breathe a gas at an elevated FiO2 so that the subject's pulse oxygenation is raised.

For example, without the boost mode, the actual purity of oxygen being delivered at a particular temperature and/or altitude might be 89%. The boost mode is configured for taking into account the effect that temperature and/or altitude may have on the system by adjusting the operations of the system so that the purity of the oxygen to be delivered would be higher, e.g., 92 to 94% in this particular example, thus, resulting in higher FiO2. Thus, the purity may be controlled and adjusted so as ensure that a given FiO2 is delivered.

Accordingly, in some embodiments, an oxygen delivery device may be provided that includes an oxygen delivery module (e.g., PSA, VPSA), at least one sensor to determine at least one environmental condition (e.g., ambient temperature and/or altitude) in which the portable oxygen delivery device is operating, and a controller to control, based on the determined at least one environmental condition, at least the oxygen delivery module's operations to cause a specified therapeutic requirement for the patient to be achieved.

In some embodiments, operations of the oxygen delivery device may be controlled based on a patient's tidal volume and the patient's fraction of inspired oxygen. For example, when operating in FiO2 mode, the concentrator may monitor BPM and purity. A physician and/or clinician may input to the system a target FiO2, and an approximate I:E ratio. Given these data inputs, the controller determines the optimum oxygen delivery device operating conditions (e.g., compressor speed, valve speed, oxygen purity) to deliver that will result in reduced (and in some cases, the lowest) power being consumed, and therefore in longer (and in some cases, the longest) battery time for the desired FiO2. Thus, by determining tidal volume, e.g., having the subject blow with no forced effort into a variable volume container with a fixed backpressure and determining the amount of gas collected, and providing that tidal volume data into the controller of the concentrator, the controller can then adjust the system so as to deliver oxygen based upon a targeted FiO2 for the subject. The benefits of this mode of operation is to extend the operating temperature and/or altitude ranges, maximize the amount of time a subject spends at optimal saturation, help prevent patient exacerbations, minimize the amount of power consumed by the concentrator, and maximize time on battery. This may also be accomplished when using independent compressor and vacuum pumps.

Accordingly, in some implementations, an oxygen delivery device may be provided that includes an oxygen delivery module (e.g., PSA, VPSA) to produce at least concentrated oxygen, and a controller configured to control the oxygen delivery module to cause the oxygen delivery module to deliver oxygen to a patient based on a patient's tidal volume data representative of the normal volume of air displaced between inspiration and expiration by the patient, and further based on a fraction of inspired oxygen (FiO2) value required for the patient. The controller may thus determine operating conditions (e.g., speed of the gas moving device providing an air flow to the oxygen delivery module, oxygen delivery module cycle speed, and desired oxygen purity level to be produced by the oxygen delivery device) based on the patient's tidal volume and FiO2 values. In some embodiments, the determination of operating conditions may also be based also on one or more of, for example, respiratory rate for the patient, oxygen purity value of the oxygen delivered to the patient, and/or Inspiration:Expiration (I:E) ratio. In some embodiments, the oxygen delivery device may also include a pressure sensor to determine a pressure level produced by oxygen delivery device, a gas moving device providing an air flow to the oxygen delivery module, and a purity sensor to determine oxygen purity value produced by the oxygen delivery device.

Figure 17:
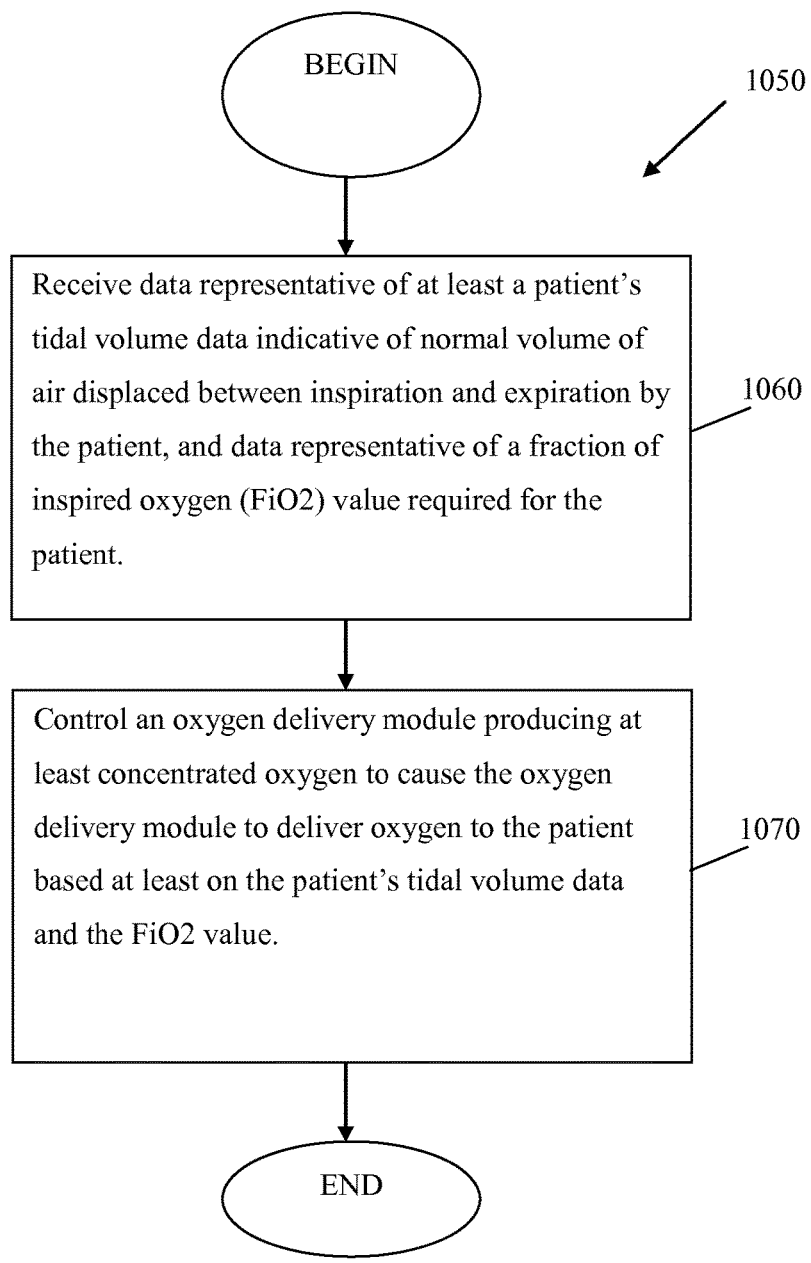
FIG. 17 is a flow chart of an example procedure to control operations of an oxygen delivery device.

With reference to FIG. 17, a flow chart of an example embodiment of a procedure 1050 to control operation of an oxygen delivery device is shown. The procedure 1050 includes, in some embodiments, receiving 1060 data representative of at least a patient's tidal volume data indicative of normal volume of air displaced between inspiration and expiration by the patient, and data representative of a fraction of inspired oxygen (FiO2) value required for the patient. Based at least on the patient's tidal volume data and the FiO2 value, an oxygen delivery module (such a PSA or VPSA) producing at least concentrated oxygen is controlled 1070 to cause the oxygen delivery module to deliver oxygen to the patient. Control of the operations of the oxygen delivery device can be performed, for example, by controlling the speed of the compressor delivering air to the oxygen delivery module.

Figure 18:
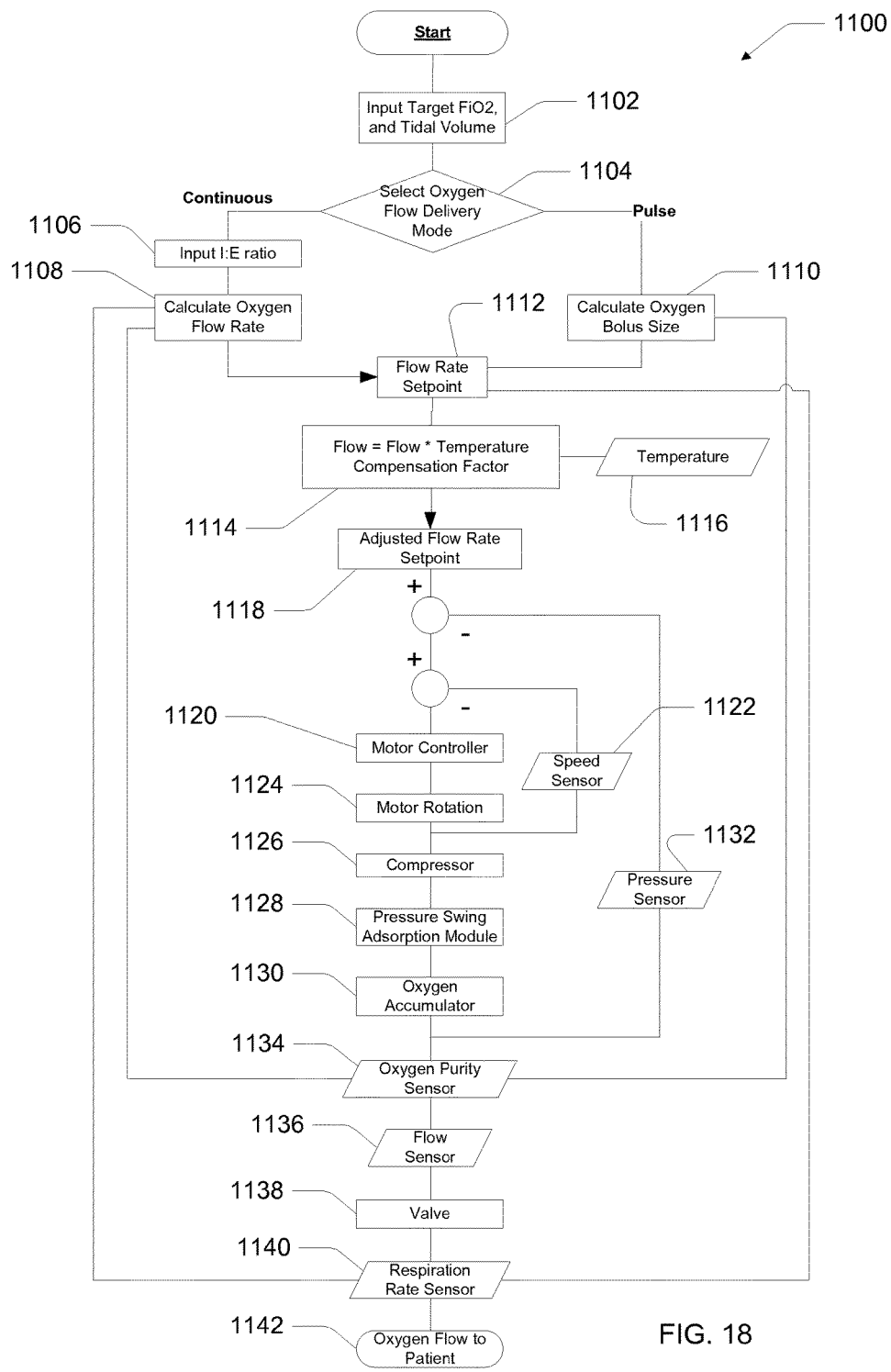
FIG. 18 is a flow chart of another example procedure to control operation of an oxygen delivery device based, at least in part, on a patient's tidal volume, FiO2 value, as well as on other factors.

FIG. 18 is a flow chart of another example procedure 1100 to control operation of an oxygen delivery device based, at least in part, on a patient's tidal volume, FiO2 value, as well as other factors, and provides additional details on implementations to determine operation conditions for an oxygen delivery device. As noted herein, when providing supplemental oxygen to a patient whose respiratory condition requires it, the fraction of oxygen in the inspired gas is elevated from the normal 20.9% oxygen found in normal atmospheric composition. The supplemental oxygen may be delivered via a nasal cannula or similar conduit and combines with the oxygen present in inhaled air. Elevating this fraction of inspired oxygen (FiO2) is a process to bring about desired physiologic responses in a patient. In some conventional systems, oxygen delivery was performed such that each liter of continuous flow supplemental oxygen from an oxygen concentrator delivered to a patient via nasal cannula was approximately equivalent to increasing the patient's FiO2 by 3%. In another conventional system, delivery of a bolus of oxygen was timed with the patient's inspiration.

The bolus of oxygen supplements the air that the patient is breathing and serves to elevate the patient's FiO2 by some amount. The amount of supplemental oxygen a patient required to maintain a specific FiO2 varies with several factors. Among these are respiratory rate, exercise level, tidal volume, inspiratory time, expiratory time, and purity of oxygen provided by the device. A drawback of conventional systems is that they do not account for varying respiratory rates or delivered purity, nor do they provide direct control of oxygen delivered to a patient by varying inputs for patient tidal volume, inspiratory time, or expiratory time. As a result, patients using oxygen delivery devices that utilize these methods often provide insufficient amounts of oxygen to the patient.

A patient using supplemental oxygen obtains oxygen from two sources: the supplemental source and ambient air. The total flow of gas provided to the patient, $Q_T$, is the sum of the delivered flow of gas from the supplemental source, $Q_{O2}$, and the flow of air, $Q_{Air}$, as described by Equation (1). The air flow $Q_{Air}$ is the flow of air that is inspired by a patient during a breath.

$$Q_T = Q_{O2} + Q_{Air} \tag{1}$$

Considering just the portion of these flows that are composed of oxygen, Equation (2) follows where $f_{IO2}$ is the fraction of oxygen inspired by the patient, $F_{DO2}$, is the fraction of gas delivered by the supplemental device that is composed of oxygen, and the value of 0.209 represents the fraction of oxygen found in normal atmospheric composition.

$$F_{IO2} Q_T = F_{DO2} Q_{O2} + 0.209 Q_{Air} \tag{2}$$

Recognizing that when supplemental oxygen is delivered to a patient, the patient only makes use of the oxygen delivered during the inspiratory phase of a breath (and thus, as described above, in some embodiments, an oxygen delivery device may be configured to deliver a substantial portion of the oxygen pulse in the 60% of the inspiration portion of the breathing cycle). Accordingly, the total flow of gas inspired by a patient $Q_T$ is the product of the patient's tidal volume, $V_T$, and respiratory rate, f.

$$Q_T = f V_T \tag{3}$$

The fraction of gas that is inhaled during each breath can be expressed as $\beta$, where I is the time of inspiration and E is the time of expiration.

$$\beta = \frac{I}{I + E} \tag{4}$$

Equations (1) through (4) may be combined algebraically to derive Equation (5). Equation (5) may be used to perform the "Calculate oxygen flow rate" operation (at 1108) in the example procedure 1100 shown in FIG. 18.

$$Q_{O2} = \frac{f V_T (F_{IO2} - .209)}{\beta (F_{DO2} - .209)} \tag{5}$$

When implemented to control an oxygen concentrator (oxygen delivery device) operating in a continuous flow mode, as determined at 1104 (where a determination is made whether continuous or pulse mode is to be used), the device monitors oxygen purity (at 1134) and patient respiration rate (at 1140) to compute and adjust the oxygen flow rate to be delivered to the patient (at 1108). That is, the monitored values of the oxygen purity and patient respiration rate are provided (e.g., as part of a feedback loop) to enable determination/adjustment of the oxygen flow rate.

When operating in a pulse flow mode, as determined at 1104, an oxygen delivery device provides a bolus of oxygen each time a patient breath is detected (it should be noted that in some embodiments selection of flow mode or pulse mode may be performed manually based on input by a user, or it may be performed automatically based on detected conditions, such as a condition where no breathing is detected for a period of time, as was described in relation to FIG. 12). This bolus of oxygen combines with the additional oxygen contained in the inspired breath of air to elevate the patient's FiO2. Since a pulse mode oxygen delivery device is dealing with a discrete volume of gas as opposed to a flow, the total volume of gas inhaled by a patient during each breath is the tidal volume, $V_T$. Tidal volume is the sum of the bolus volume of gas from the supplemental source, $V_{O2}$, and the volume of air, $V_{Air}$, as described by Equation (6).

$$V_T = V_{O2} + V_{Air} \quad (6)$$

Again, considering just the portion of these flows that are composed of oxygen, Equation (7) follows where $F_{IO2}$ is the fraction of oxygen inspired by the patient, $F_{DO2}$, is the fraction of gas delivered by the supplemental device that is composed of oxygen, and 0.209 represents the fraction of oxygen found in normal atmospheric composition.

$$F_{IO2} V_T = F_{DO2} V_{O2} + 0.209 V_{Air} \quad (7)$$

Equations (6) and (7) may be combined algebraically to derive equation (8). Equation (8) may be used to perform the "Calculate oxygen bolus size" operation at 1110 in the example procedure 1100 shown in FIG. 18.

$$V_{O2} = \frac{V_T(F_{IO2} - .209)}{(F_{DO2} - .209)} \quad (8)$$

The amount of oxygen that the oxygen delivery device has to produce, $Q_{O2}$, when operating in pulse mode is the product of the volume of the boluses delivered $V_{O2}$ and the patient's detected respiratory rate f (e.g., detected at 1140).

The advantage of controlling the operation of an oxygen delivery device to a specified fraction of inspired oxygen level is that it serves to better maintain the patient's blood oxygen saturation at appropriate therapeutic levels while at the same time managing the amount of oxygen delivered to the patient. This is important when the oxygen delivery device is portable and battery operated. For such systems, the duration and weight of the system is a function that is affected by the respective battery capacity when the oxygen delivery device is a concentrator or tank capacity when the oxygen delivery device utilizes a liquid oxygen storage vessel or high pressure gas cylinder for the oxygen source. Smaller batteries or cylinders/tanks allow for lighter and more convenient portable systems, but larger batteries and cylinders/tanks allow for longer operating durations. By controlling to a prescribed FiO2, a patient receives more oxygen when his/her respiratory rate increases, such as during periods of exertion. As a result, the patient's blood oxygen saturation remains at therapeutically appropriate levels and the patient feels better and is less likely to experience an exacerbation of their respiratory condition. Conversely, when the patient's respiratory rate decreases, such as during periods of rest or sleep, oxygen product rates from the device are reduced and the device can operate longer.

In addition, the methods and apparatus for controlling an oxygen delivery device to a specified FiO2 may be combined with other procedures/methods for controlling an oxygen delivery device to further optimize device operation and dimensions. Such other methods/procedures include, but are not limited to: a) oxygen purity feedback, determined at 1134 by, for example, an oxygen purity sensor, b) system pressure feedback, determined at 1132 by, for example, a pressure sensor, and c) temperature compensation based on measured temperature determined at 1116 by, for example, a thermistor, which is then used to adjust, at 1114, the computed flow rate or bolus size. Other factors and procedures that effect delivery of oxygen to a patient may be combined into a procedure such as the procedure 1100 of FIG. 18. Computed flow rates or bolus sizes may then be provided to a controller, or various controllers, configured to control operation of the oxygen delivery device and thus the flow of oxygen (at 1142) to the patient. For example, the computed flow rate may be provided to a motor controller (at 1120) which in turn causes controlled actuation of the motor (at 1124) that drives the oxygen delivery device's compressor (at 1126). The computed flow rate is also used to control the valve speed in the operation of the oxygen delivery module (at 1128)]

Figure 30:
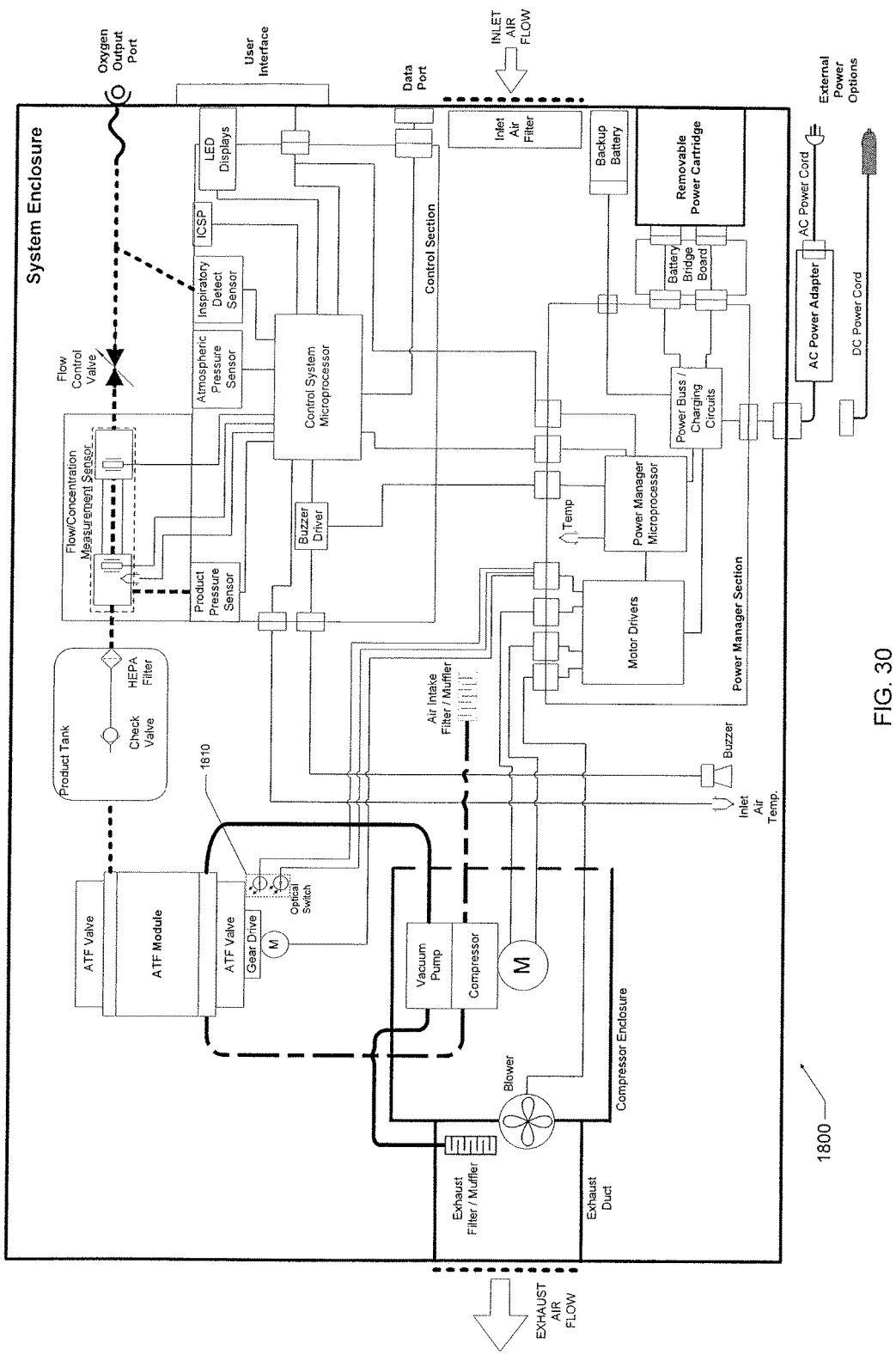
FIG. 30 is a schematic diagram illustrative of performance of an oxygen delivery device.

The main elements of embodiments of the oxygen device 100 have been described above. FIG. 30 is a schematic flow diagram to further illustrate the configuration and operations of an oxygen delivery device.

The following sections describe a number of additional features, one or more of which may be incorporated into the embodiments of the oxygen delivery device described herein.

II. Conserving Device

Figure 19:
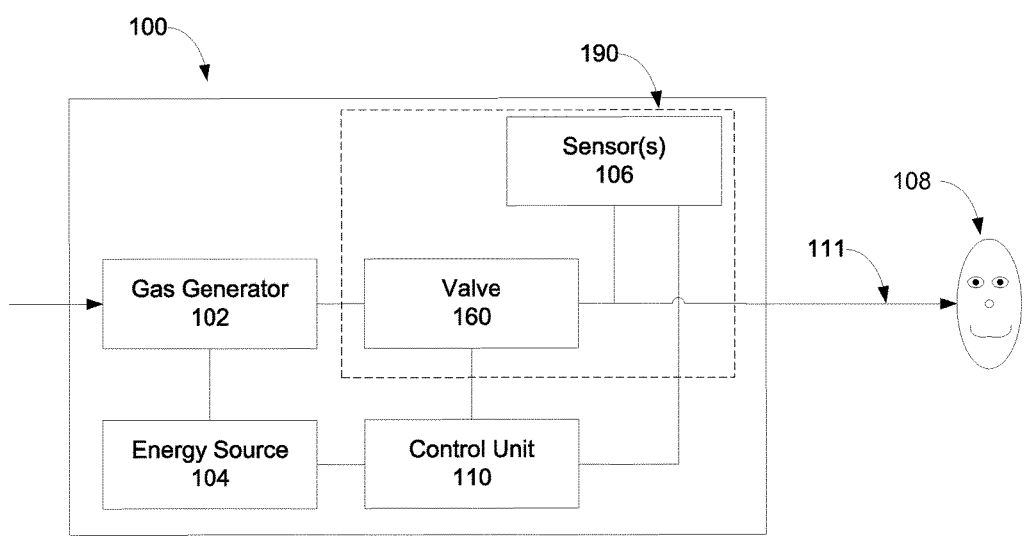
FIG. 19 is a schematic diagram of a conserving (or demand) device that may be incorporated into an oxygen delivery device to more efficiently utilize the oxygen produced by an oxygen gas generator.

With reference to FIG. 19, a conserving device or demand device 190 may be incorporated into the system 100 to more efficiently utilize the oxygen produced by the oxygen gas generator 102. During normal respiration, a user 108 inhales for about one-third of the time of the inhale/exhale cycle and exhales the other two-thirds of the time. Any oxygen flow provided to the user 108 during exhalation is of no use to the user 108 and, consequently, the additional battery power used to effectively provide this extra oxygen flow is wasted. A conserving device 190 may include a sensor that senses the inhale/exhale cycle by sensing pressure changes in the cannula 111 or another part of the system 100, and supply oxygen only during the inhale portion or a fraction of the inhale portion of the breathing cycle. For example, because the last bit of air inhaled is of no particular use because it is trapped between the nose and the top of the lungs, the conserving device 190 may be configured to stop oxygen flow prior to the end of inhalation, improving the efficiency of the system 100. Improved efficiency translates into a reduction in the size, weight, cost and power requirements of the system 100.

The conserving device 190 may be a stand-alone device in the output line of the system 100, similar to a regulator for scuba diving, or may be coupled to the control unit 110 for controlling the oxygen generator 102 to supply oxygen only during inhalation by the user 108.

The conserving device 190 may include one or more sensors, such as the sensors described above. For example, the conserving device may include a sensor for monitoring the respiration rate of the user.

In some embodiments, the conserving device may include a supply valve such as the supply valve 160 described above. In some embodiments, a valve implementation for supply valve 160 shown in FIG. 1B may be a piezoelectric ("piezo") valve. For instance, although in some embodiments, one or more of the valves may be a proportional solenoid valve for controlling the flow of gas to be provided to a subject, such as when operating in a conservation or pulse mode, in some embodiments, one or more valves may be based upon using a piezo element which may be employed for opening the valve. For example, a piezo valve may be substituted for a solenoid valve so as to control the flow of the gas. The piezo valve connects electrically to a driver that in turn connects to the control microprocessor and power bus. The use of a piezo valve may be useful because it may respond faster to the controller than a more traditional solenoid valve. This in turn may result in a higher FiO2, and may better allow for the tailoring of the gas flow waveform so as to better treat the subject. The use of a piezo valve may also lead to lower power consumption and further cost savings because they are relatively inexpensive to produce.

Accordingly, in some embodiments, an oxygen delivery device may be provided that includes an oxygen delivery module (e.g., PSA, VPSA) to provide at least concentrated oxygen, a piezoelectric valve coupled to an output of the oxygen delivery module to receive the produced concentrated oxygen, a driver to electrically actuate the piezoelectric valve, and a controller to control the driver to cause controllable actuation of the piezoelectric valve by the driver so as to cause controllable opening of the valve to enable flow of oxygen delivered by the oxygen delivery module to be directed for inhalation by a patient via the piezoelectric valve. In some implementations, the oxygen delivery device may also include one or more sensors to determine data representative of one or more of environmental conditions (e.g., temperature, altitude), operating conditions of the oxygen delivery device (pressure, motor speed), and the patient's therapeutic conditions (e.g., level of activity). The controller may thus be to control the driver to cause controllable actuation of the piezoelectric valve based, at least in part, on the determined data from the one or more sensors representative of the one or more of environmental conditions, operating conditions of the oxygen delivery device, and patient's therapeutic conditions.

Figure 20:
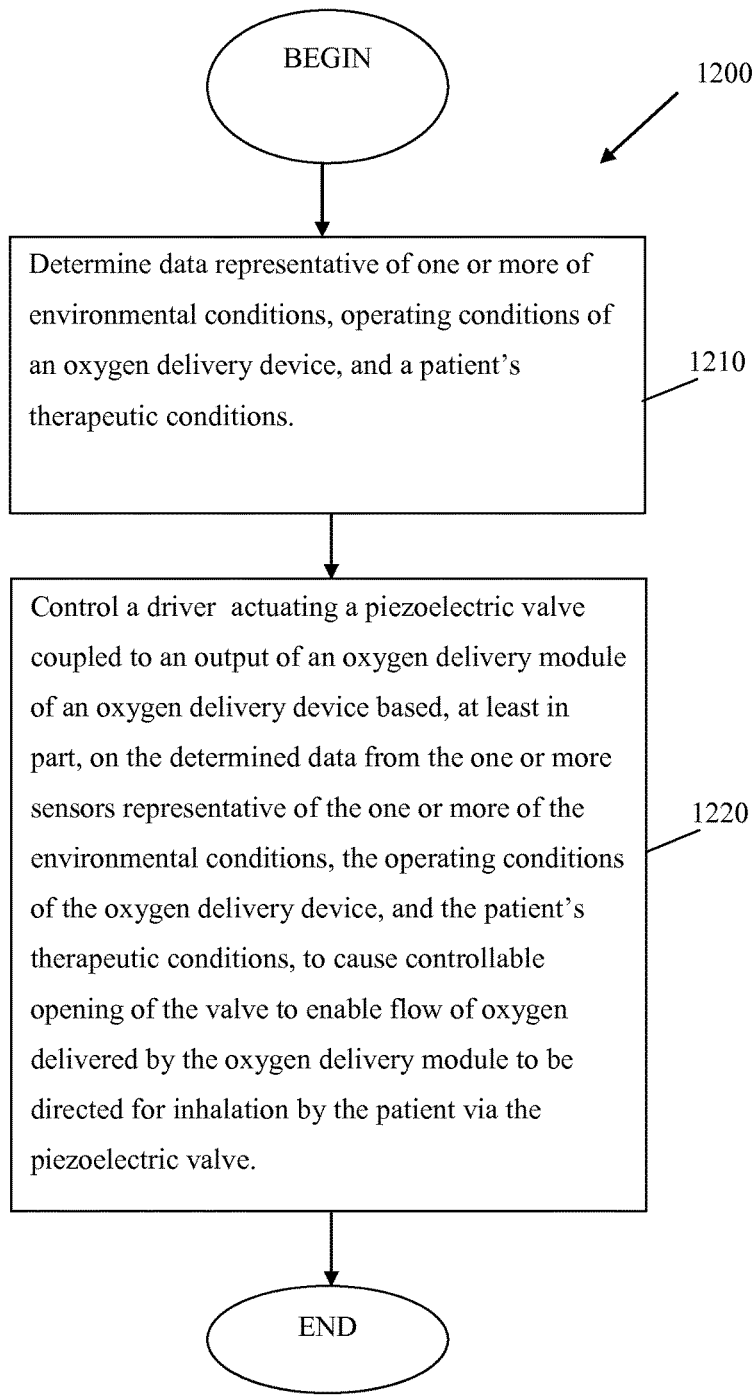
FIG. 20 is a flow chart of an example procedure to control oxygen delivery.

With reference to FIG. 20, a flow chart of an example procedure 1200 to control oxygen delivery is shown. The procedure 1200 includes determining 1210 data representative of one or more of environmental conditions, operating conditions of an oxygen delivery device, and a patient's therapeutic conditions. Based, at least in part, on the determined data from the one or more sensors representative of the one or more of the environmental conditions, the operating conditions of the oxygen delivery device, and the patient's therapeutic conditions, a driver actuating a piezoelectric valve coupled to an output of an oxygen delivery module of an oxygen delivery device is controlled 1220 to cause controllable opening of the valve to enable flow of oxygen delivered by the oxygen delivery module to be directed for inhalation by the patient via the piezoelectric valve.

The system 100 (as depicted in FIG. 19) may also include a special cannula retraction device for retracting the cannula 111 when not in use. Further, the cannula 111 may come in different lengths and sizes.

III. Tracking Device

With reference back to FIGS. 1B and 14, in some embodiments, the system 100 may include a global positioning system (GPS) receiver 192 for determining the location of the system 100. The location of the receiver 192 and, hence, the user 108 can be transmitted to a remote computer via the communication module (telemetry mechanism or modem). This may enable locating the user 108 in the event the user has a health problem, e.g., heart attack, when the user hits a panic button on the system, when an alarm is activated on the system, or for some other reason.

Thus, because a concentrator may not returned to the equipment provider when a patient goes off therapy, a mechanism (e.g., implemented on a processor-based device using software) may be included so as to track the physical position of the concentrator. A locator, therefore, may be provided in association with the concentrator. For instance, a GPS device may be included in combination with a cellular network so as to locate the device. Alternatively, a WiFi enabled geolocator may be provided. In one embodiment, a WiFi transmitter is provided such that if the device is near a WiFi hotspot, the hotspot will pick it up and then transmit a signal, e.g., via the internet, to the equipment provider to this inform the provider of the equipments location.

Further still, a small PC board could be built and mounted inside the concentrator that would sound a buzzer at a given time period, e.g., every 60 seconds, if the device has not been turned on in a defined period of time, e.g., six weeks. This will notify a person of the presence of the device and its need for return, thus preventing loss or delayed return of concentrator to the provider.

Thus, in some embodiments, an oxygen delivery device may be provided that includes an oxygen delivery module (e.g., PSA, VPSA) to produce at least concentrated oxygen, and a tracking device coupled to the oxygen delivery device to enable determining geographical location of the oxygen delivery device. The tracking device including one or more of, for example:
  a) A WiFi-based geolocation device including a wireless receive configured to determine availability of WiFi-based network routers in the vicinity of the oxygen delivery device, and to communicate with one or more of the WiFi-based network routers available in the vicinity of the oxygen delivery device. An approximation of the geographical location of the oxygen delivery device is thus determined based on location data associated with the one or more WiFi-based network routers (whose geographical locations are generally known) communicating with the oxygen delivery device.
  b) A GPS-based tracking device to receive GPS signals from one or more satellite, determine approximate position of the GPS-tracking device based on the received GPS signals, and communicate to a remote location data representative of the determined the approximate position of the GPS-tracking device.
  c) A device to monitor use of the oxygen delivery device, and to cause an alarm to be activated in response to a determination that the oxygen delivery device was not used for at least a pre-determined period of time.

In some embodiments, additional functionality (e.g., through a programmable processor implementation) may be provided to allow for remote setup of the device. For example, when a concentrator includes pulse mode operation, remote set up is useful to help ensure that the subject is receiving adequate oxygen saturation. For example, using the system control and monitoring operations of the oxygen delivery device, and data from clinical sensors, the oxygen delivery device may be programmed and otherwise set up remotely. Specifically, a pulse oximeter may be provided and data derived from the pulse oximeter is transmitted back to the provider. The provider can then use that data to titrate the patient and set up the device remotely. This will help serve subjects in remote areas or other areas where it is hard to access in person healthcare services. This can also reduce the cost of patient setup at the same time as increasing efficiency.

Accordingly, in some embodiments, an oxygen delivery device may be provided that includes an oxygen delivery module to produce at least concentrated oxygen, and at least one sensor to determine data representative of one or more of environmental conditions, operating conditions of the oxygen delivery device, and patient's therapeutic conditions. The oxygen delivery device also includes a controller configured to communicate the determined data to a remote station to facilitate determining values of operation parameters controlling operation of the oxygen delivery device based on, at least in part, the communicated data representative of the one or more of the environmental conditions, the operating conditions of the oxygen delivery device, and the patient's therapeutic conditions. The controller is further configured to receive from the remote station data representative of the values of the operation parameters controlling operation of the oxygen delivery device, and adjust the operation parameters of the oxygen delivery device based on the data received from the remote station.

Figure 22:
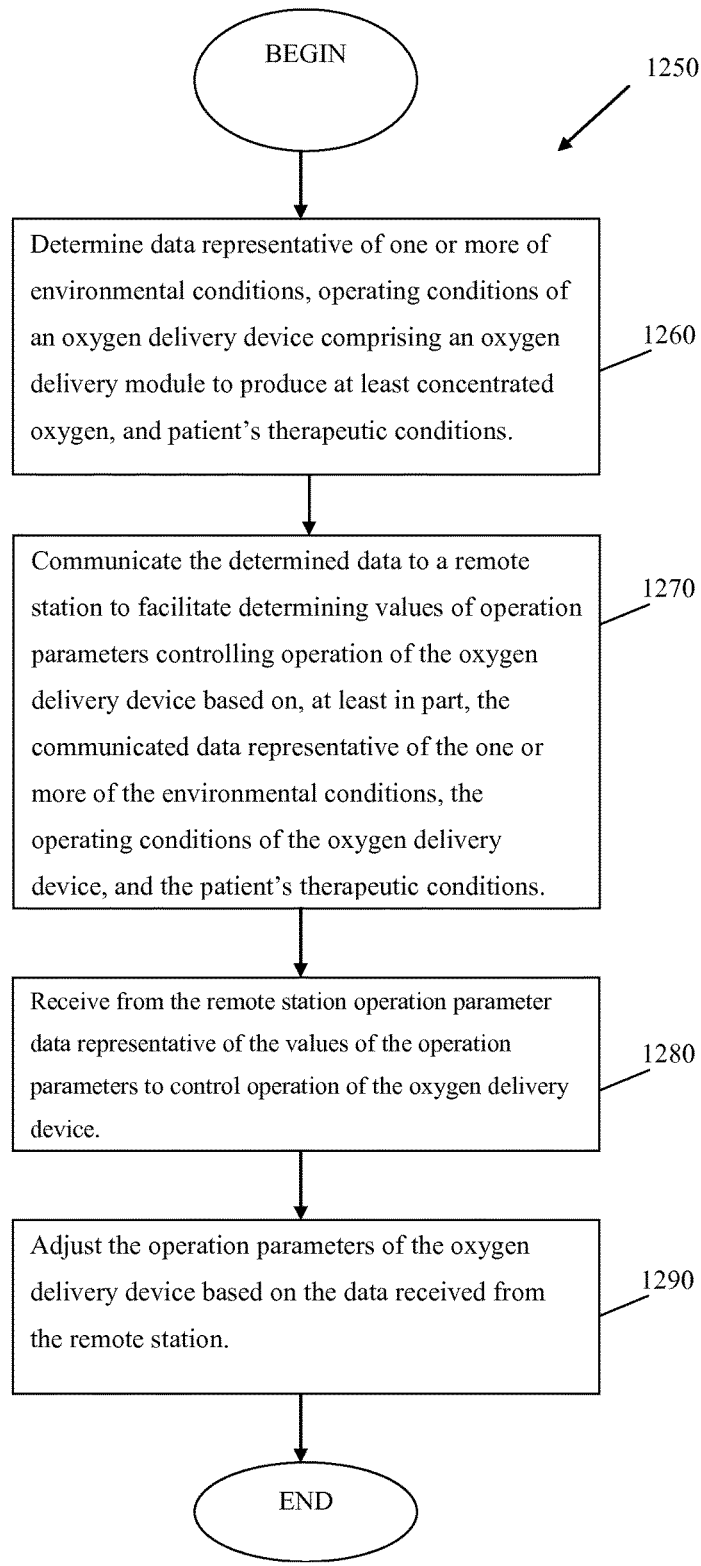
FIG. 22 is a flow chart of an example procedure to implement remote set up.

With reference to FIG. 22, a flow chart of an example procedure 1250 to implement remote set up is shown. The procedure 1250 includes determining 1260 data representative of one or more of environmental conditions, operating conditions of an oxygen delivery device comprising an oxygen delivery module to produce at least concentrated oxygen, and patient's therapeutic conditions. The determined data representative of the one or more of the environmental conditions, the operating conditions of the oxygen delivery device, and the patient's therapeutic condition, is communicated 1270 to a remote station to facilitate determining values of operation parameters controlling operation of the oxygen delivery device. Subsequently, operation parameter data representative of the values of the operation parameters to control operation of the oxygen delivery device is received 1280 from the remote station. The operation parameters of the oxygen delivery device are adjusted 1290 based on the data received from the remote station.

IV. Additional Operational Features and Accessories

In some embodiments, an oxygen delivery device, such as a portable oxygen delivery device described herein, may additionally be used with nebulizers for the delivery of aerosolized medications. For instance, a nebulizer may be included so as to receive and convert a medication in to a mist that may then be added into the oxygen flow so as to deliver the mist into the lungs with the inhalation of the oxygen being delivered. Such embodiments can be employed with the appropriate medication so as to treat any disease capable of being treated with nebulized medicaments, such as cystic fibrosis, asthma, and other respiratory diseases. Any suitable nebulizer may be employed so long as it is capable of being integrated into the concentrator system, such as a jet nebulizer and/or atomizer. For example, the nebulizer, e.g., a jet nebulizer, may be connected via tubing to the concentrator, wherein the oxygen delivered to the nebulizer blasts at high velocity through the liquid medicine converting it into an aerosol, which is then delivered and inhaled by the subject. Hence, the continuous flow gas stream coming from the concentrator may be configured to function as the gas source for a nebulizer.

Figure 21:
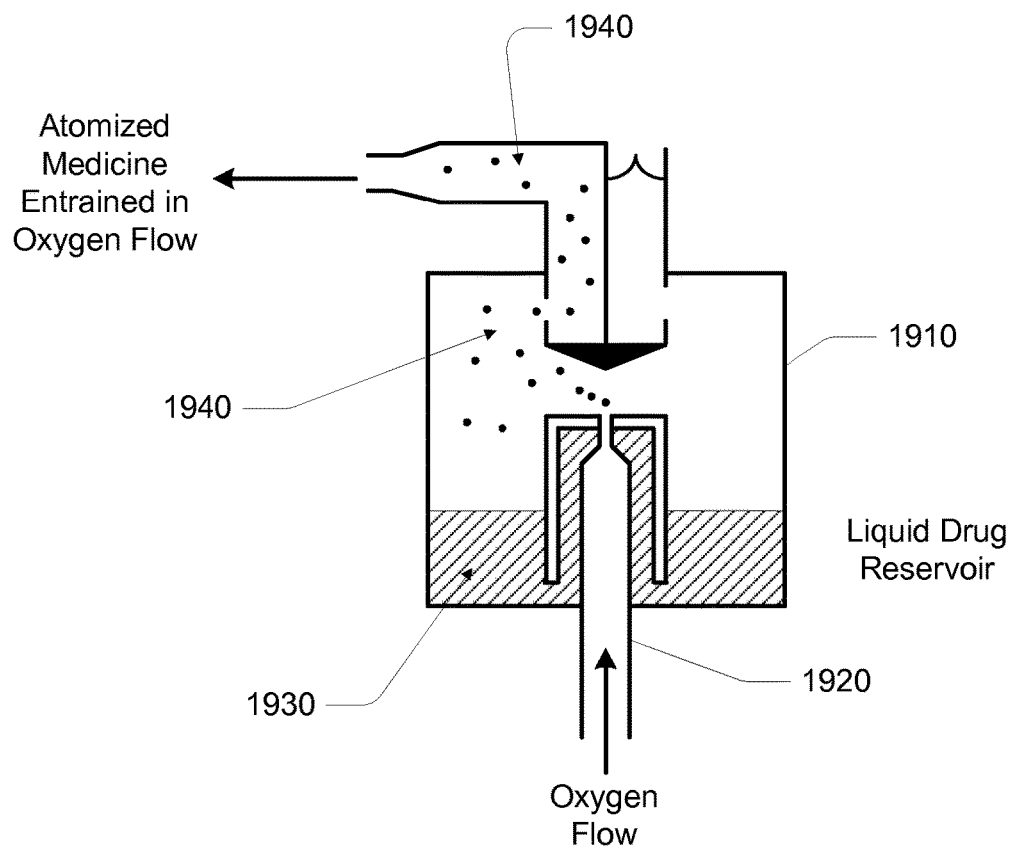

Thus, and with reference to FIG. 21, in some embodiments, a respiratory device 1900 is provided that includes an oxygen delivery device including an oxygen delivery module to produce at least concentrated oxygen, and a gas moving device to deliver air to the oxygen delivery module (not shown in FIG. 21), with the gas moving device being driven by a motor (not shown in FIG. 21) to actuate the gas moving device. The respiratory device also includes a nebulizer containing liquid medication 1930 for a patient that is stored in a medication chamber (or reservoir) 1910 defined within the nebulizer, the nebulizer being coupled to the oxygen delivery device such that the concentrated oxygen produced by the oxygen delivery module is directed (e.g., via a tube 1920) into the inner medication chamber 1910 of the nebulizer to convert at least some of the liquid medication 1930 into aerosol medication 1940. At least some of the concentrated oxygen directed into the nebulizer and the at least some of the converted aerosol medication are delivered for inhalation by a patient through a nebulizer outlet port.

With reference to FIG. 23, a flow chart of an example embodiment of a procedure 1300 to deliver aerosolized medications is shown. The procedure 1300 includes producing 1310 concentrated oxygen using an oxygen delivery device including an oxygen delivery module (e.g., PSA, VPSA) to produce at least the concentrated oxygen, and a gas moving device (e.g., a compressor) to deliver air to the oxygen delivery module. At least some of liquid medication (e.g., to treat cystic fibrosis, asthma, and/or other respiratory diseases) contained in a medication chamber of a nebulizer is converted 1320 into aerosol medication by directing the concentrated oxygen produced by the oxygen delivery module into the nebulizer. As noted, in some embodiments, the nebulizer may include a jet nebulizer configured to use the concentrated oxygen directed into the nebulizer at high velocity as a gas source to cause the liquid medication to be converted to aerosol. At least some of the concentrated oxygen directed into the nebulizer and at least some of the converted aerosol medication for inhalation by a patient is delivered 1330 through a nebulizer outlet port.

In some embodiments, in a similar manner, when the concentrator is operating in a continuous flow mode, the gas from the concentrator may be fed into a closed container holding a scented fluid. When fed through a conduit and/or diffuser into the bottom of the container, the gas will bubble up through the fluid, entraining an amount of fluid vapor with it. An outlet at the top of the container will allow the egress of the gas with the entrained vapor into a connection leading to the subject. In a manner such as this, patient compliance with oxygen therapy may be encouraged and/or respiratory disinfection, decongestion, expectoration or beneficial psychological effects may be achieved. It is to be noted that water may be substituted herein for the scented fluid, thus serving as a humidifier and functioning to add a water vapor into the oxygen being delivered to the subject.

Accordingly, in some implementations, an oxygen delivery device is provided that includes an oxygen delivery device including an oxygen delivery module (e.g., PSA, VPSA) to produce at least concentrated oxygen, and a gas moving device (e.g., a compressor) to deliver air to the oxygen delivery module. The gas moving device is driven by a motor to actuate the gas moving device. The oxygen delivery device also includes a container holding fluid, the container being coupled to the oxygen delivery device such that the concentrated oxygen produced by the oxygen delivery module is directed into the container to be passed through the fluid so as to entrain at least some fluid vapor. At least some of the concentrated oxygen directed into the container and the fluid vapor are delivered for inhalation by a patient through an outlet of the container.

Figure 24:
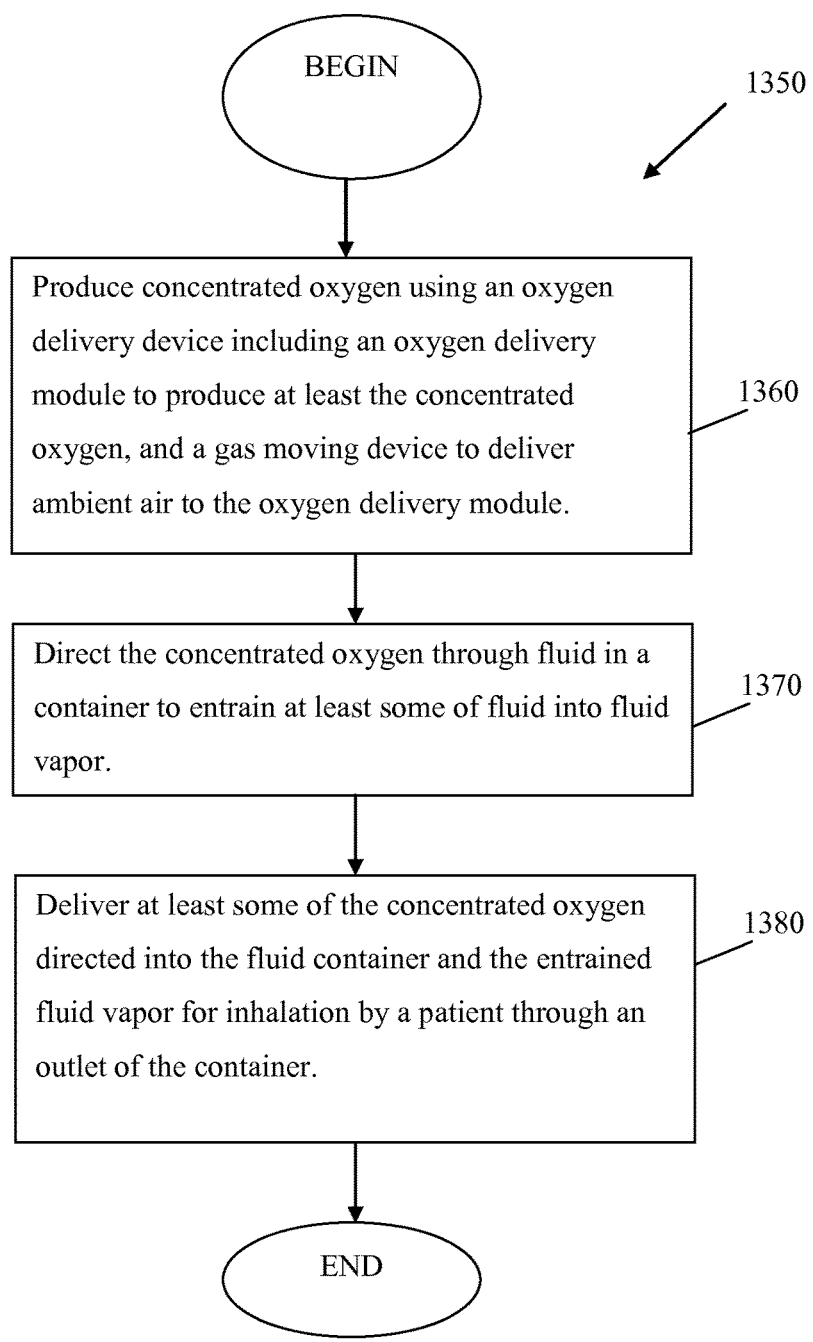
FIG. 24 is a flow chart of an example procedure to deliver fluid vapor.

With reference to FIG. 24, a flow chart of an example embodiment procedure 1350 to deliver fluid vapor is shown. The procedure 1350 includes producing 1360 concentrated oxygen using an oxygen delivery device including an oxygen delivery module to produce at least the concentrated oxygen, and a gas moving device to deliver ambient air to the oxygen delivery module. The concentrated oxygen is directed 1370 through fluid in a container to entrain at least some of fluid into fluid vapor. In some embodiments, the fluid may include water and/or scented fluid. At least some of the concentrated oxygen directed into the fluid container and the entrained fluid vapor for inhalation by a patient is delivered 1380 through an outlet of the container.

As noted above, patient compliance with a prescribed therapeutic delivery of oxygen is important. Accordingly, the systems and devices described herein may be configured for monitoring one or more of hours of usage, times of usage, flow rates, respiration rates, and the like so as to track and/or send, e.g., to a healthcare professional, a subject's compliance. The concentrator may also be configured so as to monitor other parameters as well, such as a biometric patient identifier, sleep state, exercise rate, heart rate, level of ambulation, SpO2, and the like. Such data may then be analyzed and/or compiled to form a more complete picture of the subject's compliance, and therapy effectiveness.

Thus, in some implementations, an oxygen delivery device is provided that includes an oxygen delivery module (e.g., PSA, VPSA), one or more sensors to determine data representative of one or more of environmental conditions, operating conditions of the oxygen delivery device, and patient's characteristics, and a controller to control, based at least in part on the determined data, at least the oxygen delivery module's operations. The oxygen delivery device also includes an identification module to receive information representative of an identity of a user and to compare the received information to stored data uniquely identifying a patient associated with the portable oxygen delivery device, and a display module to present information based, at least in part, on data determined by the one or more sensors. The controller may thus associate patient identification with data collected by the one or more sensors. The information displayed may include trends of the available information. Data collected/determined by the one or more sensors may be used to compute one or more of, for example, sleep state, respiratory rate, inspiratory:expiratory time ratio, ambulation time, activity level, oxygen saturation, total oxygen delivered, heart rate, oxygen delivered per period of time, hours of usage, and/or usage time. The display device may be configured to present information based, at least in part, on the data determined by the one or more sensors in response to a determination by the identification module that the data determined by the one or more sensor corresponds to the patient identified by the identification module.

In some embodiments, the one or more sensors may include, for example an electroencephalogram, an electrooculogram, an electrocardiogram, an actigraph, a pedometer, a pulse oximeter, an accelerometer, a pressure sensor, a flow sensor, a purity sensor, a clock, and/or a timer. In some embodiments, the identification module may include one or more of, for example, an alpha-numeric keypad, an iris scanner, a magnetic stripe card, a barcode scanner, a fingerprint scanner, a facial feature recognition device, and a palm scanner.

In some embodiments, the controller may further be configured to compare the determined data representative of the one or more of the environmental conditions, the operating conditions of the oxygen delivery device, and the patient's characteristics, to respective pre-determined threshold values representative of one or more of normal environmental conditions, normal operating conditions of the oxygen delivery device, and normal patient's characteristics, and communicate an alert in response to a determination that at least one of the determined data representative of the one or more of the environmental conditions, the operating conditions of the oxygen delivery device, and the patient's characteristics, deviates from a respective at least one of the pre-determined threshold values representative of one or more of normal environmental conditions, normal operating conditions of the oxygen delivery device, and normal patient's characteristics.

For instance, in some embodiments, the concentrator may be configured to detect and/or monitor a subject's respiratory rate, such as while the patient is ambulatory or sleeping. For example BPM data, e.g., while the concentrator is delivering at a constant flow, may be extracted and the data communicated to the controller. In one instance, a pressure sensor may be fluidly attached to the lumen of a cannula, which sensor can detect pressure and thus be used to determine actual BPM and thereby monitor the subject's respiratory rate.

In some embodiments, identity of the patient may be determined using a biometric patient identifier may be determined, for instance, by employing the same features used to sense and index unique physiological information, such as iris scan, palm scan, finger print, facial feature recognition, and the like. A sleep state may also be determined. For example, a sensor, such as a sensor conventionally used in polysomography (electroencephalogram (EEG), electrooculogram (EOG), electrocardiogram (ECG)), and the like may be used, or alternately an actigraph or ZEO® sleep system technology may be employed in combination with a oxygen delivery device of the disclosure so as to determine a subject's sleep state. A level of ambulation may also be determined so as to measure how active a subject is during a given period of time. This can be done with an actigraph, pedometer, and the like for use in combination with an oxygen delivery device of the disclosure. Any of this information may then be communicated to the controller of the concentrator, e.g., via wire or wirelessly, and employed to ensure that at least a minimum selected amount of oxygen and a minimum selected purity level is maintained given the measured changing needs of the subject. Such information can additionally serve to increase subject compliance which should in turn decrease COPD recidivism, decrease insurance fraud, and better provide usage data which would in turn be used to design better products.

Further, in some embodiments, the oxygen delivery device may include a display for displaying one or more sensed data and the like. For instance, a display may be used to indicate data pertinent to a characteristic of the device and/or a characteristic of a subject, such as a subject's need for oxygen. For instance, the display may display a rate of flow, a purity level of oxygen in the flow, ambient temperature or altitude, moisture level, battery life remaining, usage data, and the like. Further, the display may indicate a measured parameter such a subject's oxygenation level, blood pressure, peripheral oxygen saturation (SpO2) level, breaths per minute (BPM), as well as a graphical representation showing a given trend for one or more of the above, and the like.

Such a display would be useful because while a subject may subjectively believe that there are no problematic issues as regards the use of the concentrator to provide supplemental oxygen, their breathing rate BPM may increase during exertion or their peripheral oxygen saturation (SpO2) could decrease below a particular level deemed safe, e.g., below 90%, for various reasons, including exertion, insufficient delivery of oxygen, malfunctioning of one or more components of the concentrator, improper cannula use, and the like. The visual display may be useful so as to ensure the user that all is functioning well and/or to warn the user when all is not functioning well, and/or to provide the user with trending data will allow a user or caregiver to correlate actions with these biological indicators of health status. The display, therefore, can serve to indicate and/or alert the subject and/or a caregiver to the subject's health status.

Accordingly, in some embodiments, an oxygen delivery device is provided that includes an oxygen delivery module (e.g., a PSA, VPSA, a liquid oxygen storage system, a high pressure gaseous oxygen storage system, a compressing mechanism to compress oxygen-rich gas to a higher pressure), and one or more sensors to determine data representative of one or more of environmental conditions, operating conditions of the oxygen delivery device, and patient's characteristics. As noted, such sensors may include one or more of, for example, an electroencephalogram, an electrooculogram, an electrocardiogram, an actigraph, a pedometer, a pulse oximeter, an accelerometer, a pressure sensor, a flow sensor, a purity sensor, a clock, and/or a timer. The oxygen delivery device further includes a controller to control, based at least in part on the determined data, at least the oxygen delivery module's operations, and also includes a display module (e.g., a module using a CRT screen, a LCD screen, a plasma screen, etc.) to present information based, at least in part, on the data representative of the characteristics of the patient. Such a display module may also be configured as a user input interface, e.g., a touch screen. The display module may also include discrete buttons adjacent, or otherwise proximate to, the display area to enable providing user input. The information presented on the display module may include one or more of, for example, patient's sleep state, patient's respiratory rate, inspiratory:expiratory time ratio, ambulation time, activity level, oxygen saturation, total oxygen delivered, heart rate, oxygen delivered per period of time, hours of usage, and/or usage time, and may further include information pertaining to trends of the available information. The oxygen delivery device may also include a communication module to communicate data to a remote location using one or more of, for example, a wireless communication link, and a wired-based communication link.

In some embodiments, an accessory to measure and display the state-of-charge and state-of-life for the battery 104 of an oxygen delivery device would be utilized. Such a device may be a separate accessory (either hand-held or table-top) to enable an user to readily determine the state-of-charge of the battery pack (for proper storage and/or shipping) and also the present state-of-life of the pack (i.e. number of remaining full charge/discharge cycles before the pack reaches 80% of its original 'when new' capacity). A table-top version of this device could also have an added feature to enable providers to easily charge packs in their storage inventory to an optimum charge condition (e.g. a 40% charged state) to ensure maximum life of the packs. Such functionality to measure and display the state-of-charge and state-of-life for a battery could also be incorporated into the user interface of an oxygen delivery device.

In some embodiments, the controller, such as the controller 110 depicted, for example, in FIG. 1A, may be configured with a factory default mode, which functions to return the device to its factory default settings. This can simplify service, refurbishment between patients, and minimize troubleshooting time. Accordingly, in some implementations, an oxygen delivery device is provided that includes a controller to control at least some operations of the oxygen delivery device, including controlling operations affecting the oxygen delivery module, that includes at least one processor based device, and at least one non-transitory memory storage device to store computer instructions. The computer instructions include instructions that when executed on the at least one processor-based device cause the at least one processor-based device to receive data indicative that default operational settings of the oxygen delivery device are to be activated, and, in response to the received data, activate the default operational settings of the oxygen delivery device.

Additionally, the controller's configuration (e.g., implemented by programming a controller that includes a programmable processor-based device) may be configured with a limp home mode. In such a mode, rather than merely showing a malfunction of other error state where oxygen production is stopped, the device is programmed to operate so long as it can make some amount of oxygen greater than a given minimal purity, e.g., greater than 21% purity, and deliver it to a subject. In this manner, a subject who would otherwise not get oxygen because the device has shut down is still able to get some beneficial amount of oxygen.

Thus, in some implementations, an oxygen delivery device is provided that includes an oxygen delivery module to produce at least concentrated oxygen, a purity sensor to determine oxygen purity value produced by the oxygen delivery module, and one or more device sensors to monitor the operation of the oxygen delivery device. The oxygen delivery device also includes a controller configured to receive data from the purity sensor and the one or more device sensors, to determine, based on the data received from the one or more device sensors, whether an operational problem condition exists in relation to the operation of the oxygen delivery device, and, in response to a determination that a problem condition exists in relation to the operation of the oxygen delivery device, to cause at least partial operation of the oxygen delivery device to be maintained upon a further determination, based on the data received from the purity sensor, that the oxygen purity level exceeds a pre-determined minimum purity threshold.

Figure 25:
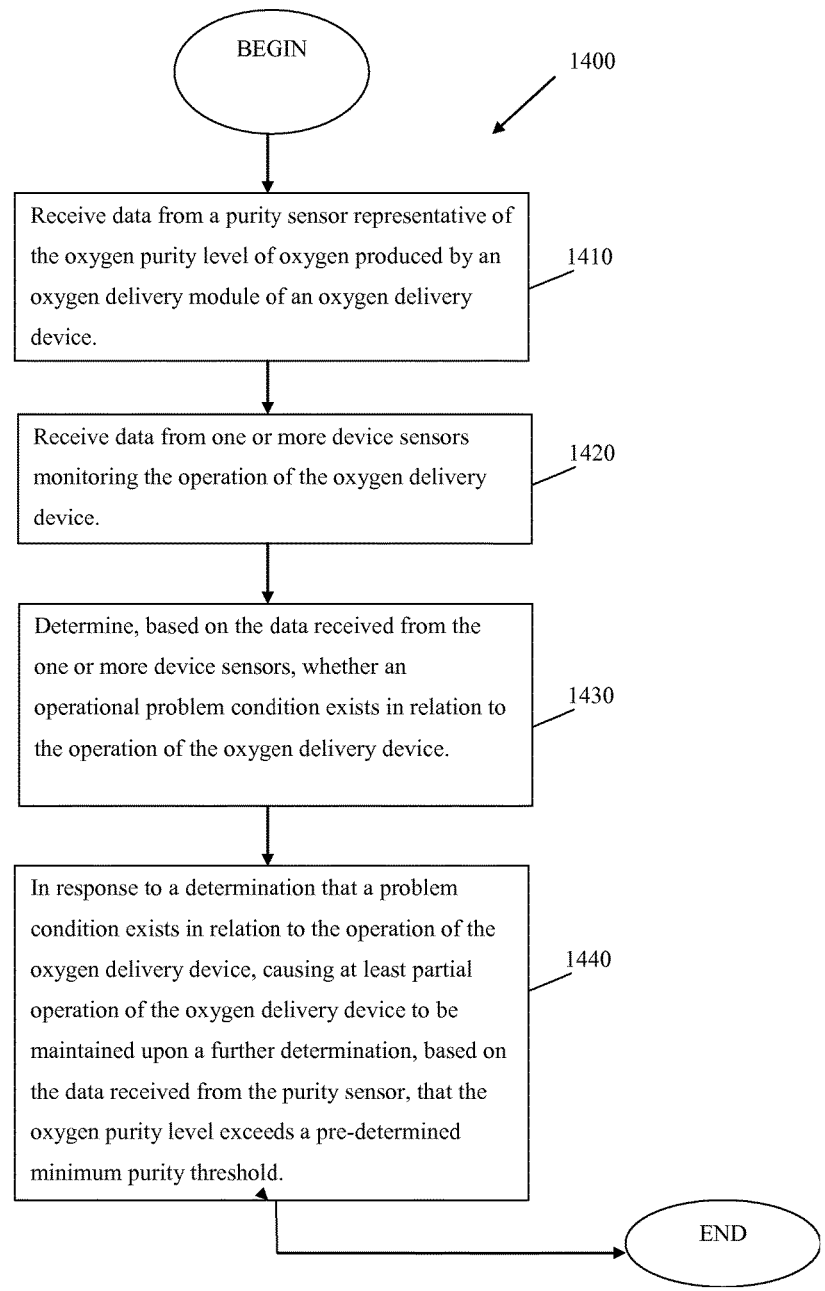
FIG. 25 is a flow chart of an example procedure to operate an oxygen delivery device.

With reference to FIG. 25, a flow chart of an example embodiment of a procedure 1400 to operate an oxygen delivery device is shown. The procedure includes receiving 1410 data from a purity sensor representative of the oxygen purity level of oxygen produced by an oxygen delivery module of an oxygen delivery device, and receiving 1420 data from one or more device sensors monitoring the operation of the oxygen delivery device. Based on the data received from the one or more device sensors, a determination is made 1430 of whether an operational problem condition exists in relation to the operation of the oxygen delivery device. In response to a determination that a problem condition exists in relation to the operation of the oxygen delivery device, at least partial operation of the oxygen delivery device is caused to be maintained 1440 upon a further determination, based on the data received from the purity sensor, that the oxygen purity level exceeds a pre-determined minimum purity threshold. In some embodiments. the pre-determined minimum purity threshold is 21%. In some embodiments, the controller is configured to cause a change from an operation mode that was active before the determination that a problem condition exists to another operational mode for the oxygen delivery device.

A lockout mode may also be provided, thus enabling or disabling one or more given modes of operation. Accordingly, in some implementations, an oxygen delivery device may be provided that includes an oxygen delivery module to produce at least concentrated oxygen, a controller to control at least some operations of the oxygen delivery device, including controlling operation affecting operations of the oxygen delivery module, the controller configured to enable the activation of one or more of a plurality of operational modes supported by the oxygen delivery device. The controller includes at least one processor based device, and at least one non-transitory memory storage device to store computer instructions. The computer instructions include instructions to cause the at least one processor-based device to receive data indicative of one or more operational modes from the plurality of operational modes that are to be activated, and in response to the received data, enable the one or more operational modes of the oxygen delivery device that are to be activated. Modes of operation that may be disabled include those that may not be therapeutically appropriate for a patient (i.e. pulse mode) or modes including advanced operating features. The instructions may also include instructions to cause the at least one processor-based device to receive data indicative of at least one active operational mode that is to be disabled. In some embodiments, the controller may be configured to cause the oxygen delivery device to operate in a default generic mode when all other of the plurality of operational modes are not active.

In some embodiments, a method for preventing the use of counterfeit or non-manufacturer approved battery packs may be provided. Battery packs represent a significant portion of the cost of oxygen delivery systems and as such create the potential for users to want to utilize lower cost battery packs. Such alternate battery packs may lack the correct safety features and hardware compatibility, which in turn could create a safety hazard and loss of revenue for the manufacturer. While mechanical or electrical methods may be readily reverse engineered, a software method with cryptographic function is more secure. Thus, within the battery pack 104 a battery management chip that utilizes a cryptographic function, such as SHA-1 (Secure Hash Algorithm) or some similar encryption procedure, may be used to identify an approved battery and not allow operation of the oxygen delivery system with batteries that are not approved by the original equipment manufacturer.

In some embodiments, a maintenance reminder light may also be provided so as to indicate when regular, periodic (or sensed) maintenance is not performed. The indicator may be displayed to the user to alert them that maintenance needs to be performed. Thus, an oxygen delivery device may therefore include a user interface including an indicator to indicate that maintenance of the oxygen delivery device is required in response to a determination of deviations from a maintenance schedule required for the oxygen delivery device.

In some implementations, a controller, such as the controller 110 of FIG. 1A, may be configured (e.g., by programming a programmable processor-based controller) for automated debugging, calibration, and or diagnostics. Such configuration may reduce the service cost and time required for servicing an oxygen concentrator. Accordingly, in some embodiments, an oxygen delivery device is provided that includes an oxygen delivery module (e.g., PSA, VPSA, etc.) to produce at least concentrated oxygen, and a controller to perform one or more of, for example, controlling at least some operations of the oxygen delivery device, identifying problems associated with the oxygen delivery device, resolving the identified problems associated with the oxygen delivery device, and/or calibrating the oxygen delivery device. The controller includes at least one processor based device, and at least one non-transitory memory storage device to store computer instructions. The computer instructions include instructions that when executed on the at least one processor-based device cause the at least one processor-based device to receive data representative of operation of the oxygen delivery device, and determine automatically problems associated with the operations of the oxygen delivery device based on the received data.

In some embodiments, the computer instructions include instructions that cause the processor-based device to determine automatically problems associated with the operations of the oxygen delivery device using an expert system learning engine. In some embodiments, the computer instructions include instructions that cause the processor-based device to automatically determine data to controllably change one or more operation parameters of the oxygen delivery device to cause a change in the operation of the respiratory care device, and to change the operation parameters of the oxygen delivery device according to the determined data. Further details regarding remote and/or automated debugging, calibration and diagnostic are provided, for example, in patent application Ser. No. 12/892,793, entitled "Controlling and Communicating with Respiratory Care Devices," the content of which is hereby incorporated by reference in its entirety.

In some embodiments, to speed factory or field calibration of the oxygen concentrator, a tee fitting can be included upstream of the purity sensor. In this manner oxygen of a known purity can be directed through this tee when the concentrator is not producing oxygen and the sensor may be calibrated accordingly. For instance, by placing a tee fitting upstream of a purity sensor, a calibration gas of known composition can be fed into the concentration sensor thereby allowing the sensor to be calibrated faster and with greater accuracy. When the sensor is not being calibrated, the port may be capped. Thus, in some embodiments, an oxygen delivery device may further include a purity sensor to determine oxygen purity value, a coupler (e.g., a tee-coupler) coupled to the purity sensor, the coupler including an inlet port to receive gas from an external source. The oxygen delivery device includes a controller configured to receive data from the purity sensor measuring the purity of oxygen delivered from an external oxygen source (the oxygen from the external oxygen source having a known oxygen purity level) and calibrate the purity sensor based on the purity value measured by the purity sensor for the oxygen having the known oxygen purity level delivered from the external oxygen source In some embodiments, the portable oxygen concentration system 100 described herein may include additional programming, options and accessories. For instance, some programmable features that may be implemented (e.g., for programmable processor-based controllers) may be included for active sound cancellation. For example, a microphone and speaker may be provided so as to communicate with the controller. The controller may be programmed so as to create a phase-shifted or inverted sound source and thereby cancel out a portion of the sound created by the concentrator. Specifically, since sound is a pressure wave consisting of a compression phase and a rarefaction phase, a noise-cancellation speaker may be included and configured for emitting a sound wave with the same amplitude but with an inverted phase (also known as antiphase) to the original sound. Thus, when the waves combine to form a new wave (i.e., when they destructively interfere), they will effectively cancel each other out, an effect which is called phase cancellation. The resulting sound wave may be so faint as to be inaudible to human ears. A noise-cancellation speaker may be co-located with the sound source to be attenuated, e.g., concentrator compressor, and the speaker will have the same or similar audio power level as the compressor and/or vacuum pump. In a manner such as this, the sound level in the concentrator may be reduced. Since the compressor is the primary source of low frequency sound which is difficult to attenuate with passive means, active sound cancellation can be used to negate the low frequency sound, while passive means may be used to mitigate higher frequencies. Accordingly, in some implementation, an oxygen delivery device may further include a sound system to generate acoustic signals to cancel out at least some of the noise produced from operation of the oxygen delivery device. Such a sound system may be configured to generate acoustic signals with a phase that is shifted or inverted relative to at least some of the noise produced by operation of the oxygen delivery device, and may include a microphone to measure the noise produced from operation of the oxygen delivery device, and a controller (which may be different or the same as the controller 110 of FIG. 1A) configured to determine characteristics of the noise measured by the microphone, and to control the acoustic signals to be generated by a speaker. In some embodiments, another mechanism to quiet oxygen delivery devices may include the provision of an appropriate switching mechanism configured for shutting off the active cooling system of the concentrator when it is not needed. For instance, during low temperature operation, or when the heat load of the device does not warrant its use, the active cooling system of the concentrator, e.g., a fan, is turned off or run at a lower speed, to thus conserve power and reduce the noise of the overall system. Accordingly, in some implementations, an oxygen delivery device may further include a fan to cool the oxygen delivery device, at least one temperature sensor, and a controller to control operation of the fan based on data representative of temperature measured by the at least one temperature sensor. The controller is configured to cause one of, for example, terminating the operation of the fan and/or reducing speed of the fan upon a determination, based on the data representative of the temperature, that the measured temperature is below a pre-determined temperature threshold.

Additionally, in some variations, a fan may be controlled to control the temperature of a concentrator (e.g., ATF) to optimize system efficiency. Therefore, in some implementations, an oxygen delivery device may be provided that includes an oxygen delivery module to produce at least concentrated oxygen, a gas moving device (e.g., a compressor) to deliver ambient air to the oxygen delivery module, a fan to cool the oxygen delivery device, at least one temperature sensor, and one or more sensors to determine data representative of one or more of environmental conditions, operating conditions of the oxygen delivery device, and a patient's therapeutic conditions. The device also includes a controller to control operation of the fan based on the data determined by the one or more sensors, including the temperature measured by the temperature sensor, to control the fan to cause the temperature of the oxygen delivery device to be at an optimal temperature at which power consumption of the oxygen delivery device for a particular set of performance requirements is optimized. The controller may further be configured to determine the optimal temperature at which the power consumption of the oxygen delivery device for the particular set of performance requirements is optimized by, for example, varying fan speed in discrete steps over an interval of time, at each varied fan speed value determining the corresponding temperature and corresponding power consumption at the corresponding temperature, and identifying the temperature that resulted in the minimal power consumption. In some embodiments, the particular set of performance requirements includes, for example, a particular oxygen purity level of oxygen produced by the oxygen delivery module, and/or a particular fraction of inspired oxygen (FiO2) value required for the patient.

A number of different types of bags and carrying cases such as, but not by way of limitation, a shoulder bag, a backpack, a fanny pack, a front pack, and a split pack in different colors and patterns may be used to transport the system 100 and/or to transport other system accessories. A cover may be used to shield the system from inclement weather or other environmental damage.

The system 100 may also be transported with a rolling trolley/cart, a suit case, or a travel case. The travel case may be adapted to carry the system 100 and may include enough room to carry the cannula 111, extra batteries, an adapter, etc. Examples of hooks, straps, holders for holding the system 100 include, but not by way of limitation, hooks for seatbelts in cars, hooks/straps for walkers, hooks/straps, for wheel chairs, hooks/straps for hospital beds, hooks for other medical devices such as ventilators, hooks/straps for a golf bag or golf cart, hooks/straps for a bicycle, and a hanging hook.

For instance, in some embodiments, a cart may be provided in combination with the oxygen delivery device so as to increase the use and efficiency of the system as a whole. For example, a pulse oximeter may be included and positioned on the cart handle. In such a position, the oximeter can monitor the patients SpO2 while the subject is handling the cart, for instance, during exercising. Such a configuration therefore serves to alert the subject or a caregiver to the patient's health status. In some embodiments, a battery or AC power adapter may be positioned on the cart. For instance, portable oxygen concentrators are often kept on wheeled carts. Hence, the battery and/or the AC adapter can be mounted on the cart. The cart may also be configured for elevating the concentrator to a level where the patient can comfortably reach controls on the concentrator. However, in certain embodiments, the features of a cart, e.g., retractable/foldable handle and/or wheels may be integrated into the enclosure of the actual concentrator such that the concentrator and cart make up one unit. The cart and/or concentrator may additionally be configured to include a clock, timer, alarm, radio, MP3 player, cup-holder, and the like, for the convenience of a user.

Accordingly, in some embodiments, an oxygen delivery concentrator system may be provided that includes a cart, and an oxygen delivery device placed on the cart. The oxygen delivery device includes an oxygen delivery module, at least one sensor to measure data representative of at least one patient characteristic, the at least one sensor being secured to the cart (e.g., to the handle of the cart), and a controller to receive the measured data and monitor the at least one patient characteristic based on the received measured data. In some implementations, the cart may also be configured to elevate the oxygen delivery device to provide enhanced access by the patient to the oxygen delivery device. In some implementations, a battery pack and/or an AC adapter may also be mounted on the cart to facilitate transportation of such a battery pack and/or an AC adapter. In some implementations, the cart may include a retractable/foldable handle, and may further include a base to receive a housing of the oxygen delivery device, the housing including integrated wheels such that when the housing with the integrated wheels is received on the base of the cart, the wheels of the housing are used to enable mobility of the cart.

In some implementations, the oxygen delivery device may include one or more of, for example, a clock, a radio, an ashtray, and/or a cup-holder.

Figure 26:
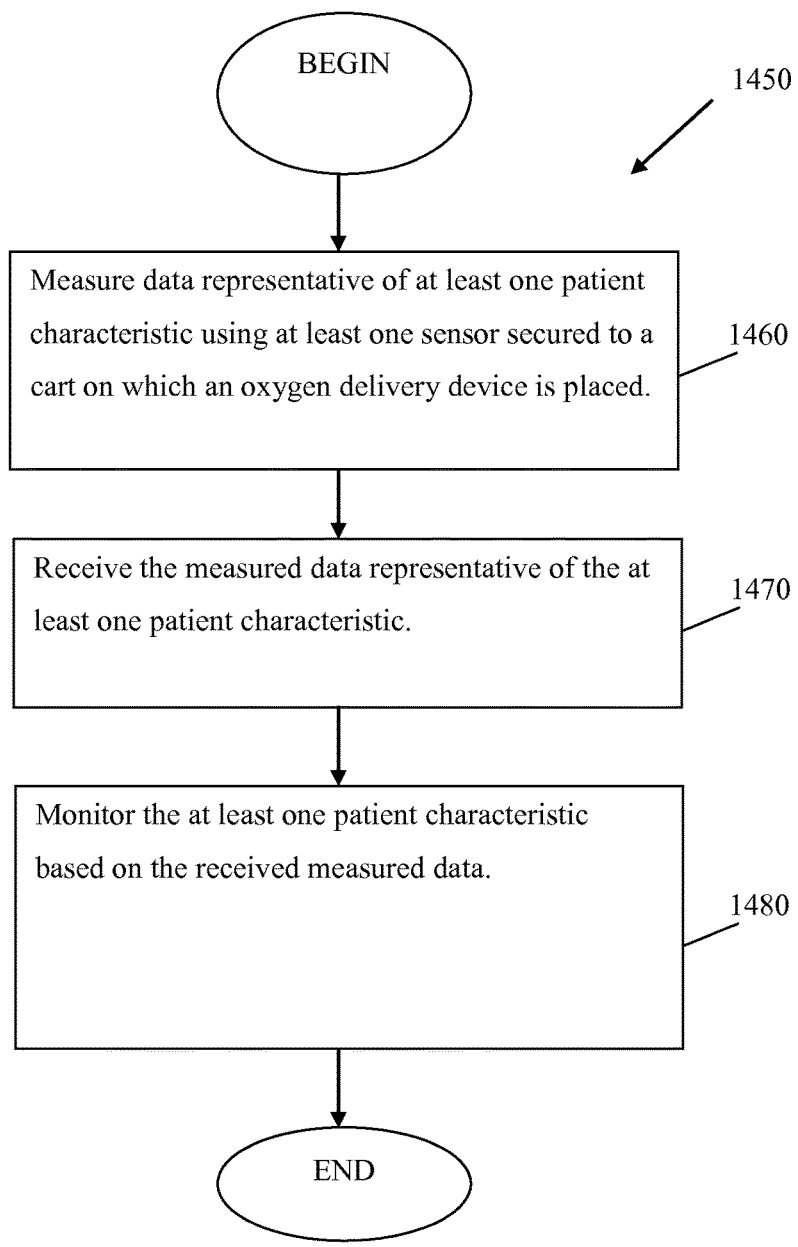
FIG. 26 is a flow chart of an example procedure to operate an oxygen delivery device.

With reference to FIG. 26, a flow chart of an example embodiment of a procedure 1450 to operate an oxygen delivery device is shown. The procedure 1450 includes measuring 1460 data representative of at least patient characteristic using at least one sensor secured to a cart on which an oxygen delivery device is placed. In some embodiments, the at least one sensor is secured to a handle of the cart such that the at least one sensor is configured to measure the data representative of the at least one patient characteristic while the patient is grasping the handle. The at least one sensor may include one or more of, for example, an oximeter to measure the patient's SpO2 level, and/or a pedometer to measure the patient's activity level. The measured data representative of the at least one patient characteristic is received 1470 (e.g., by a controller), and the at least one patient characteristic is monitored 1480 based on the received measured data. In some implementations, the procedure optionally also includes comparing the measured data representative of the at least one patient characteristic to a respective at least one pre-determined threshold value representative of normal values for the corresponding at least one patient characteristic, and communicating an alert in response to a determination that the measured data representative of the at least one patient characteristic deviates from the respective at least one pre-determined threshold value representative of the normal values corresponding at least one patient characteristic.

The system 100 may also include one or more alarm options. An alarm of the system 100 may be actuated if, for example, a sensed physiological condition of the user 108 falls outside a pre-defined range. Further, the alarm may include a panic alarm that may be manually activated by the user 108. The alarm may actuate a buzzer or other sounding device on the system 100 and/or cause a communication to be sent via a communication module (telemetry mechanism or modem) to another entity, e.g., a doctor, a 911 dispatcher, a caregiver, a family member, etc.

In some embodiments, an oxygen concentration (O2) feed back control may be provided in an oxygen concentrator device and may be configured (e.g., through software for use with a programmable-based controller) to control the output O2 so as to maintain it in a given range (for example: O2=90%+/−1%). This will allow the battery to run for a longer period of time and to improve the device control performance (in some implementations, the oxygen delivery device may be controlled to maintain the oxygen purity level at below 90%). Thus, in such implementations, an oxygen delivery device is provided that includes an oxygen delivery module to produce at least concentrated oxygen, a gas moving device (e.g., a compressor) to deliver air to an oxygen delivery module, with the gas moving device being driven by a motor to actuate the gas moving device. Such a device also includes a purity sensor to determine oxygen purity value produced by the oxygen delivery module, and a controller to control operations of at least the oxygen delivery module and the gas moving device, based at least in part on the determined oxygen purity value, to cause the purity level of the oxygen produced by the oxygen delivery module to be, for example, less than 90%.

Figure 27A:
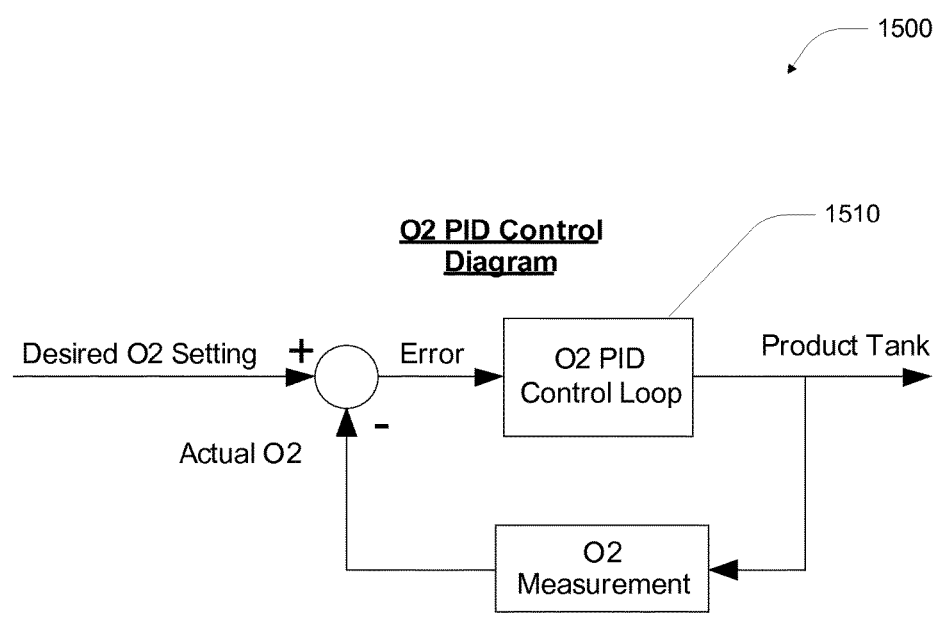
FIG. 27A is a diagram of an example embodiment of an O2 control main flow.

With reference to FIG. 27A, a diagram of an example embodiment of an O2 control main flow 1500, implemented using, for example, a PID controller 1510, is shown. The desired O2 Setting can be a fixed value or a variable value. If it is a variable, then, in some embodiments, when external AC power is connected to a device, this setting can be, for instance, 91% or higher. When the device is using a battery, the setting can be lower, for example, it can be set up to 89% or lower, but not so low that the device triggers O2 Low Alarm. This setting can be changed through a user Interface.

Figure 27B:
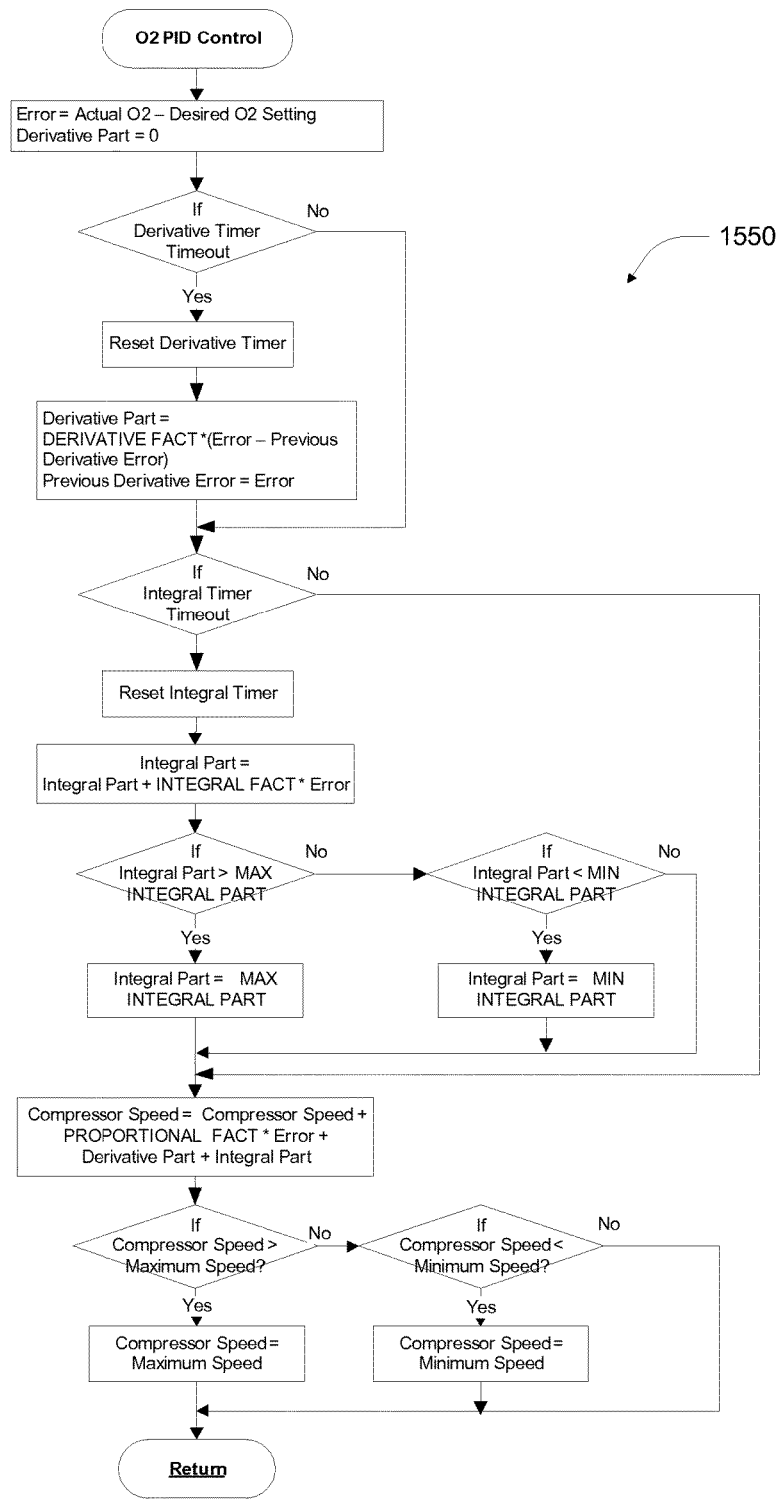
FIG. 27B is a flow chart of an example procedure to control an oxygen delivery device.
Figure 31:
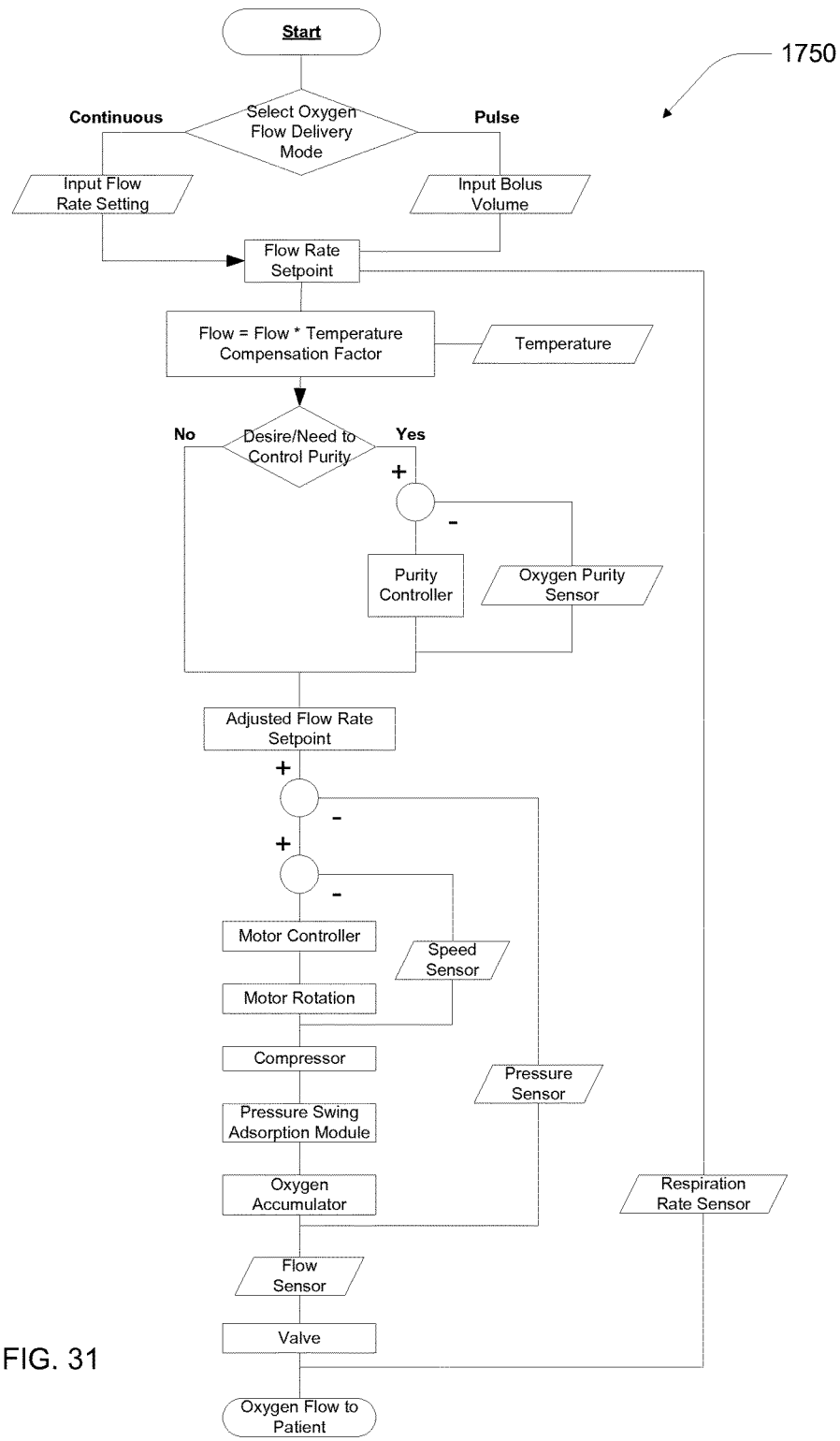
FIG. 31 is a flow chart of another example procedure to control an oxygen delivery device.

FIG. 27B is a flow chart of an example procedure 1550 to control an oxygen delivery device. More particularly, the flow chart of FIG. 27B shows the O2 control logic for compressor control. For ATF control, similar logic may be used. The flow chart shows the P (proportional), I (Integral) and D (derivative) computations. For some applications, only PI parts are used, and for some applications only the P part is used, e.g., for some simple applications. The proportional factor (PROPORTIONAL FACT), derivative factor (DERIVATIVE FACT), and integral factor (INTEGRAL FACT) may be constants that can be determined during PID tuning. In some embodiments, the Integral Timer is about 2 minutes or longer, depending on the concentrator control speed. A further embodiment of a procedure to control an oxygen delivery device (e.g., controlling the oxygen purity produced by the device, and the air flow pressure) is provided in FIG. 31.

Figure 28:
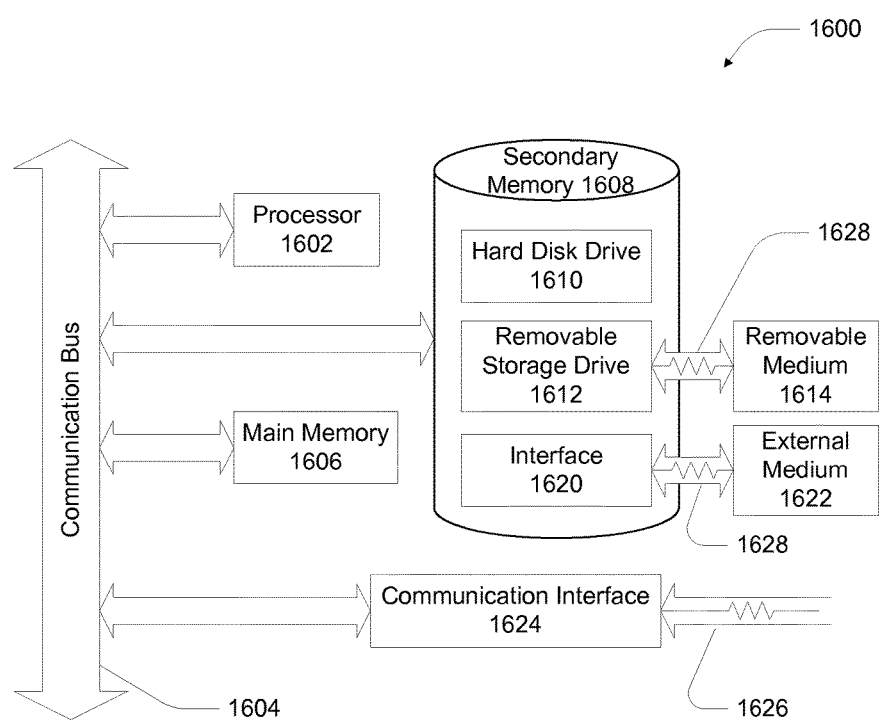
FIG. 28 is a block diagram illustrating an example computer system.

FIG. 28 is a block diagram illustrating an example computer system 1600 that may be used to implement the various computing and processor-based devices described herein. For example, the computer system 1600 may be used to implement the controller 110 of the device 100, any of the sensors 108, any remote computing devices communicating with the device 100, etc. However, other computer systems and/or architectures may be used.

The computer system 1600 includes, in some implementations, one or more processors, such as processor 1602. Additional processors may be provided, such as an auxiliary processor to manage input/output, an auxiliary processor to perform floating point mathematical operations, a special-purpose microprocessor having an architecture suitable for fast execution of signal processing procedure (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 1602.

The processor 1602 may be connected to a communication bus 1604. The communication bus 1604 may include a data channel for facilitating information transfer between storage and other peripheral components of the computer system 1600. The communication bus 1604 further may provide a set of signals used for communication with the processor 1602, including a data bus, address bus, and control bus (not shown). The communication bus 1604 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 1600 may also include a main memory 1606 and may also include a secondary memory 1608. The main memory 1606 provides storage of instructions and data for programs executing on the processor 1602. The main memory 1606 is typically semiconductor-based memory such as dynamic random access memory ("DRAM") and/or static random access memory ("SRAM"). Other semiconductor-based memory types include, for example, synchronous dynamic random access memory ("SDRAM"), Ramous dynamic random access memory ("RDRAM"), ferroelectric random access memory ("FRAM"), and the like, including read only memory ("ROM").

The secondary memory 1608 may optionally include a hard disk drive 1610 and/or a removable storage drive 1612, for example a floppy disk drive, a magnetic tape drive, a compact disc ("CD") drive, a digital versatile disc ("DVD") drive, etc. The removable storage drive 1612 reads from and/or writes to a removable storage medium 1614. Removable storage medium 1614 may be, for example, a floppy disk, magnetic tape, CD, DVD, etc.

The removable storage medium 1614 may be a non-transitory computer readable medium having stored thereon computer executable code (e.g., software) and/or data. Executable code may include computer executable code to perform any of the procedures described herein. The computer software or data stored on the removable storage medium 1614 is read into the computer system 1600 as electrical communication signals 1628.

In alternative embodiments, secondary memory 1608 may include other similar implementations for enabling computer programs or other data or instructions to be loaded into the computer system 1600. Such implementations may include, for example, an external storage medium 1622 and an interface 1620. Examples of external storage medium 1622 may include an external hard disk drive or an external optical drive, or and external magneto-optical drive.

Other examples of secondary memory 1608 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 1622 and interfaces 1620, which allow software and data to be transferred from the removable storage unit 1622 to the computer system 1600.

Computer system 1600 may also include a communication interface 1624. The communication interface 1624 allows software and data to be transferred between computer system 1600 and external devices (e.g. printers), networks, or information sources. For example, computer software or executable code may be transferred to computer system 1600 from a network server via communication interface 1624. Examples of communication interface 1624 include a modem, a network interface card ("NIC"), a communications port, a PCMCIA slot and card, an infrared interface, and an IEEE 1394 fire-wire, just to name a few, which enable wire-based or wireless communication.

Communication interface 1624 may implement industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 1624 are generally in the form of electrical communication signals 1628. These signals 1628 may be provided to communication interface 1624 via a communication channel 1626. Communication channel 1626 carries signals 1628 and can be implemented using a variety of wired or wireless communication means including wire or cable, fiber optics, conventional phone line, cellular phone link, wireless data communication link, radio frequency ("RE") link, or infrared link, just to name a few.

Computer executable code (i.e., computer programs or software) may be stored in the main memory 1606 and/or the secondary memory 1608. Computer programs can also be received via communication interface 1624 and stored in the main memory 1606 and/or the secondary memory 1608. Such computer programs, when executed, enable the computer system 1600 to perform the various functions described herein.

In this disclosure, the term "computer readable medium" is used to refer to any non-transitory media used to provide computer executable code (e.g., software and computer programs) to the computer system 1600. Examples of these media include main memory 1606, secondary memory 1608 (including hard disk drive 560, removable storage medium 1614, and external storage medium 1622), and any peripheral device communicatively coupled with communication interface 1624 (including a network information server or other network device). These computer readable media are means for providing executable code, programming instructions, and software to the computer system 1600.

In embodiments that are implemented using software, the software may be stored on a computer readable medium and loaded into computer system 1600 by way of removable storage drive 1612, interface 1620, or communication interface 1624. In such embodiments, the software is loaded into the computer system 1600 in the form of electrical communication signals 1628. The software, when executed by the processor 1602, causes the processor 1602 to perform the features and functions described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein may also be used. Various embodiments may also be implemented using a combination of both hardware and software.

The various illustrative logical blocks, modules, circuits, and methods described in connection with the above described figures and the embodiments disclosed herein can often be implemented as electronic hardware, computer software, or combinations of both.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the methods/procedures described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

A number of implementations of the invention have been described. Nevertheless, it will be understood that various modifications may be made without departing from the spirit and scope of the invention. Accordingly, other embodiments are within the scope of the following claims.

What is claimed is:

1. An oxygen delivery device comprising:
an oxygen delivery module configured to receive compressed air from a compressor comprising a piston having a single rotor configured to orbit around first eccentric on a shaft to compress ambient air into the compressed air, the oxygen deliver module comprising a rotary valve assembly that rotates with respect to a plurality of adsorption beds to selectively transfer fluids through the plurality of adsorption beds in order to separate concentrated oxygen and other gases within the compressed air, the compressor configured to be combined with a vacuum pump comprising another piston having a single rotor configured to orbit around a second eccentric on the shaft to vacuum out the other gases, the compressor and the vacuum being separated by an endplate that excludes one or more motors driving the compressor and the vacuum pump, the endplate overlaying and being adjacent to a stator of the compressor and a stator of the vacuum pump, wherein the endplate completely separates a first housing containing the first stator and a second housing containing the second stator, wherein the stator of the compressor, the stator of the vacuum pump, and the endplate all have the same height measured along a dimension perpendicular to a long axis of the shaft, and wherein the endplate includes a only a single vent hole that extends through the endplate and communicates with ambient pressure, the vent hole being positioned entirely within the endplate and having (1) a first end that communicates solely with an endplate chamber entirely defined by the endplate and entirely contained within the endplate (2) a second end that communicates with the ambient pressure, wherein the vent hole is straight along its entire length and extends radially outward from the endplate chamber to a radial end of the endplate and provides a sole passageway for fluid to vent out of the endplate chamber through the endplate and to atmosphere, and wherein the endplate chamber fluidly communicates with both the compressor and the vacuum such that gas can leak from the compressor or the vacuum into the endplate chamber, wherein the vent hole vents the gas that leaks into the endplate chamber to atmosphere;
at least one sensor to detect patient breathing; and
a controller configured to control the oxygen delivery module to cause the oxygen delivery module to deliver the concentrated oxygen to the patient based on data from the at least one sensor such that in response to a determination, based on data from the at least one sensor, that no breathing is detected for a first predetermined period of time, the controller causes the oxygen delivery module to deliver the concentrated oxygen to the patient in continuous flow mode, and in response to a determination, based on additional data from the at least one sensor, that breathing is detected for a second period of time, the controller causes the oxygen delivery module to deliver the concentrated oxygen to the patient in a pulse flow mode.

2. The oxygen delivery device of claim 1, wherein the at least one sensor is configured to detect patient breathing by performing one of: continuous detection of patient breathing, and periodic detection of patient breathing,
wherein the compressor and the vacuum are enclosed within a single housing.

3. The oxygen delivery device of claim 1, wherein the controller is further configured, subsequent to the determination that no breathing is detected and to causing the oxygen delivery module to deliver the concentrated oxygen to the patient in the continuous flow mode, to:
terminate the continuous flow delivery of the concentrated oxygen to the patient, and
cause the oxygen delivery module to deliver the concentrated oxygen to the patient in the pulse dose mode in response to one or more of:
(a) a determination that the second period of time has elapsed since the determination that no breathing is detected, and
(b) the determination, based on the additional data from the at least one sensor, that the patient is breathing.

4. The oxygen delivery device of claim 1, wherein the at least one sensor includes a pressure sensor fluidly connected to a cannula coupled to the oxygen delivery module, the cannula structured to deliver the concentrated oxygen from the oxygen delivery module through the patient's nasal passages.

5. The oxygen delivery device of claim 4, wherein the pressure sensor fluidly connected to the cannula is configured to detect pressure changes within the patient's nasal passages, and to generate data representative of the pressure changes.

6. The oxygen delivery device of claim 5, wherein the controller is further configured to:
receive a feed of the data generated by the pressure sensor;
perform filtering operation on the feed of the data generated by the pressure sensor to determine onset of an inspiratory cycle for the patient.

7. The oxygen delivery device of claim 1, wherein the oxygen delivery module comprises one or more of: a pressure swing adsorption system, a vacuum-pressure swing adsorption system, a vacuum swing adsorption system, and a membrane separation device.

* * * * *